United States Patent
Bénard et al.

(10) Patent No.: US 11,395,857 B2
(45) Date of Patent: *Jul. 26, 2022

(54) RADIOLABELED MELANOCORTIN 1 RECEPTOR-SPECIFIC ALPHA-MELANOCYTE-STIMULATING HORMONE ANALOGUES FOR IMAGING OR THERAPY

(71) Applicant: PROVINCIAL HEALTH SERVICES AUTHORITY, Vancouver (CA)

(72) Inventors: François Bénard, Vancouver (CA); Kuo-Shyan Lin, Vancouver (CA); Chengcheng Zhang, Vancouver (CA); Zhengxing Zhang, Vancouver (CA)

(73) Assignee: PROVINCIAL HEALTH SERVICES AUTHORITY, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/494,367

(22) Filed: Oct. 5, 2021

(65) Prior Publication Data

US 2022/0040340 A1 Feb. 10, 2022

Related U.S. Application Data

(63) Continuation of application No. 17/057,506, filed as application No. PCT/CA2019/050703 on May 23, 2019.

(60) Provisional application No. 62/690,009, filed on Jun. 26, 2018, provisional application No. 62/675,757, filed on May 23, 2018.

(51) Int. Cl.
*A61K 51/08* (2006.01)
*A61K 51/04* (2006.01)
(Continued)

(52) U.S. Cl.
CPC ............ *A61K 51/088* (2013.01); *A61K 47/08* (2013.01); *A61K 51/0482* (2013.01); *A61P 35/00* (2018.01)

(58) Field of Classification Search
CPC ........ A61K 51/04; A61K 51/08; A61K 47/08; A61P 35/00
See application file for complete search history.

(56) References Cited

U.S. PATENT DOCUMENTS 5,650,134 A 7/1997 Albert et al.
8,114,381 B2 2/2012 Perrin et al.
(Continued)

FOREIGN PATENT DOCUMENTS

CN 106967152 A 7/2017
WO WO 2005/077967 A1 8/2005
(Continued)

OTHER PUBLICATIONS

Antunes et al., "Influence of Different Spacers on the Biological Profile of a DOTA-Somatostatin Analogue," Bioconjugate Chemistry, 2007, vol. 18, pp. 84-92.
Banerjee et al., "Clinical applications of Gallium-68," Applied Radiation and Isotopes, 2013, vol. 76, pp. 2-13.
Breeman et al., "Somatostatin receptor-mediated imaging and therapy: basic science, current knowledge, limitations and future perspectives," European Journal of Nuclear Medicine, Sep. 2001, vol. 28, No. 9, pp. 1421-1429.
Buchmann et al., "Comparison of $^{68}$Ga-DOTATOC PET and $^{111}$In-DTPAOC (Octreoscan)SPECT in patients with neuroendocrine tumours," Eur J Nucl Med Mol Imaging., 2007, vol. 34, pp. 1617-1626.
Cai et al., "RGD-based PET tracers for imaging receptor integrin $\alpha_v\beta_3$ expression," Journal of Labelled Compounds and Radiopharmaceuticals, 2013, vol. 56, pp. 264-279.
Chin et al., "First Experience with Clinical-Grade [$^{18}$F]FPP(RGD)$_2$: An Automated Multi-step Radiosynthesis for Clinical PET Studies," Mol Imaging Biol., 2012, vol. 14, pp. 88-95.
(Continued)

*Primary Examiner* — Michael G. Hartley
*Assistant Examiner* — Jagadishwar R Samala
(74) *Attorney, Agent, or Firm* — Cooley LLP

(57) ABSTRACT

A compound is provided comprising a melanocortin 1 receptor (MC1R) targeting peptide (MC1RTP), a radiolabeling group, and a linker joining the MC1RTP to the radio labeling group. The MC1RTP is linear or cyclized, and comprises a sequence of Formula I or Formula II: $Xaa^1$-$Xaa^{2a}$-$Xaa^3$-$Xaa^4$-$Xaa^5$-$Xaa^6$-$Xaa^{7a}$ (I) or $Xaa^1$-$Xaa^{2b}$-$Xaa^3$-$Xaa^4$-$Xaa^5$-$Xaa^6$-$Xaa^{7b}$ (II). $Xaa^1$ is L-/D-Nle, L-/D-Nle, L-/D-Ala, L-/D-Leu, L-/D-Ile, D-Ile, L-/D-Cys, L-/D-Met, L-/D-Phe, L-/D-Trp, L-/D-Val, L-/D-Nal, L-/D-2-Nal, Gly, L-/D-α-aminobutryic acid, L-/D-norvaline, or L-/D-homonorleucine. $Xaa^{2a}$ and $Xaa^{7b}$ are L-/D-Cys, L-/D-Asp, L-/D-Glu, L-/D-2-Aad, L-/D-3-Aad, L-/D-Pra, L-/D-Hpg, or L-/D-Bpg. $Xaa^{2b}$ and $Xaa^{7a}$ are L-/D-Cys, L-/D-Lys, L-/D-Orn, L-/D-Dab, L-/D-Dap, L-/D-Lys($N_3$), L-/D-Orn($N_3$), L-/D-Dab($N_3$), L-/D-Dap($N_3$), L-/D-2-(5'-azidopentyl)alanine, or L-/D-2-(6'-azidohexyl)alanine. $Xaa^3$ is L-/D-His, Pro, beta-(1,2,3-triazol-4-yl)-L-alanine, beta-(1,2,3-triazol-4-yl)-D-alanine, 1,2,4-triazole-3-alanine, or 1,2,4-triazole-3-D-alanine. $Xaa^4$ is L-/D-Phe, L-/D-2-Nal, L-/D-Phe(4-F), L-/D-Phe(4-Cl), L-/D-Phe(4-Br), L-/D-Phe(4-I), L-/D-Phe(4-NH2), or L-/D-Phe(4-NO2). $Xaa^5$ is L-/D-Arg, L-/D-hArg), Leu, L-/D-Agb, or L-/D-Agp. $Xaa^6$ is L-/D-Trp, L-/D-Phe, L-/D-Trp(5-Br), L-/D-Trp(5-OCH3), L-/D-Trp(6-F), L-/D-Trp(5-OH) or L-/D-Trp(CHO). One or more amino acid residues of the MC1RTP is alpha N-methylated, wherein 1, 2, 3 or 4 of $Xaa^3$, $Xaa^5$, $Xaa^6$ and $Xaa^{7a}$ is alpha N-methylated or wherein 1, 2, 3 or 4 of $Xaa^3$, $Xaa^5$, $Xaa^6$ and $Xaa^{7b}$ is alpha N-methylated. The linker comprises an albumin-binding group.

33 Claims, 8 Drawing Sheets

(51) Int. Cl.
    *A61K 47/08*     (2006.01)
    *A61P 35/00*     (2006.01)

(56) References Cited

U.S. PATENT DOCUMENTS

| | | | |
|---|---|---|---|
| 8,153,101 | B2 | 4/2012 | McBride et al. |
| 8,574,546 | B2 | 11/2013 | Perrin et al. |
| 8,691,761 | B2 | 4/2014 | Rivier et al. |
| 10,150,804 | B2 | 12/2018 | Benard et al. |
| 2014/0112873 | A1* | 4/2014 | Gillies .................. C07K 14/68 424/9.323 |
| 2014/0147381 | A1 | 5/2014 | Espenan |
| 2021/0024605 | A1 | 1/2021 | Perrin et al. |
| 2021/0205483 | A1 | 7/2021 | Benard et al. |

FOREIGN PATENT DOCUMENTS

| | | |
|---|---|---|
| WO | WO 2009/012596 A1 | 1/2009 |
| WO | WO 2012/094334 A1 | 7/2012 |
| WO | WO 2012/118909 A1 | 9/2012 |
| WO | WO 2014/134716 A1 | 9/2014 |
| WO | WO 2015/100498 A1 | 7/2015 |

OTHER PUBLICATIONS

Doedens et al., "Multiple N-Methylation of MT-II Backbone Amide Bonds Leads to Melanocortin Receptor Subtype hMC1R Selectivity: Pharmacological and Conformational Studies," J Am Chem Soc, 2010, vol. 132, pp. 8115-8128.

Eberl et al., "High beam current operation of a PETtrace™ cyclotron for $^{18}$F production," Applied Radiation and Isotopes, 2012, vol. 70, pp. 922-930.

Extended Search Report for European Patent Application No. 15733077.0, dated Jun. 19, 2017, 6 pages.

Fani et al., "Unexpected Sensitivity of sst$^2$ Antagonists to N-Terminal Radiometal Modifications," The Journal of Nuclear Medicine, Sep. 2012, vol. 53, No. 9, pp. 1481-1489.

Gabriel et al., "$^{68}$Ga-DOTA-Tyr$^3$-Octreotide PET in Neuroendocrine Tumors: Comparison with Somatostatin Receptor Scintigraphy and CT," The Journal of Nuclear Medicine, Apr. 2007, vol. 48, No. 4, pp. 508-518.

Gabriel et al., "An Intrapatient Comparison of $^{99m}$Tc-EDDA/HYNIC-TOC with $^{111}$In-DTPA Octreotide for Diagnosis of Somatostatin Receptor-Expressing Tumors," The Journal of Nuclear Medicine, May 2003, vol. 44, No. 5, pp. 708-716.

Ginj et al., "Design, Synthesis, and Biological Evaluation of Somatostatin-Based Radiopeptides," Chemistry & Biology, Oct. 2006, vol. 13, pp. 1081-1090.

Guo et al., "Preparation and Biological Evaluation of $^{64}$Cu Labeled Tyr$^3$-Octreotide using a Phosphonic Acid-Based Cross-Bridged Macrocyclic Chelator," Bioconjugate Chemistry, 2012, vol. 23, pp. 1470-1477.

Henze et al., "PET Imaging of Somatostatin Receptors Using [$^{68}$GA]DOTA-D-Phe$^1$-Tyr$^3$-Octreotide: Firest Results in Patients with Meningiomas," The Journal of Nuclear Medicine, Jul. 2001, vol. 42, No. 7, pp. 1053-1056.

International Search Report and Written Opinion for International (PCT) Patent Application No. PCT/CA2015/000002, dated May 4, 2015, 10 pages.

International Search Report and Written Opinion of the International Searching Authority for International Application No. PCT/CA2019/050703, dated Jul. 17, 2019, 11 pages.

International Search Report and Written Opinion of the International Searching Authority for International Application No. PCT/CA2019/051853, dated Feb. 18, 2020, 8 pages.

Kayani "A Comparison of $^{68}$Ga-DOTATATE and $^{18}$F-FDG PET/CT in Pulmonary Neuroendocrine Tumors," The Journal of Nuclear Medicine, Dec. 2009, vol. 50, No. 12, pp. 1927-1932.

Kemerink et al., "Effect of the positron range of $^{18}$F, $^{68}$Ga and $^{124}$I on PET/CT in lung equivalent materials," Eur J Nucl Med Mol Imaging, 2011, vol. 38, pp. 940-948.

Krausz et al., "SPECT/CT hybrid imaging with $^{111}$In-pentetreotide in assessment of neuroendocrine tumours," Clinical Endocrinology, 2003, vol. 59, pp. 565-573.

Kwekkeboom et al. "Peptide Receptor Radionuclide Therapy in Patients With Gastroenteropancreatic Neuroendocrine Tumors," Seminars in Nuclear Medicine, Mar. 2010, vol. 40, No. 2, pp. 78-88.

Kwekkeboom et al. "Somatostatin receptor-based imaging and therapy of gastroenteropancreatic neuroendocrine tumors," Endocr Relat Cancer., 2010, vol. 17, pp. R53-R73.

Laforest et al. "Image quality with non-standard nuclides in PET," QJ Nucl Med Mol Imaging, 2008, vol. 52, pp. 151-158.

Laverman et al., "A Novel Facile Method of Labeling Octreotide with $^{18}$F-Fluorine," The Journal of Nuclear Medicine, Mar. 2010, vol. 51(3), pp. 454-461.

Laverman et al., "Optimized labeling of NOTA-conjugated octreotide with F-18," Tumor Biol., 2012, vol. 33, pp. 427-434.

Leyton et al., "Targeting Somatostatin Receptors: Preclinical Evaluation of Novel $^{18}$F-Fluoroethyltriazole-Tyr$^3$-Octreotate Analogs for PET," The Journal of Nuclear Medicine, Sep. 2011, vol. 52(9), pp. 1441-1448.

Li et al., "One-step and one-pot-two-step radiosynthesis of cyclo-RGD-$^{18}$F-aryltrifluoroboronate conjugates for functional imaging," Am. J. Nucl. Med. Mol. Imaging, 2013, vol. 3(1), pp. 44-56 (32 pages).

Liu et al., ""Kit-like" radiosynthesis and biological evaluation of an F-labeled 4-(2-Aminoethyl)-benzenesulfonamide (AEBS) trimer for imaging carbonic anhydrase IX expression with positron emission tomography," World Molecular Imaging Congress, Sep. 19, 2013—poster, 1 page.

Liu et al., "$^{18}$F-trifluoroborate derivatives of [des-arg$^{10}$]kallidin for imaging bradykinin b1 receptor expression with positron emission tomography," Molecular Pharmaceutics, 2015, vol. 12, No. 3, pp. 974-982.

Liu et al., "An Organotrifluoroborate for Broadly Applicable One-Step $^{18}$F-Labeling," Angewandte Chemie International Edition, Sep. 2014, vol. 53, No. 44, pp. 11876-11880.

Liu et al., "Facile synthesis and biological evaluation of an 18F-labeled 4-(2-aminoethyl) benzenesulfonamide (AEBS) trimer for imaging carbonic anhydrase IX expression with positron emission tomography," World Molecular Imaging Congress, Sep. 19, 2013, Presentation No. LBAP 029, 2 pages.

Liu et al., "Kit-like $^{18}$F-labeling of RGD- $^{19}$F-Arytrifluroborate in high yield and at extraordinarily high specific activity with preliminary in vivo tumor imaging," Nuclear Medicine and Biology, vol. 40, 2013, pp. 841-849.

Liu et al., "Preclinical evaluation of a high affinity 18F-trifluoroborate octreotate derivative for somatostatin receptor imaging—poster," UBC, 2014, 1 page.

Liu et al., "Preclinical Evaluation of a High-Affinity $^{18}$F-Trifluoroborate Octreotate Derivative for Somatostatin Receptor Imaging," Journal of Nuclear Medicine, Sep. 2014, vol. 55(9), pp. 1499-1505.

Liu et al., "Preclinical Evaluation of a Novel 18F-Labelled Somatostatin Receptor-Binding Peptide—Abstract Proof," ScholarOne, Inc., 2014, Control ID: 1931699, 4 pages.

Liu et al., "Preclinical evaluation of a novel $^{18}$F-labelled somatostatin receptor-binding peptide," The Journal of Nuclear Medicine, 2014, vol. 55 (Supplement 1):1089, 1 page.

Liu et al., "Rapid, one-step, high yielding $^{18}$F-labeling of an aryltrifluoroborate bioconjugate by isotope exchange at very high specific activity," Journal of Labelled Compounds and Radiopharmaceuticals, 2012, vol. 55, pp. 491-496.

Liu et al., "Stoichiometric Leverage: Rapid 18F-Aryltrifluoroborate Radiosynthesis at High Specific Activity for Click Conjugation," Angew. Chem. Int. Ed., 2013, vol. 52, pp. 2303-2307.

Matteson et al., "Iodomethaneboronic Esters And Aminomethaneboronic Esters," Journal of Organometallic Chemistry, 1979, vol. 170, pp. 259-264.

Means et al. "Chemical Modifications of Proteins: History and Applications," Bioconjugate Chemistry, 1990, vol. 1, No. 1, pp. 2-12.

(56) References Cited

OTHER PUBLICATIONS

Poeppel et al., "[68]GA-DOTATOC Versus $^{68}$Ga-DOTATATE PET/CT in Functional Imaging of Neuroendocrine Tumors," The Journal of Nuclear Medicine, Dec. 2011, vol. 52(12), pp. 1864-1870.

Poethko et al., "Two-Step Methodology for High-Yield Routine Radiohalogenation of Peptides: [18]F-Labeled RGD and Octreotide Analogs," The Journal of Nuclear Medicine, May 2004, vol. 45 No. 5, pp. 892-902.

Pourghisian et al., "[18]F-AmBF$_3$-MJ9: a novel radiofluorinated bombesin derivative for prostate cancer imaging," Bioorganic & Medicinal Chemistry, 2015, vol. 23, No. 7, pp. 1500-1506.

Reubi et al., "Affinity profiles for human somatostatin receptor subtypes SST1-SST5 of somatostatin radiotracers selected for scintigraphic and radiotherapeutic use," European Journal of Nuclear Medicine, Mar. 2000, vol. 27, No. 3, pp. 273-282.

Roxin et al., "A metal-free DOTA-conjugated $^{18}$F-labeledradiotracer: [$^{18}$F]DOTA-AMBFi LLP2A for imaging VLA-4 Over-expression in murine melanoma with improved tumor uptake and greatly enhanced renal clearance," Bioconjugate Chem. 2019, 30, 1210-1219.

Roxin et al. "Preliminary evaluation of 18F-labeled LLP2A-trifluoroborate conjugates as VLA-4 (α4β1 integrin) specific radiotracers for PET imaging of melanoma" Nuclear Medicine and Biology 61 (2018) 11-20.

Sprague et al., "Preparation and Biological Evaluation of Copper-64-Labeled Tyr3-Octreotate Using a Cross-Bridged Macrocyclic Chelator," Clinical Cancer Research, Dec. 2004, vol. 10, pp. 8674-8682.

Storch et al., "Evaluation of [$^{99m}$Tc/EDDA/HYNIC[0]]Octreotide Derivatives Compared with [$^{111}$In-DOTA[0],Tyr[3],Thr[8]]Octreotide and [$^{111}$In-DTPA[0]]Octreotide: Does Tumor or Pancreas Uptake Correlate with the Rate of Internalization?" The Journal of Nuclear Medicine, Sep. 2005, vol. 46, No. 9, pp. 1561-1569.

Vallabhajosula et al., "Preclinical Evaluation of Technetium-99m-Labeled Somatostatin Receptor-Binding Peptides," The Journal of Nuclear Medicine, Jun. 1996, vol. 37, No. 6, pp. 1016-1022.

Virgolinl et al., "Somatostatin Receptor Subtype Specificity and in Vivo Binding of a Novel Tumor Tracer. [99m]Tc-P829[1]," Cancer Research, May 1998, vol. 58, pp. 1850-1859.

Wängler et al., "One-Step [18]F-Labeling of Carbohydrate-Conjugated Octreotate-Derivatives Containing a Silicon-Fluoride-Acceptor (SiFA): In Vitro and in Vivo Evaluation as Tumor Imaging Agents for Positron Emission Tomography," Bioconjugate Chem., 2010, vol. 21(12), pp. 2289-2296.

Wester et al., "PET imaging of somatostatin receptors: design, synthesis and preclinical evaluation of a novel 18F-labelled, carbohydrated analogue of octreotide," European Journal of Nuclear Medicine and Molecular Imaging, Jan. 2003, vol. 30, No. 1, pp. 117-122.

Zhan et al., "Hydration of the Fluoride Anion: Structures and Absolute Hydration Free Energy from First-Principles Electronic Structure Calculations," J Phys Chem A., 2004, vol. 108, pp. 2020-2029.

Zhang et al., "Preclinical Melanoma Imaging with $^{68}$Ga-labeled α-Melanocyte-Stimulating Hormone Derivatives Using PET," Theranostics, 2017, vol. 7, Issue 4, pp. 805-813.

Zhang et al., "Selectively targeting the melanocortin-1 receptor with N-methylation of an αMSH derivative for PET imaging of melanoma," Journal of Nuclear Medicine, May 2018, 59 (Supplement 1): 611.

Zhang et al., "Targeting the melanocortin-1 receptor with $^{177}$Lu-labeled alpha-melanocyte stimulating hormone derivatives: increased tumor uptake using an albumin binder," Journal of Nuclear Medicine, May 2018, 59 (Supplement 1): 1106.

\* cited by examiner

RADIOLABELED MELANOCORTIN 1 RECEPTOR-SPECIFIC ALPHA-MELANOCYTE-STIMULATING HORMONE ANALOGUES FOR IMAGING OR THERAPY

CROSS-REFERENCES TO RELATED APPLICATIONS

This application is a continuation of U.S. application Ser. No. 17/057,506, filed Nov. 20, 2020, which is a U.S. National Stage Application under 35 U.S.C. § 371 of International Application No. PCT/CA2019/050703, filed May 23, 2019, which claims priority to U.S. Provisional Application No. 62/675,757, filed May 23, 2018, and U.S. Provisional Application No. 62/690,009, filed Jun. 26, 2018, each of which is hereby incorporated herein by reference in their entireties.

FIELD OF INVENTION

The present invention relates to alpha-melanocyte-stimulating hormone analogues which target melanocortin 1 receptor.

BACKGROUND OF THE INVENTION

Current imaging technologies for metastatic melanomas, e.g. including cutaneous, amelanotic and uveal melanomas, have limited sensitivity for detecting small metastatic lesions, early nodal metastases, and liver metastases. In addition, current treatments for metastatic melanomas have limited success at later stages.

The melanocortin 1 receptor (MC1R) is specifically expressed in cutaneous, amelanotic and uveal melanomas. The low level of MC1R expression in normal tissues makes this protein an attractive target for radionuclide imaging and therapy. The endogenous ligand of MC1R is alpha-melanocyte-stimulating hormone (αMSH), which binds MC1R with sub-nanomolar binding affinity. However, αMSH also binds to other melanocortin receptors, including MC3R, MC4R and MC5R. αMSH does not bind to MC2R, which is selectively activated by adrenocorticotropic hormone.

While peptide analogues of αMSH have been developed for imaging applications (e.g. $^{68}$Ga-labeled CCZ01048 having sequence DOTA-Pip-Nle-cyclo[Asp-His-D-Phe-Arg-Trp-Lys]-NH$_2$; see Zhang et al., 2017 Theranostics 7(4): 805-813)), there remains a need for higher selectivity for MC1R over the other melanocortin receptors to reduce off-target accumulation of MC1R targeting radiolabeled peptides in vivo. The metabolic stability of the peptide analogues is also important to achieve high tumour accumulation and long term retention of the radiolabeled peptide analogues for in vivo for imaging of MC1R-expressing tissues and/or therapy of MC1R-related conditions or diseases (e.g. melanoma, non-melanoma skin cancers and others).

No admission is necessarily intended, nor should it be construed, that any of the preceding information constitutes prior art against the present invention.

SUMMARY OF THE INVENTION

Various embodiments in this disclosure relate to a compound comprising a melanocortin 1 receptor (MC1R) targeting peptide (MC1RTP), a radiolabeling group, and a linker joining the MC1RTP to the radiolabeling group, wherein: the MC1RTP is linear or cyclized, and comprises a sequence of Formula I or Formula II (as defined below); $Xaa^1$ is norleucine (Nle), D-Nle, Ala, D-Ala, Leu, D-Leu, Ile, D-Ile, Cys, D-Cys, Met, D-Met, Phe, D-Phe, Trp, D-Trp, Val, D-Val, 3-(1-naphtyl)alanine (Nal), D-Nal, 3-(2-naphtyl)alanine (2-Nal), D-2-Nal, Gly, α-aminobutryic acid, D-α-aminobutryic acid, norvaline, D-norvaline, homonorleucine, or D-homonorleucine; $Xaa^{2a}$ is Cys, D-Cys, Asp, D-Asp, Glu, D-Glu, 2-aminoadipic acid (2-Aad), D-2-Aad, 3-aminoadipic acid (3-Aad), D-3-Aad, propargylglycine (Pra), D-Pra, homopropargylglycine (Hpg), D-Hpg, beta-homopropargylglycine (Bpg) or D-Bpg; $Xaa^{2b}$ is Cys, D-Cys, Lys, D-Lys, Ornithine (Orn), D-Orn, 2,4-diaminobutyric acid (Dab), D-Dab, 2,3-diaminopropionic acid (Dap), D-Dap, Lys(N$_3$), D-Lys(N$_3$), Orn(N$_3$), D-Orn(N$_3$), Dab(N$_3$), D-Dab(N$_3$), Dap(N$_3$), D-Dap(N$_3$), 2-(5'-azidopentyl)alanine, D-2-(5'-azidopentyl)alanine, 2-(6'-azidohexyl)alanine or D-2-(6'-azidohexyl)alanine; $Xaa^3$ is His, D-His, Pro, beta-(1,2,3-triazol-4-yl)-L-alanine, beta-(1,2,3-triazol-4-yl)-D-alanine, 1,2,4-triazole-3-alanine, or 1,2,4-triazole-3-D-alanine; $Xaa^4$ is Phe, D-Phe, 2-Nal, D-2-Nal, Phe(4-F), D-Phe(4-F), Phe(4-Cl), D-Phe(4-Cl), Phe(4-Br), D-Phe(4-Br), Phe(4-I), D-Phe(4-I), Phe(4-NH$_2$), D-Phe(4-NH$_2$), Phe(4-NO$_2$), or D-Phe(4-NO$_2$); $Xaa^5$ is Arg, D-Arg, homoarginine (hArg), D-hArg, Leu, D-Leu, 2-amino-4-guanidinobutyric acid (Agb), D-Agb, 2-amino-3-guanidinopropionic acid (Agp) or D-Agp; $Xaa^6$ is Phe, D-Phe, Trp, D-Trp, Trp(5-Br), D-Trp(5-Br), Trp(5-OCH$_3$), D-Trp(5-OCH$_3$), Trp(6-F), D-Trp(6-F), Trp(5-OH), D-Trp(5-OH), Trp(CHO), or D-Trp(CHO); $Xaa^{7a}$ is Cys, D-Cys, Lys, D-Lys, Orn, D-Orn, Dab, D-Dab, Dap, D-Dap, Lys(N$_3$), D-Lys(N$_3$), Orn(N$_3$), D-Orn(N$_3$), Dab(N$_3$), D-Dab(N$_3$), Dap(N$_3$), D-Dap(N$_3$), 2-(5'-azidopentyl)alanine, D-2-(5'-azidopentyl)alanine, 2-(6'-azidohexyl)alanine or D-2-(6'-azidohexyl)alanine; $Xaa^{7b}$ is Cys, D-Cys, Asp, D-Asp, Glu, D-Glu, 2-Aad, D-2-Aad, 3-Aad, D-3-Aad, Pra, D-Pra, Hpg, D-Hpg, Bpg or D-Bpg; the MC1RTP is optionally C-terminally amidated; one or more amino acid residues of the MC1RTP is alpha N-methylated, wherein 1, 2, 3 or 4 of $Xaa^3$, $Xaa^5$, $Xaa^6$ and $Xaa^{7a}$ is alpha N-methylated and wherein 1, 2, 3 or 4 of $Xaa^3$, $Xaa^5$, $Xaa^6$ and $Xaa^{7b}$ is alpha N-methylated; and the linker comprises an albumin-binding group. In some embodiments, each of $Xaa^1$, $Xaa^{2a}$, $Xaa^{2b}$, $Xaa^3$, $Xaa^5$, $Xaa^6$, $Xaa^{7a}$, and $Xaa^{7b}$ is an L-amino acid and $Xaa^4$ is a D-amino acid.

The MC1RTP may be cyclized by: (i) a lactam bridge connecting $Xaa^{2a}$ to $Xaa^{7a}$ in Formula I or connecting $Xaa^{2b}$ to $Xaa^{7b}$ in Formula II, formed by connecting the side chain of Asp, D-Asp, Glu, D-Glu, 2-Aad, or D-2-Aad with the side chain of Lys, D-Lys, Orn, D-Orn, Dab, D-Dab, Dap, or D-Dap; or (ii) a 1,2,3-triazole connecting $Xaa^{2a}$ to $Xaa^{7a}$ in Formula I or connecting $Xaa^{2b}$ to $Xaa^{7b}$ in Formula II, formed by connecting the side chains of Pra, D-Pra, Hpg, D-Hpg, Bpg or D-Bpg with Lys(N$_3$), D-Lys(N$_3$), Orn(Ns), D-Orn(Ns), Dab(Ns), D-Dab(Ns), Dap(Ns), D-Dap(Ns), 2-(5'-azidopentyl)alanine, D-2-(5'-azidopentyl)alanine, 2-(6'-azidohexyl)alanine or D-2-(6'-azidohexyl)alanine; or (iii) a disulfide bridge connecting $Xaa^{7a}$ to either $Xaa^1$ or $Xaa^{2a}$ in Formula I when $Xaa^{7a}$ is Cys and one or both of Xaa¹ and Xaa²ᵃ is Cys, or connecting Xaa⁷ᵇ to either Xaa¹ or Xaa²ᵇ in Formula II when Xaa⁷ᵇ is Cys and one or both of Xaa¹ and Xaa²ᵇ is Cys.

The MC1RTP may comprise Nle-cyclo[Asp-His-(D-Phe)-Arg-Trp-Lys], wherein the MC1RTP is optionally C-terminally amidated, and wherein 1, 2, 3 or 4 of Xaa³, Xaa⁵, Xaa⁶ and Xaa⁷ᵃ in Formula I is alpha N-methylated.

In certain embodiments, only Xaa⁵ and Xaa⁷ᵃ in Formula I are alpha N-methylated and only Xaa⁵ and Xaa⁷ᵇ in Formula II are alpha N-methylated.

The MC1RTP may be C-terminally amidated.

Without limitation, the linker may be either: a $C_1$-$C_{120}$ alkylenyl which is: linear or branched; saturated or unsaturated; and acyclic or cyclic; or a $X_1$-$X_{120}$ heteroalkylenyl, which is: linear or branched; saturated or unsaturated; and acyclic or cyclic.

Without limitation, the linker may be a linear peptide of 3 to 6 amino acid residues, -Xaa⁸-Xaa⁹-(Xaa¹⁰)$_{1-4}$-, wherein the radiolabeling group and the albumin-binding group are bonded to the free N-terminus of Xaa⁸ and the side chain of Xaa⁹, respectively, or are bonded to the side chain of Xaa⁹ and the free N-terminus of Xaa⁸, respectively; or the linker may be a branched peptide of 3 to 6 amino acid residues, -Xaa⁹(Xaa⁸)-(Xaa¹⁰)$_{1-4}$-, wherein Xaa⁹ is Lys, D-Lys, Orn, D-Orn, Dab, D-Dab, Dap or D-Dap and the C-terminus of Xaa⁸ forms an amide with the side chain of Xaa⁹, and wherein the radiolabeling group and the albumin-binding group are bonded to the free N-termini of Xaa⁸ and Xaa⁹, respectively, or are bonded to the free N-termini of Xaa⁹ and Xaa⁸, respectively.

In certain embodiments, either: the linker comprises a linear peptide, -Xaa⁸-Xaa⁹-Xaa¹⁰-, wherein the radiolabeling group and the albumin-binding group are bonded to the free N-terminus of Xaa⁸ and the side chain of Xaa⁹, respectively, or are bonded to the side chain of Xaa⁹ and the free N-terminus of Xaa⁸, respectively; or: the linker comprises a branched peptide, -Xaa⁹(Xaa⁸)-Xaa¹⁰-, wherein Xaa⁹ is Lys, D-Lys, Orn, D-Orn, Dab, D-Dab, Dap or D-Dap and the C-terminus of Xaa⁸ forms an amide with the side chain of Xaa⁹, and wherein the radiolabeling group and the albumin-binding group are bonded to the free N-termini of Xaa⁸ and Xaa⁹, respectively, or are bonded to the free N-termini of Xaa⁹ and Xaa⁸, respectively; and Xaa¹⁰ is —N(H)R²R³R²C(O)—, in which each R² is independently absent, methylene or ethylene, and R³ is —(CH$_2$)$_{1-11}$— or

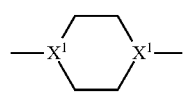

in which each X¹ is independently carbon or nitrogen. Xaa¹⁰ may be 4-amino-1-carboxymethyl-piperidine (Pip), 4-(2-aminoethyl)-1-carboxymethy 1-piperazine (Acp), or —N(H)—(CH$_2$)$_{3-15}$C(O)—.

In certain embodiments, Xaa⁸ may be Gly, Glu, D-Glu, Asp, D-Asp, 2-Aad, D-2-Aad, 3-Aad, or D-3-Aad.

In certain embodiments, the albumin-binding group may have the following structure:

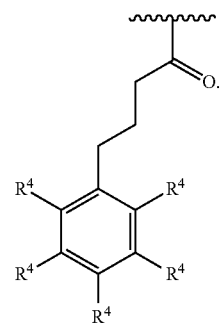

Without limitation, each R⁴ may be independently H, halogen, $C_1$-$C_5$ alkyl, $C_1$-$C_5$ alkoxyl or nitro group; and the albumin-binding group may be coupled to the α-amino group of Xaa⁸ or the side chain of Xaa⁹ when the linker comprises the linear peptide, or the albumin-binding group may be coupled to the α-amino group of Xaa⁸ or Xaa⁹ when the linker comprises the branched peptide.

In certain embodiments, the albumin-binding group may be N-[4-(p-iodophenyl)butanoyl], N-[4-(p-fluorophenyl)butanoyl], N-[4-(p-bromophenyl)butanoyl], N-[4-(p-chlorophenyl)butanoyl], or X-[4-(p-tolyl)butanoyl].

In certain embodiments, the radiolabeling group may comprise a radioisotope chelator. Without limitation, the radioisotope chelator may be selected from the group consisting of: DOTA; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; macropa; $H_2$dedpa, $H_4$octapa, $H_4$pypa, $H_4$Pypa, $H_2$azapa, $H_5$decapa, and other picolinic acid derivatives; CP256; PCTA; C-NETA; C-NE3TA; HBED; SHBED; BCPA; CP256; YM103; desferrioxamine (DFO) and DFO derivatives; and $H_6$phospa.

In certain embodiments, the radioisotope chelator may be conjugated to a radioisotope, optionally wherein the radioisotope is: $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{203}$Pb, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr, $^{114m}$In, or $^{in}$In.

Various embodiments in this disclosure relate to a compound having the following structure,

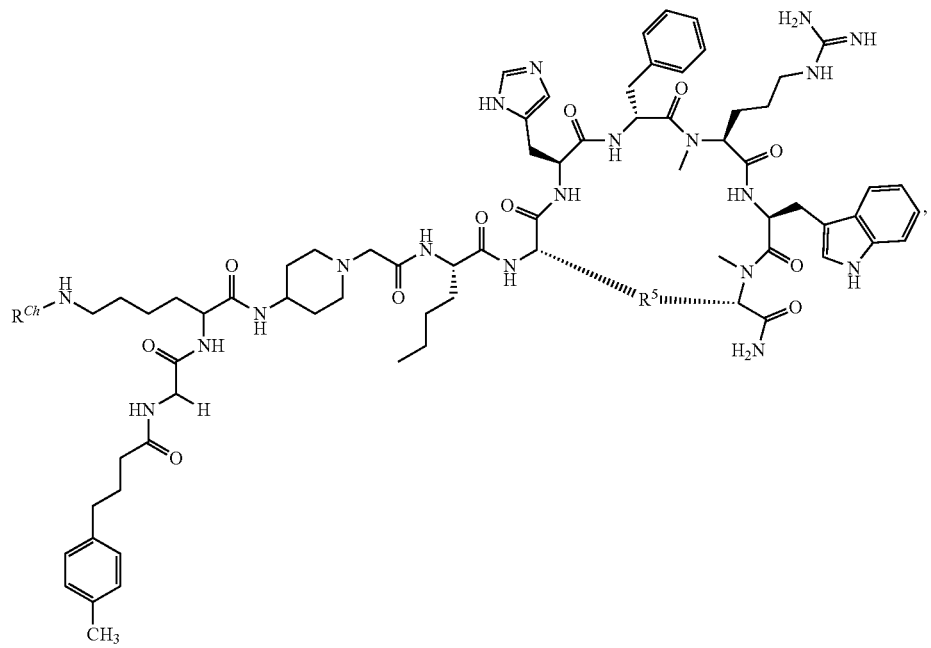

wherein $R^5$ is $-(CH_2)_{1-2}C(O)N(H)(CH_2)_{1-4}-$ or $-(CH_2)_{1-4}N(H)C(O)(CH_2)_{1-2}-$; and wherein $R^{Ch}$ is a radioisotope chelator, optionally conjugated with a radioisotope. Without limitation: the radioisotope chelator may be DOTA conjugated with $^{177}Lu$, $^{111}In$, $^{213}Bi$, $^{68}Ga$, $^{67}Ga$, $^{203}Pb$, $^{212}Pb$, $^{44}Sc$, $^{90}Y$, $^{86}Y$, $^{225}Ac$, $^{64}Cu$ or $^{67}Cu$; the radioisotope chelator may be Macropa conjugated with $^{225}Ac$; the radioisotope chelator may be Me-3,2-HOPO conjugated with $^{227}Th$; the radioisotope chelator may be $H_4py4pa$ conjugated with $^{225}Ac$ or $^{177}Lu$; the radioisotope chelator may be $H_4pypa$ conjugated with $^{177}Lu$; the radioisotope chelator may be NODAGA conjugated with $^{68}Ga$; the radioisotope chelator may be DTPA conjugated with $^{111}In$; or the radioisotope chelator may be DFO conjugated with $^{89}Zr$.

Various embodiments in this disclosure relate to a compound having the following structure, optionally conjugated with $^{177}Lu$, $^{111}In$, $^{213}Bi$, $^{68}Ga$, $^{67}Ga$, $^{203}Pb$, $^{212}Pb$, $^{44}Sc$, $^{90}Y$, $^{86}Y$, $^{64}Cu$, $^{67}Cu$ or $^{225}Ac$:

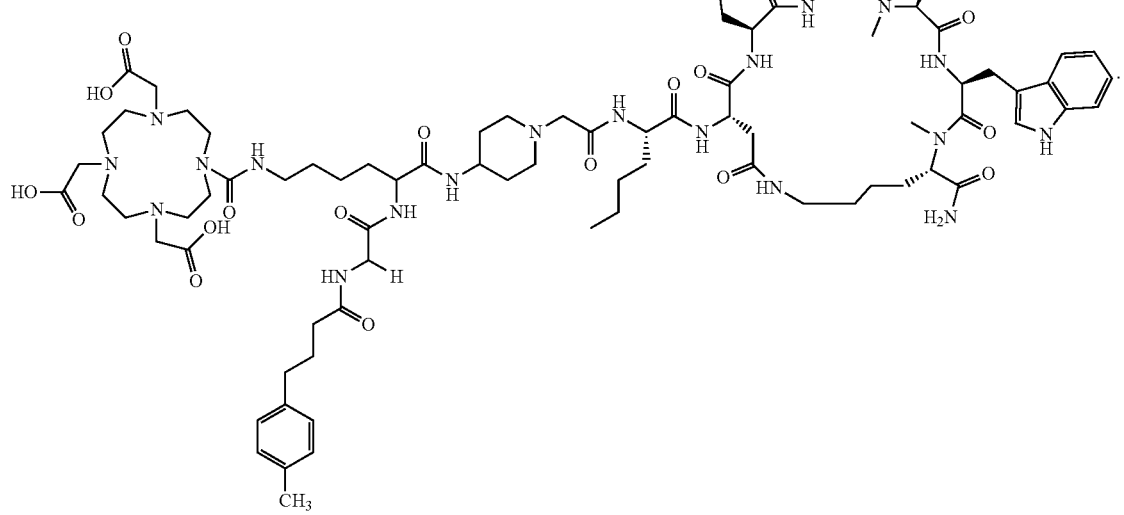

Various embodiments in this disclosure relate to a compound having the following structure, optionally conjugated with $^{225}$Ac:

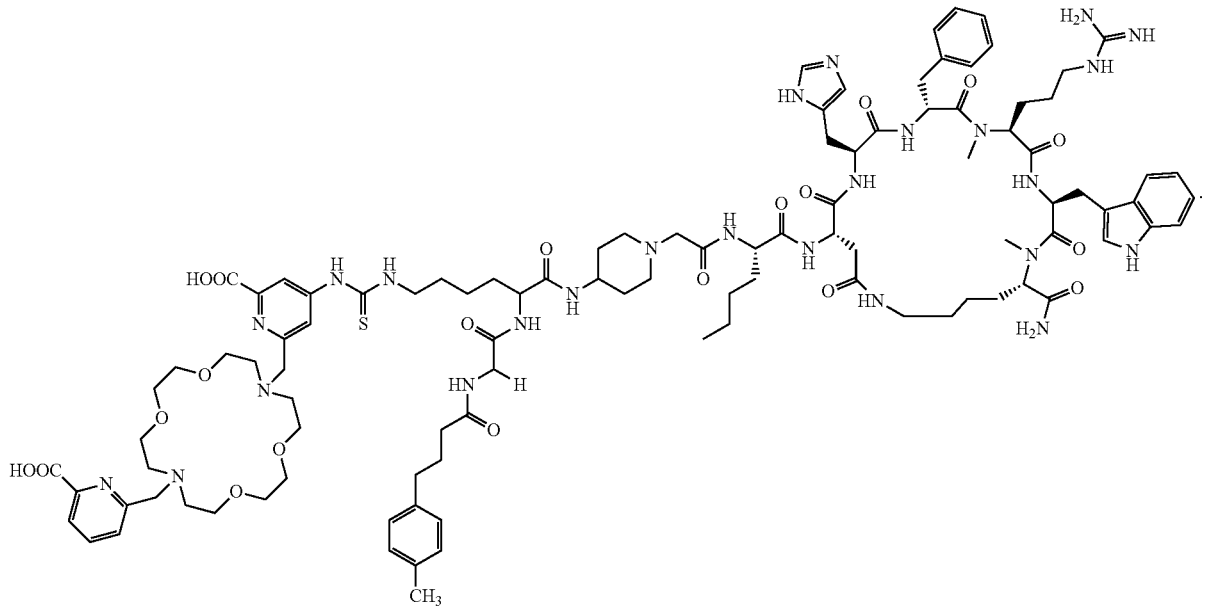 [SMILES: CCCC[C@H](NC(=O)CN1CCC(NC(=O)C(CCCCNC(=S)Nc2cc(CN3CCOCCOCCN(Cc4cccc(C(=O)O)n4)CCOCCOCC3)nc(C(=O)O)c2)NC(=O)CNC(=O)CCCc2ccc(C)cc2)CC1)C(=O)N[C@H]1CC(=O)NCCCC[C@@H](C(N)=O)N(C)C(=O)[C@H](Cc2c[nH]c3ccccc23)NC(=O)[C@H](CCCNC(=N)N)N(C)C(=O)[C@@H](Cc2ccccc2)NC(=O)[C@H](Cc2cnc[nH]2)NC1=O]

Various embodiments of the compound are for use in treating melanoma or in positron emission tomography (PET) or single photon emission computed tomography (SPECT) imaging of melanoma. In certain embodiments, the use is treating metastatic cutaneous melanoma or metastatic uveal melanoma, wherein the compound is conjugated with a therapeutic radioisotope. Without limitation, the therapeutic radioisotope is $^{64}$Cu, $^{67}$Ga, $^{111}$In, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr or $^{114m}$In. In certain embodiments, the use is PET or SPECT imaging of cutaneous or ocular melanoma, wherein the compound is conjugated with a radioisotope that is a positron emitter or a gamma emitter. Without limitation, the positron or gamma emitting radioisotope is $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{203}$Pb, $^{188}$Re, $^{186}$Re, $^{149}$Pm, $^{105}$Rh, $^{198}$Au or $^{199}$Au.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

I. General Definitions

Figure 1A:
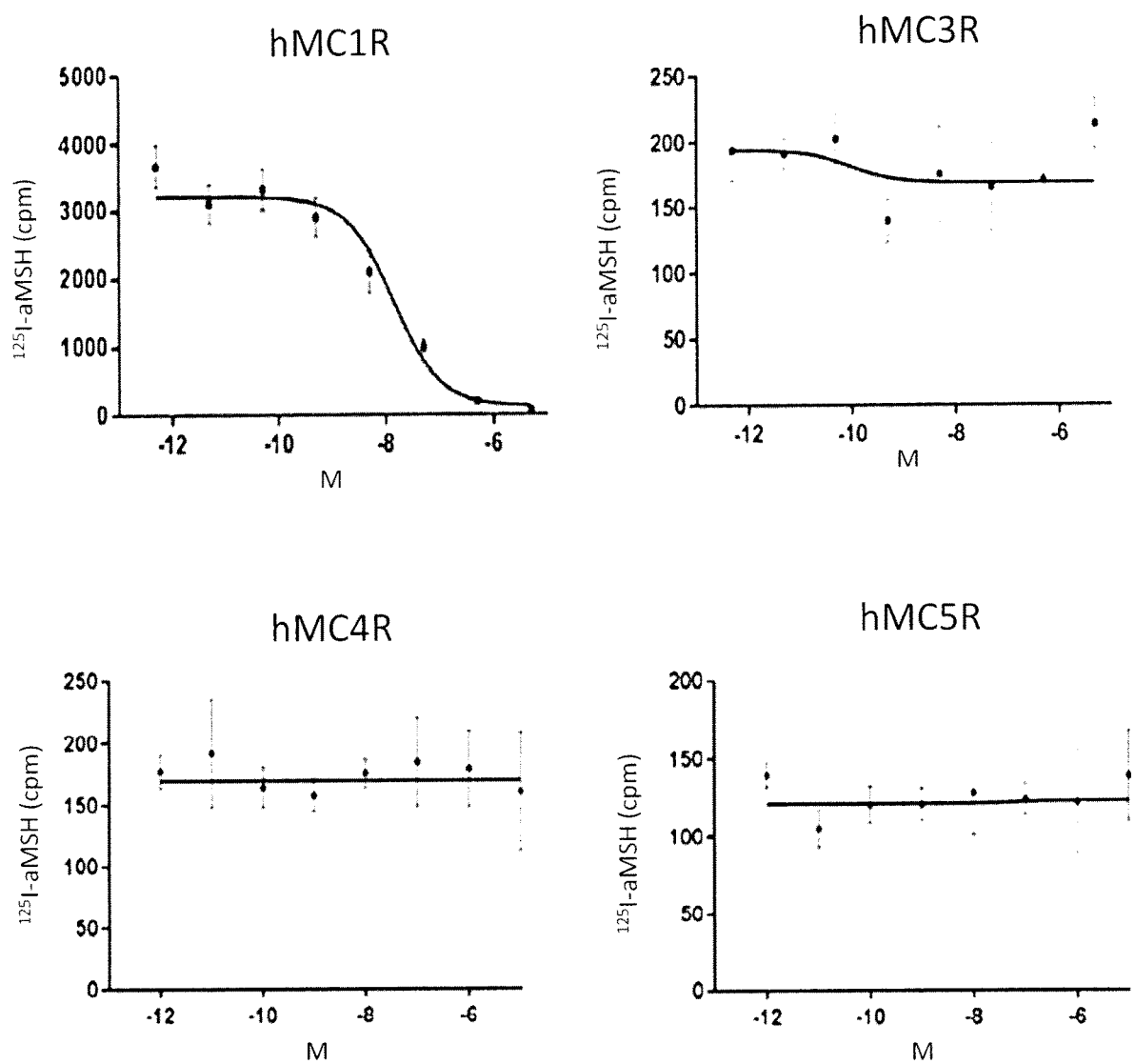
FIG. 1A shows representative competitive binding curves for compound $^{nat}$Ga-CCZ01099 in binding to hMC1R, hMC3R, hMC4R and hMC5R.

As used herein, the terms "comprising," "having", "including" and "containing," and grammatical variations thereof, are inclusive or open-ended and do not exclude additional, non-recited elements and/or method steps. The term "consisting essentially of" if used herein in connection with a compound, composition, use or method, denotes that additional elements and/or method steps may be present, but that these additions do not materially affect the manner in which the recited compound, composition, method or use functions. The term "consisting of" when used herein in connection with a composition, use or method, excludes the presence of additional elements and/or method steps. A compound, composition, use or method described herein as comprising certain elements and/or steps may also, in certain embodiments, consist essentially of those elements and/or steps, and in other embodiments consist of those elements and/or steps, whether or not these embodiments are specifically referred to. A use or method described herein as comprising certain elements and/or steps may also, in certain embodiments, consist essentially of those elements and/or steps, and in other embodiments, consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the content clearly dictates otherwise. The use of the word "a" or "an" when used herein in conjunction with the term "comprising" may mean "one," but it is also consistent with the meaning of "one or more," "at least one" and "one or more than one." The term "plurality" if used herein means more than one, for example, two or more, three or more, four or more, and the like.

In this disclosure, the recitation of numerical ranges by endpoints includes all numbers subsumed within that range including all whole numbers, all integers and, where suitable, all fractional intermediates (e.g., 1 to 5 may include 1, 1.5, 2, 2.75, 3, 3.80, 4, and 5 etc.).

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a compound, method, product, use, composition, et cetera.

The term "subject" refers to an animal (e.g. a mammal or a non-mammal animal). The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like). In some embodiments, the subject is a human.

The compounds disclosed herein may also include base-free forms, prodrugs, salts or pharmaceutically acceptable salts thereof. Unless otherwise specified, the compounds claimed and described herein are meant to include all racemic mixtures and all individual enantiomers or combinations thereof, whether or not they are explicitly represented herein.

The compounds disclosed herein may be shown as having one or more charged groups, may be shown with ionizable groups in an uncharged (e.g. protonated) state or may be shown without specifying formal charges. As will be appreciated by the person of skill in the art, the ionization state of certain groups within a compound (e.g. without limitation, $CO_2H$, $PO_3H_2$, $SO_2H$, $SO_3H$, $SO_4H$, $OPO_3H_2$ and the like) is dependent, inter alia, on the pKa of that group and the pH at that location. For example, but without limitation, a carboxylic acid group (i.e. COOH) would be understood to usually be deprotonated (and negatively charged) at neutral pH and at most physiological pH values, unless the protonated state is stabilized (e.g. due to intramolecular H-bonding). Likewise, $OSO_3H$ (i.e. $SO_4H$) groups, $SO_2H$ groups, $SO_3H$ groups, $OPO_3H_2$ (i.e. $PO_4H_2$) groups and $PO_3H$ groups would generally be deprotonated (and negatively charged) at neutral and physiological pH values.

As used herein, the terms "salt" and "solvate" have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g. without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. All zwitterions, salts, solvates and counter-ions are intended, unless a particular form is specifically indicated.

In certain embodiments, the salt or counter-ion may be pharmaceutically acceptable, e.g. for administration to a subject. More generally, with respect to any pharmaceutical composition disclosed herein, non-limiting examples of suitable excipients include any suitable buffers, stabilizing agents, salts, antioxidants, complexing agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (J. Pharm Sci. 66:1-19), or Remington—The Science and Practice of Pharmacy, 21st edition (Gennaro et al editors. Lippincott Williams & Wilkins Philadelphia).

As used herein, the expression "Xy-Xz", where y and z are integers (e.g. $X_1$-$X_{15}$, $X_1$-$X_{30}$, $X_1$-$X_{100}$, and the like), refers to the number of carbons (for alkyls and aryls, whether saturated or unsaturated) in a compound, R-group or substituent, or refers to the number of carbons and heteroatoms (for heteroalkyls and heteroaryls, whether saturated or unsaturated) in a compound, R-group or substituent. Heteroatoms may include any, some or all possible heteroatoms. For example, in some embodiments, the heteroatoms are selected from N, O, S, P and Se. In some embodiments, the heteroatoms are selected from N, O, S and P. Such embodiments are non-limiting. Alkyls and aryls may alternatively be referred to using the expression "Cy-Cz", where y and z are integers (e.g. $C_3$-$C_{15}$ and the like).

Unless explicitly stated otherwise, the terms "alkyl" and "heteroalkyl" each includes any reasonable combination of the following: (1) saturated alkyls as well as unsaturated alkyls (e.g. alkenyls and alkynyls); (2) linear or branched; (3) acyclic or cyclic (aromatic or nonaromatic), the latter of which may include multi-cyclic (fused rings, multiple non-fused rings or a combination thereof); and (4) unsubstituted or substituted. For example, an alkyl or heteroalkyl (i.e. "alkyl/heteroalkyl") may be saturated, branched and cyclic, or unsaturated, branched and cyclic, or linear and unsaturated, or any other reasonable combination according to the skill of the person of skill in the art. If unspecified, the size of the alkyl/heteroalkyl is what would be considered reasonable to the person of skill in the art. For example, but without limitation, if unspecified, the size of an alkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroalkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons and heteroatoms in length, subject to the common general knowledge of the person of skill in the art.

As used herein, in the context of an alkyl/heteroalkyl group of a compound, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl.

As used herein, a "cyclic" peptide/polypeptide may be used as it is normally understood to a person of skill in the art and generally refers to the peptide or polypeptide having a covalent bond between two amino acids within the peptide or polypeptide to form a ring structure, e.g. between carboxyl and amino termini, between carboxyl terminus and side chain amino, between amino terminus and side chain carboxyl, or between side chains. For example, but without limitation, a peptide may be cyclized by forming a lactam bridge between the side-chain carboxylate of one amino acid residue in the peptide (e.g. Asp, Glu) and the amine of another amino acid residue in the peptide (e.g. Dap, Dab, Orn, Lys). Further details are provided in Section II.

As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

As used herein, the term "saturated" when referring to a chemical entity may be used as it is normally understood to a person of skill in the art and generally refers to a chemical entity that comprises only single bonds. Non-limiting examples of a saturated $C_1$-$C_{15}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{15}$ alkenyl group may include vinyl, allyl, isopropenyl, 1-propene-2-yl, 1-butene-1-yl, 1-butene-2-yl, 1-butene-3-yl, 2-butene-1-yl, 2-butene-2-yl, octenyl and decenyl. Non-limiting examples of $C_2$-$C_{15}$ alkynyl group may include ethynyl, propynyl, butynyl, pentynyl, hexynyl, heptynyl, octynyl, nonynyl and decynyl. Without limitation, the above-defined saturated $C_1$-$C_{15}$alkyls, $C_2$-$C_{15}$ alkenyls and $C_2$-$C_{15}$ alkynyls are all encompassed within the term "$X_1$-$X_{15}$ alkyl", as used herein. Without limitation, the term "$X_1$-$X_{15}$ heteroalkyl" would encompass each of the above-defined saturated $C_1$-$C_{15}$ alkyls, $C_2$-$C_{15}$ alkenyls and $C_2$-$C_{15}$ alkynyls, where one or more of the carbon atoms is independently replaced with a heteroatom. The person of skill in the art would understand that various combinations of different heteroatoms may be used.

Unless explicitly stated otherwise, the terms "aryl" and "heteroaryl" each includes any reasonable combination of the following: (1) cyclic or multi-cyclic (fused rings, multiple non-fused rings or a combination thereof); (2) aromatic (i.e. unsaturated rings) or nonaromatic (i.e. saturated rings); and (3) unsubstituted or substituted. Non-limiting examples of aryls or heteroaryls (i.e. "aryl/heteroaryl") include: phenyl, naphthyl, thienyl, indolyl, pyridyl and the like. If unspecified, the size of the aryl/heteroaryl is what would be considered reasonable to the person of skill in the art. For example, but without limitation, if unspecified, the size of an aryl may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroaryl may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons and heteroatoms in length, subject to the common general knowledge of the person of skill in the art. It is noted that an aryl or heteroaryl may have all or only a portion of its skeleton or main chain bonded in such a way so as to form a 'loop', circle or ring of atoms bonded together. That is, the aryl/heteroaryl may comprise linear or branched chains of carbons/heteroatoms that are not part of a ring or loop.

For example, a $X_3$-$X_{18}$ aryl/heteroaryl may include, without limitation, a saturated $C_3$-$C_{18}$ cycloalkyl group, a $C_3$-$C_{18}$ cycloalkenyl group, a $C_3$-$C_{18}$ cycloalkynyl group, a $C_3$-$C_{18}$ aromatic aryl group, a $X_3$-$X_{18}$ non-aromatic heterocyclic group where each X may independently be C, N, S, P, O or Se, and a $X_3$-$X_{18}$ aromatic heterocyclic group where each X may independently be C, N, S, P, O or Se. Non-limiting examples of the saturated $C_3$-$C_{18}$ cycloalkyl group may include cyclopropanyl, cyclobutanyl, cyclopentanyl, cyclohexanyl, cycloheptanyl, cyclooctanyl, cyclononanyl and cyclodecanyl. Non-limiting examples of the $C_3$-$C_{18}$ cycloalkenyl group may include cyclopropenyl, cyclobutenyl, cyclopentenyl, cyclohexenyl, cycloheptenyl, cyclooctenyl, cyclononanenyl and cyclodecanenyl. Non-limiting examples of the $C_3$-$C_{18}$ aromatic aryl group may include phenyl (Ph), pentalenyl, indenyl, naphthyl and azulenyl. Non-limiting examples of the $X_3$-$X_{18}$ non-aromatic heterocyclic group may include aziridinyl, azetidinyl, diazetidinyl, pyrrolidinyl, pyrrolinyl, piperidinyl, piperazinyl, imidazolinyl, pyrazolidinyl, imidazolydinyl, phthalimidyl, succinimidyl, oxiranyl, tetrahydropyranyl, oxetanyl, dioxanyl, thietanyl, thiepinyl, morpholinyl, and oxathiolanyl. Non-limiting examples of the $X_3$-$X_{18}$ aromatic heterocyclic group may include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, and isoxazolyl. Unless otherwise specified, $X_1$-$X_{18}$ alkyl/heteroalkyl would encompass, among others, Xs-$X_{18}$ aryl/heteroaryl, including the groups defined above.

As used herein, the term "substituted" is used as it would normally be understood to a person of skill in the art and generally refers to a compound or chemical entity that has one chemical group replaced with a different chemical group. Unless otherwise specified, a substituted alkyl is an alkyl in which one or more hydrogen atom(s) are independently each replaced with an atom that is not hydrogen. For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. alkyl, heteroalkyl, aryl, heteroaryl and the like) may be substituted with any chemical group reasonable to the person of skill in the art. For example, but without limitation, a hydrogen bonded to a carbon or heteroatom (e.g. N) may be substituted with halide (e.g. F, I, Br, Cl), amine, amide, oxo, hydroxyl, thiol, phosphate, phosphonate, sulfate, $SO_2H$, $SO_3H$, alkyls, heteroalkyls, aryl, heteroaryl, ketones, carboxaldehyde, carboxylates, carboxamides, nitriles, monohalomethyl, dihalomethyl or trihalomethyl.

As used herein, the term "unsubstituted" is used as it would normally be understood to a person of skill in the art. Non-limiting examples of unsubstituted alkyls include methyl, ethyl, tert-butyl, pentyl and the like. The expression "optionally substituted" is used interchangeably with the expression "unsubstituted or substituted".

In the structures provided herein, hydrogen may or may not be shown. In some embodiments, hydrogens (whether shown or implicit) may be protium (i.e. $^1H$), deuterium (i.e. $^2H$) or combinations of $^1H$ and $^2H$. Methods for exchanging $^1H$ with $^2H$ are well known in the art. For solvent-exchangeable hydrogens, the exchange of $^1H$ with $^2H$ occurs readily in the presence of a suitable deuterium source, without any catalyst. The use of acid, base or metal catalysts, coupled with conditions of increased temperature and pressure, can facilitate the exchange of non-exchangeable hydrogen atoms, generally resulting in the exchange of all $^1H$ to $^2H$ in a molecule.

Unless otherwise specified a "peptide" as referred to herein may comprise proteinogenic and/or non-proteinogenic amino acid residues. Non-limiting examples of non-proteinogenic amino acids include: D-amino acids (including without limitation any D-form of the following amino acids), ornithine (Orn), 3-(1-naphtyl)alanine (Nal), 3-(2-naphtyl)alanine (2-Nal), α-aminobutryic acid, norvaline, norleucine (Nle), homonorleucine, beta-(1,2,3-triazol-4-yl)-L-alanine, 1,2,4-triazole-3-alanine, Phe(4-F), Phe(4-Cl), Phe(4-Br), Phe(4-I), Phe(4-$NH_2$), Phe(4-$NO_2$), homoarginine (hArg), 2-amino-4-guanidinobutyric acid (Agb), 2-amino-3-guanidinopropionic acid (Agp), Trp(5-Br), Trp (5-$OCH_3$), Trp(6-F), Trp(5-OH) or Trp(CHO), 2-aminoadipic acid (2-Aad), 3-aminoadipic acid (3-Aad), propargylglycine (Pra), homopropargylglycine (Hpg), beta-homopropargylglycine (Bpg), 2,3-diaminopropionic acid (Dap), 2,4-diaminobutyric acid (Dab), azidolysine (Lys($N_3$)), azido-ornithine (Orn($N_3$)), 2-amino-4-azidobutanoic acid Dab($N_3$). Dap($N_3$). 2-(5'-azidopentyl)alanine, 2-(6'-azidohexyl)alanine, 4-amino-1-carboxymethyl-piperidine (Pip), 4-(2-aminoethyl)-1-carboxymethyl-piperazine (Acp).

If not specified as an L- or D-amino acid, an amino acid shall be understood to be an L-amino acid.

Unless otherwise specified, amino acids may be modified by any modifications known in the art subject to the common general knowledge of the person of skill in the art. For example, but without limitation, a C-terminal amino acid residue may be amidated, which refers to replacement of the C-terminal carboxylate with an amide, i.e. —C(O)$NH_2$ instead of —C(O)OH. Amidated residues are identified with —$NH_2$ (e.g. Lys-$NH_2$, Trp-$NH_2$ and the like). As a further non-limiting example, amino acids may be methylated, e.g. N-methylated or alpha N-methylated.

The term "Xaa" refers to any amino acid. The term "-$Xaa^8$-$Xaa^9$-$Xaa^{10}$-" refers to three amino acids, $Xaa^8$, $Xaa^9$, and $Xaa^{10}$ chained together with peptide bonds. The term "-$Xaa^9$($Xaa^8$)-$Xaa^{10}$-" refers to the same three amino acids, but chained together with an amide bond between the C-terminus of $Xaa^9$ and the N-terminus of $Xaa^{10}$ with a further amide bond formed between the C-terminus of $Xaa^8$ and the side chain amine of $Xaa^9$. Unless otherwise indicated, "Xaa" may be any amino acid commonly known to the person of skill in the art, including proteinogenic and nonproteinogenic amino acids (e.g. but not limited to the nonproteinogenic amino acids listed above).

For cyclized peptides, the formula $Xaa^1$-cyclo($Xaa^2$-$Xaa^3$-$Xaa^4$)-$Xaa^5$ and the like, refers to a covalent linkage between the side chains of $Xaa^2$ and $Xaa^4$ (i.e. between the first and last amino acids in the parentheses). Similarly, the formula $Xaa^1$-cyclo($Xaa^2$-$Xaa^3$-$Xaa^4$-$Xaa^5$) refers to a cyclized peptide having a covalent linkage between the side chains of $Xaa^2$ and $Xaa^5$.

II. Compounds

The compounds presented herein incorporate peptides, which may be synthesized by any of a variety of methods established in the art. This includes but is not limited to liquid-phase as well as solid-phase peptide synthesis using methods employing 9-fluorenylmethoxycarbonyl (Fmoc) and/or t-butyloxycarbonyl (Boc) chemistries, and other synthetic approaches.

Solid-phase peptide synthesis methods and technology are well-established in the art. For example, peptides may be synthesized by sequential incorporation of the amino acid residues of interest one at a time. In such methods, peptide synthesis is typically initiated by attaching the C-terminal amino acid of the peptide of interest to a suitable resin. Prior to this, reactive side chain and alpha amino groups of the amino acids are protected from reaction by suitable protecting groups, allowing only the alpha carboxyl group to react with a functional group such as an amine group, a hydroxyl group, or an alkyl halide group on the solid support. Following coupling of the C-terminal amino acid to the support, the protecting group on the side chain and/or the alpha amino group of the amino acid is selectively removed, allowing the coupling of the next amino acid of interest. This process is repeated until the desired peptide is fully synthesized, at which point the peptide can be cleaved from the support and purified. A non-limiting example of an instrument for solid-phase peptide synthesis is the Aapptec Endeavor 90 peptide synthesizer.

The choice of resin determines whether the peptide will have either a C-terminal carboxylate or a C-terminal amide (i.e. whether or not the C-terminus of the peptide is amidated). For example, but without limitation, 4-(2',4'-Dimethoxyphenyl-Fmoc-aminomethyl)phenoxy resin (Rink Amide Resin) or 9-Fmoc-aminoxanthen-3-yloxy-Merrifield resin (Sieber Amide resin) may be used for a C-terminal amide once the peptide is cleaved. Without limitation, p-benzyloxybenzyl alcohol resin (Wang resin) or 2-chlorotrityl chloride resin may be used for a C-terminal carboxylate once the peptide is cleaved. During use, the resin is swelled in solvents, such as N,N-dimethylformamide (DMF), dichloromethane (DCM) or 1-methyl-2-pyrrolidone (NMP), and the like.

To allow coupling of additional amino acids, Fmoc protecting groups may be removed from the amino acid on the solid support, e.g. under mild basic conditions, such as piperidine (20-50% v/v) in DMF. The amino acid to be added must also have been activated for coupling (e.g. at the alpha carboxylate). Non-limiting examples of activating reagents include without limitation 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(7-Aza-1H-benzotriazole-1-yl)-1,1,3,3-tetramethyluronium hexafluorophosphate (HATU), benzotriazole-1-yl-oxy-tris(dimethylamino)phosphoniumhexafluorophosphate (BOP), benzotriazole-1-yl-oxy-tris(pyrrolidino)phosphoniumhexafluorophosphate (PyBOP). Racemization is minimized by using triazoles, such as 1-hydroxy-benzotriazole (HOBt) and 1-hydroxy-7-azabenzotriazole (HOAt). Coupling may be performed in the presence of a suitable base, such as N,N-diisopropylethylamine (DIPEA/DIEA) and the like. For long peptides, peptide synthesis and ligation may be used.

Cyclization of the peptide may be performed by any known method. Cyclization may be performed on-resin or off-resin. Non-limiting examples of peptide cyclization include: forming a lactam bridge between an amino acid side chain containing a carboxyl group (e.g. Asp, D-Asp, Glu, D-Glu, and the like) and an amino acid side chain containing an amino group (e.g. Lys, D-Lys, Orn, D-Orn, Dab, D-Dab, Dap, D-Dap, and the like); forming a 1,2,3-triazole via click chemistry between an amino acid side chain containing an azide group (e.g. Lys($N_3$), D-Lys($N_3$), and the like) and an alkyne group (e.g. Pra, D-Pra, and the like); and forming a disulfide bridge between side chains of Cys residues. Since cyclization occurs between amino acid side chains, the protecting groups on these amino acids must be selectively removed before cyclization except the reaction between an alkyne and an azido groups via the click reaction to form an 1,2,3-triazole. Non-limiting examples of selectively removable protecting groups include acetaminomethyl (Acm) (e.g. on Cys), 2-phenylisopropyl esters (O-2-PhiPr) (e.g. on Asp/Glu) as well as 4-methyltrityl (Mtt), allyloxycarbonyl (alloc), 1-(4,4-dimethyl-2,6-dioxocyclohex-1-ylidene))ethyl (Dde), and 1-(4,4-dimethyl-2,6-dioxocyclohex-1-ylidene)-3-methylbutyl (ivDde) (e.g. on Lys/Orn/Dab/Dap). The Acm group on Cys can be selectively removed by 2 eq. of thallium (III) trifluoroacetate in DMF, which simultaneously induces cyclization via the formation of the disulfide bridge. O-2-PhiPr and Mtt protecting groups can be selectively deprotected under mild acidic conditions, such as 2.5% trifluoroacetic acid (TFA) in DCM. Alloc protecting groups can be selectively deprotected using tetrakis(triphenylphosphine)palladium(O) and phenyl silane in DCM. Dde and ivDde protecting groups can be selectively deprotected using 2-5% of hydrazine in DMF. Deprotected side chains of Asp/Glu (L- or D-forms) and Lys/Orn/Dab/Dap (L- or D-forms) can then be cyclized, e.g. by using the coupling reaction conditions described above.

Peptide backbone amides may be N-methylated (i.e. alpha amino methylated). This may be achieved by directly using Fmoc-N-methylated amino acids during peptide synthesis. Alternatively, N-methylation under Mitsunobu conditions may be performed. First, a free primary amine group is protected using a solution of 4-nitrobenzenesulfonyl chloride (Ns-Cl) and 2,4,6-trimethylpyridine (collidine) in NMP. N-methylation may then be achieved in the presence of triphenylphosphine, diisopropyl azodicarboxylate (DIAD) and methanol. Subsequently, N-deprotection may be performed using mercaptoethanol and 1,8-diazabicyclo[5.4.0]undec-7-ene (DBU) in NMP. For coupling protected amino acids to N-methylated alpha amino groups, HATU, HOAt and DIEA may be used.

As described further below, chelators, linkers (peptide or non-peptide linkers) and/or albumin-binding groups may be coupled to the peptide N-terminus while the peptide is attached to the solid support. This is facile when the chelator, linker and/or albumin-binding groups comprise an activated carboxylate (and protected groups if necessary) so that coupling can be performed on resin.

When the peptide has been fully synthesized on the solid support, the desired peptide may be cleaved from the solid support using suitable reagents, such as TFA, tri-isopropylsilane (TIS) and water. Side chain protecting groups, such as Boc, pentamethyldihydrobenzofuran-5-sulfonyl (Pbf), trityl (Trt) and tert-butyl (tBu) are simultaneously removed (i.e. deprotection). The crude peptide may be precipitated and collected from the solution by adding cold ether followed by centrifugation. Purification and characterization of the peptides may be performed by standard separation techniques, such as high performance liquid chromatography (HPLC) based on the size, charge and polarity of the peptides. The identity of the purified peptides may be confirmed by mass spectrometry or other similar approaches.

The present disclosure provides a compound comprising a melanocortin 1 receptor (MC1R) targeting peptide (MC1RTP), a radiolabeling group, and a linker joining the MC1RTP to the radiolabeling group. One or more amino acid residues of the MC1RTP is alpha N-methylated. The linker comprises an albumin-binding group.

The MC1RTP binds MC1R under physiological conditions (e.g. in vivo), and in some embodiments is selective for MC1R over at least one other member of melanocortin receptor (i.e. MC3R, MC4R and/or MC5R). The MC1RTP may be selective for MC1R over MC3R. The MC1RTP may be selective for MC1R over MC4R. The MC1RTP may be selective for MC1R over MC5R. The MC1RTP may be selective for MC1R over any combination of MC3R, MC4R and/or MC5R. The MC1RTP may be selective for MC1R over MC3R, MC4R and MC5R.

The MC1RTP comprises an amino acid sequence defined by Formula I or Formula II:

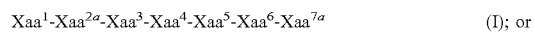

$$Xaa^1\text{-}Xaa^{2a}\text{-}Xaa^3\text{-}Xaa^4\text{-}Xaa^5\text{-}Xaa^6\text{-}Xaa^{7a} \qquad (I); or$$

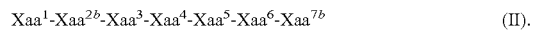

$$Xaa^1\text{-}Xaa^{2b}\text{-}Xaa^3\text{-}Xaa^4\text{-}Xaa^5\text{-}Xaa^6\text{-}Xaa^{7b} \qquad (II).$$

$Xaa^1$ is norleucine (Nle), D-Nle, Ala, D-Ala, Leu, D-Leu, Ile, D-Ile, Cys, D-Cys, Met, D-Met, Phe, D-Phe, Trp, D-Trp, Val, D-Val, 3-(1-naphtyl)alanine (Nal), D-Nal, 3-(2-naphtyl)

alanine (2-Nal), D-2-Nal, Gly, α-aminobutryic acid, D-α-aminobutryic acid, norvaline, D-norvaline, homonorleucine, or D-homonorleucine. In some embodiments, $Xaa^1$ is Nle, Ala, Leu, lie, Cys, Met, Phe, Trp, Val, Nal, 2-Nal, Gly, α-aminobutryic acid, norvaline or homonorleucine. In some embodiments, $Xaa^1$ is Nle, Ala, Leu, He, Cys, Met, Phe, Trp, Val, Nal, 2-Nal, α-aminobutryic acid, norvaline or homonorleucine. In some embodiments, $Xaa^1$ is Nle.

$Xaa^{2a}$ is Cys, D-Cys, Asp, D-Asp, Glu, D-Glu, 2-aminoadipic acid (2-Aad), D-2-Aad, 3-aminoadipic acid (3-Aad), D-3-Aad, propargylglycine (Pra), D-Pra, homopropargylglycine (Hpg), D-Hpg, beta-homopropargylglycine (Bpg) or D-Bpg. In some embodiments, $Xaa^{7b}$ is Cys, Asp, Glu, 2-Aad, 3-Aad, Pra, Hpg, or Bpg. In some embodiments, $Xaa^{2a}$ is Asp, Glu, Pra or D-Pra. In some embodiments, $Xaa^{2a}$ is Asp, Glu, or Pra. In some embodiments, $Xaa^{2a}$ is Asp.

$Xaa^{2b}$ is Cys, D-Cys, Lys, D-Lys, Ornithine (Om), D-Om, 2,4-diaminobutyric acid (Dab), D-Dab, 2,3-diaminopropionic acid (Dap), D-Dap, $Lys(N_3)$, $D-Lys(N_3)$, Orn(Ns), D-Orn(Ns), Dab(Ns), D-Dab(Ns), Dap(Ns), D-Dap(Ns), 2-(5'-azidopentyl)alanine, D-2-(5'-azidopentyl)alanine, 2-(6'-azidohexyl)alanine or D-2-(6'-azidohexyl)alanine. In some embodiments, $Xaa^{2b}$ is Cys, Lys, Orn, Dab, Dap, $Lys(N_3)$, $Orn(N_3)$, $Dab(N_3)$, $Dap(N_3)$, or 2-(5'-azidopentyl)alanine, 2-(6'-azidohexyl)alanine. In some embodiments, $Xaa^{2b}$ is Lys Orn, Dab, Dap, $Lys(N_3)$, $Orn(N_3)$, $Dab(N_3)$, $Dap(N_3)$, 2-(5'-azidopentyl)alanine, or 2-(6'-azidohexyl)alanine. In some embodiments, $Xaa^{2b}$ is Lys.

$Xaa^3$ is His, D-His, Pro, beta-(1,2,3-triazol-4-yl)-DL-alanine, beta-(1,2,3-triazol-4-yl)-L-alanine, beta-(1,2,3-triazol-4-yl)-D-alanine, 1,2,4-triazole-3-alanine, or 1,2,4-triazole-3-D-alanine. In some embodiments, $Xaa^3$ is His, Pro, beta-(1,2,3-triazol-4-yl)-L-alanine, or 1,2,4-triazole-3-alanine. In some embodiments, $Xaa^3$ is His, beta-(1,2,3-triazol-4-yl)-DL-alanine, or 1,2,4-triazole-3-alanine. In some embodiments, $Xaa^3$ is His.

$Xaa^4$ is Phe, D-Phe, 2-Nal, D-2-Nal, Phe(4-F), D-Phe(4-F), Phe(4-Cl), D-Phe(4-Cl), Phe(4-Br), D-Phe(4-Br), Phe(4-I), D-Phe(4-I), $Phe(4-NH_2)$, $D-Phe(4-NH_2)$, $Phe(4-NO_2)$, or $D-Phe(4-NO_2)$. In some embodiments, $Xaa^4$ is D-Phe, D-2-Nal, D-Phe(4-F), D-Phe(4-Cl), D-Phe(4-Br), D-Phe(4-I), $D-Phe(4-NH_2)$, or $D-Phe(4-NO_2)$. In some embodiments, $Xaa^4$ is Phe, D-Phe, 2-Nal or D-2-Nal. In some embodiments, $Xaa^4$ is D-Phe or D-2-Nal. In some embodiments, $Xaa^4$ is D-Phe.

$Xaa^5$ is Arg, D-Arg, homoarginine (hArg), D-hArg, Leu, D-Leu, 2-amino-4-guanidinobutyric acid (Agb), D-Agb, 2-amino-3-guanidinopropionic acid (Agp), or D-Agp. In some embodiments, $Xaa^5$ is Arg, D-Arg, hArg, Leu, D-hArg, Agb, D-Agb, Agp or D-Agp. In some embodiments, $Xaa^5$ is Arg, hArg, Leu, Agb, or Agp. In some embodiments, $Xaa^5$ is Arg.

$Xaa^6$ is Phe, D-Phe, Trp, D-Trp, Trp(5-Br), D-Trp(5-Br), $Trp(5-OCH_3)$, $D-Trp(5-OCH_3)$, Trp(6-F), D-Trp(6-F), Trp(5-OH), D-Trp(5-OH), Trp(CHO), or D-Trp(CHO). In some embodiments, $Xaa^6$ is Phe, Trp, Trp(5-Br), $Trp(5-OCH_3)$, Trp(6-F), Trp(5-OH), or Trp(CHO). In some embodiments, $Xaa^6$ is Trp or D-Trp. In some embodiments, $Xaa^6$ is Trp.

$Xaa^{7a}$ is Cys, D-Cys, Lys, D-Lys, Orn, D-Om, Dab, D-Dab, Dap, D-Dap, Lys(Ns), D-Lys(Ns), Orn(Ns), D-Orn (Ns), Dab(Ns), D-Dab(Ns), Dap(Ns), D-Dap(Ns), 2-(5'-azidopentyl)alanine, D-2-(5'-azidopentyl)alanine, 2-(6'-azidohexyl)alanine or D-2-(6'-azidohexyl)alanine. In some embodiments, $Xaa^{7a}$ is Cys, Lys, Orn, Dab, Dap, $Lys(N_3)$, $Orn(N_3)$, $Dab(N_3)$, $Dap(N_3)$, 2-(5'-azidopentyl)alanine, or 2-(6'-azidohexyl)alanine. In some embodiments, $Xaa^{7a}$ is Lys Orn, Dab, Dap, $Lys(N_3)$, $Orn(N_3)$, $Dab(N_3)$, $Dap(N_3)$, 2-(5'-azidopentyl)alanine, or 2-(6'-azidohexyl)alanine. In some embodiments, $Xaa^{7a}$ is Lys.

$Xaa^{7b}$ is Cys, D-Cys, Asp, D-Asp, Glu, D-Glu, 2-Aad, D-2-Aad, 3-Aad, D-3-Aad, Pra, D-Pra, Hpg, D-Hpg, Bpg or D-Bpg. In some embodiments, $Xaa^{7b}$ is Cys, Asp, Glu, 2-Aad, 3-Aad, Pra, Hpg, or Bpg. In some embodiments, $Xaa^{7b}$ is Asp, Glu, Pra or D-Pra. In some embodiments, $Xaa^{7b}$ is Asp.

In some embodiments, each of $Xaa^1$, $Xaa^{2a}$, $Xaa^{2b}$, $Xaa^3$, $Xaa^5$, $Xaa^6$, $Xaa^{7a}$, and $Xaa^{7b}$ are L-amino acids and $Xaa^4$ is a D-amino acid.

In some embodiments, the sequence of the MC1RTP consists essentially of the sequence defined by Formula I or II, wherein $Xaa^1$, $Xaa^{2a}$, $Xaa^{2b}$, $Xaa^3$, $Xaa^4$, $Xaa^5$, $Xaa^6$, $Xaa^{7a}$, and $Xaa^{7b}$ are as defined for any combination of embodiments defined in this disclosure. In some embodiments, the sequence of the MC1RTP consists of the sequence defined by Formula I or II, wherein $Xaa^1$, $Xaa^{2a}$, $Xaa^{2b}$, $Xaa^3$, $Xaa^4$, $Xaa^5$, $Xaa^6$, $Xaa^{7a}$, and $Xaa^{7b}$ are as defined for any combination of embodiments defined in this disclosure. In some embodiments, the sequence of the MC1RTP comprises, consists or consists essentially of the sequence defined by Formula I, wherein $Xaa^1$, $Xaa^{2a}$, $Xaa^3$, $Xaa^4$, $Xaa^5$, $Xaa^6$, and $Xaa^{7a}$ are as defined for any combination of embodiments defined in this disclosure. In some embodiments, the sequence of the MC1RTP comprises, consists or consists essentially of the sequence defined by Formula II, wherein $Xaa^1$, $Xaa^{2b}$, $Xaa^3$, $Xaa^4$, $Xaa^5$, $Xaa^6$, and $Xaa^{7b}$ are as defined for any combination of embodiments defined in this disclosure.

In some embodiments, the sequence of MC1RTP comprises, consists or consists essentially of the sequence defined by Formula I, wherein: $Xaa^1$ is Nle, Ala, Leu, lie, Cys, Met, Phe, Trp, Val, Nal, 2-Nal, α-aminobutryic acid, norvaline or homonorleucine; $Xaa^{2a}$ is Asp, Glu, Pra or D-Pra; $Xaa^3$ is His, beta-(1,2,3-triazol-4-yl)-DL-alanine, or 1,2,4-triazole-3-alanine; $Xaa^4$ is Phe, D-Phe, 2-Nal or D-2-Nal; $Xaa^5$ is Arg, D-Arg, hArg, Leu, D-hArg, Agb, D-Agb, Agp or D-Agp; $Xaa^6$ is Trp or D-Trp; and $Xaa^{7a}$ is Lys Orn, Dab, Dap, $Lys(N_3)$, $Orn(N_3)$, $Dab(N_3)$, $Dap(N_3)$, 2-(5'-azidopentyl)alanine, or 2-(6'-azidohexyl)alanine.

In some embodiments, $Xaa^1$ is Nle, $Xaa^{2a}$ is Asp, $Xaa^3$ is His, $Xaa^4$ is D-Phe, $Xaa^5$ is Arg, $Xaa^6$ is Trp and $Xaa^7$ is Lys. The sequence of MC1RTP may consist essentially of Nle-Asp-His-(D-Phe)-Arg-Trp-Lys, linear or cyclic, optionally C-terminally amidated, and alpha N-methylated as elsewhere defined in this disclosure. The sequence of MC1RTP may consist of Nle-Asp-His-(D-Phe)-Arg-Trp-Lys, linear or cyclic, optionally C-terminally amidated, and alpha N-methylated as elsewhere defined in this disclosure.

The MC1RTP may or may not be C-terminally amidated (e.g. at $Xaa^{7a}$ or $Xaa^{7b}$). In some embodiments, the MC1RTP is C-terminally amidated. In some embodiments, the MC1RTP has a C-terminal carboxylate.

One or more amino acid residues of the MC1RTP is alpha N-methylated, including N-methylation of 1, 2, 3 or 4 of $Xaa^3$, $Xaa^5$, $Xaa^6$ and $Xaa^{7a}$ in the sequence defined by Formula I and/or 1, 2, 3 or 4 of $Xaa^3$, $Xaa^5$, $Xaa^6$ and $Xaa^{7b}$ in the sequence defined by Formula II. In some embodiments, the MC1RTP has only 1, only 2, only 3 or only 4 alpha N-methylations. In some embodiments, $Xaa^5$ and $Xaa^{7a}$ in the sequence defined by Formula I are alpha N-methylated. In some embodiments, $Xaa^5$ and $Xaa^{7b}$ in the sequence defined by Formula II are alpha N-methylated. In some embodiments, the N-methylations are (N-Me-$Xaa^3$), (N-Me-$Xaa^5$), (N-Me-$Xaa^6$) and (N-Me-$Xaa^{7a}$). In some embodiments, the N-methylations are (N-Me-Xaa$^3$), (N-Me-Xaa$^5$), (N-Me-Xaa$^6$) and (N-Me-Xaa$^{7b}$). In some embodiments, the N-methylations are (N-Me-Xaa$^5$), (N-Me-Xaa$^6$) and (N-Me-Xaa$^{7a}$). In some embodiments, the N-methylations are (N-Me-Xaa$^5$), (N-Me-Xaa$^6$) and (N-Me-Xaa$^{7b}$). In some embodiments, the N-methylations are (N-Me-Xaa$^5$) and (N-Me-Xaa$^6$). In some embodiments, the N-methylations are (N-Me-Xaa$^6$) and (N-Me-Xaa$^{7a}$). In some embodiments, the N-methylations are (N-Me-Xaa$^6$) and (N-Me-Xaa$^{7b}$). In some embodiments, the N-methylations are (N-Me-Xaa$^5$) and (N-Me-Xaa$^{7a}$). In some embodiments, the N-methylations are (N-Me-Xaa$^5$) and (N-Me-Xaa$^{7b}$). In some embodiments, the only N-methylation is (N-Me-Xaa$^6$).

In some embodiments, the MC1RTP is linear. In some embodiments, the MC1RTP is cyclized. In some embodiments, the MC1RTP comprises, consists or consists essentially of Xaa$^1$-cyclo[Xaa$^{2a}$-Xaa$^3$-Xaa$^4$-Xaa$^5$-Xaa$^6$-Xaa$^{7a}$]. In some embodiments, the MC1RTP comprises, consists or consists essentially of cyclo[Xaa$^1$-Xaa$^{2a}$-Xaa$^3$-Xaa$^4$-Xaa$^5$-Xaa$^6$-Xaa$^{7a}$]. In some embodiments, the MC1RTP comprises, consists or consists essentially of Xaa$^1$-cyclo[Xaa$^{2b}$-Xaa$^3$-Xaa$^4$-Xaa$^5$-Xaa$^6$-Xaa$^{7b}$]. In some embodiments, the MC1RTP comprises, consists or consists essentially of cyclo [Xaa$^1$-Xaa$^{2a}$-Xaa$^3$-Xaa$^4$-Xaa$^5$-Xaa$^6$-Xaa$^{7b}$]. In the foregoing sequences, Xaa$^1$, Xaa$^{2a}$, Xaa$^{2b}$, Xaa$^3$, Xaa$^4$, Xaa$^5$, Xaa$^6$, Xaa$^{7a}$, Xaa$^{7b}$ may have any of the alternative definitions presented in the paragraphs above or elsewhere in this disclosure.

The MC1RTP may be cyclized by a lactam bridge connecting Xaa$^{2a}$ to Xaa$^{7a}$ in the sequence defined by Formula I, formed by connecting the side chain of Asp, D-Asp, Glu, D-Glu, 2-Aad, or D-2-Aad with the side chain of Lys, D-Lys, Orn, D-Orn, Dab, D-Dab, Dap, or D-Dap. The MC1RTP may be cyclized by a lactam bridge connecting Xaa$^{2b}$ to Xaa$^{7b}$ in the sequence defined by Formula II, formed by connecting the side chain of Asp, D-Asp, Glu, D-Glu, 2-Aad, or D-2-Aad with the side chain of Lys, D-Lys, Orn, D-Orn, Dab, D-Dab, Dap, or D-Dap.

The MC1RTP may be cyclized by a 1,2,3-triazole connecting Xaa$^{2a}$ to Xaa$^{7a}$ in the sequence defined by Formula I, formed by connecting the side chains of Pra, D-Pra, Hpg, D-Hpg, Bpg or D-Bpg with Lys(N$_3$), D-Lys(N$_3$), Orn(N$_3$), D-Orn(N$_3$), Dab(N$_3$), D-Dab(N$_3$), Dap(N$_3$), D-Dap(N$_3$), 2-(5'-azidopentyl)alanine, D-2-(5'-azidopentyl)alanine, 2-(6'-azidohexyl)alanine or D-2-(6'-azidohexyl)alanine. The MC1RTP may be cyclized by a 1,2,3-triazole connecting Xaa$^{2b}$ to Xaa$^{7b}$ in the sequence defined by Formula II, formed by connecting the side chains of Pra, D-Pra, Hpg, D-Hpg, Bpg or D-Bpg with Lys(N$_3$), D-Lys(N$_3$), Orn(N$_3$), D-Orn(N$_3$), Dab(N$_3$), D-Dab(N$_3$), Dap(N$_3$), D-Dap(N$_3$), 2-(5'-azidopentyl)alanine, D-2-(5'-azidopentyl)alanine, 2-(6'-azidohexyl)alanine or D-2-(6'-azidohexyl)alanine.

The MC1RTP may be cyclized by a disulfide bridge connecting Xaa$^1$ to Xaa$^{7a}$ in the sequence defined by Formula I when both Xaa$^1$ and Xaa$^{7a}$ are Cys (D- and/or L-form). The MC1RTP may be cyclized by a disulfide bridge connecting Xaa$^{2a}$ to Xaa$^{7a}$ in the sequence defined by Formula I when both Xaa$^{2a}$ and Xaa$^{7a}$ are Cys (D- and/or L-form). The MC1RTP may be cyclized by a disulfide bridge connecting Xaa$^1$ to Xaa$^{7b}$ in the sequence defined by Formula II when both Xaa$^1$ and Xaa$^{7b}$ and are Cys (D- or L-form). The MC1RTP may be cyclized by a disulfide bridge connecting Xaa$^{2b}$ to Xaa$^{7b}$ in the sequence defined by Formula II when both Xaa$^{2b}$ and Xaa$^{7b}$ and are Cys (D- or L-form).

In some embodiments, the MC1RTP may comprise, consist or consist essentially of:
Xaa$^1$-cyclo[Xaa$^{2a}$-Xaa$^3$-Xaa$^4$-(N-Me-Xaa$^5$)-(N-Me-Xaa$^6$)-(N-Me-Xaa$^{7a}$)]—NH$_2$;
Xaa$^1$-cyclo[Xaa$^{2a}$-Xaa$^3$-Xaa$^4$-(N-Me-Xaa$^5$)-(N-Me-Xaa$^6$)-Xaa$^{7a}$]-NH$_2$;
Xaa$^1$-cyclo[Xaa$^{2a}$-Xaa$^3$-Xaa$^4$-Xaa$^5$-(N-Me-Xaa$^6$)-(N-Me-Xaa$^{7a}$)]—NH$_2$;
Xaa$^1$-cyclo[Xaa$^{2a}$-Xaa$^3$-Xaa$^4$-(N-Me-Xaa$^5$)-Xaa$^6$-(N-Me-Xaa$^{7a}$)]—NH$_2$;
Xaa$^1$-cyclo[Xaa$^{2a}$-Xaa$^3$-Xaa$^4$-(N-Me-Xaa$^5$)-Xaa$^6$-Xaa$^{7a}$]-NH$_2$;
Xaa$^1$-cyclo[Xaa$^{2b}$-Xaa$^3$-Xaa$^4$-(N-Me-Xaa$^5$)-(N-Me-Xaa$^6$)-(N-Me-Xaa$^{7b}$)]—NH$_2$;
Xaa$^1$-cyclo[Xaa$^{2b}$-Xaa$^3$-Xaa$^4$-(N-Me-Xaa$^5$)-(N-Me-Xaa$^6$)-Xaa$^{7b}$]-NH$_2$;
Xaa$^1$-cyclo[Xaa$^{2b}$-Xaa$^3$-Xaa$^4$-Xaa$^5$-(N-Me-Xaa$^6$)-(N-Me-Xaa$^{7b}$)]—NH$_2$;
Xaa$^1$-cyclo[Xaa$^{2b}$-Xaa$^3$-Xaa$^4$-(N-Me-Xaa$^5$)-Xaa$^6$-(N-Me-Xaa$^{7b}$)]—NH$_2$; or
Xaa$^1$-cyclo[Xaa$^{2b}$-Xaa$^3$-Xaa$^4$-(N-Me-Xaa$^5$)-Xaa$^6$-Xaa$^{7b}$]-NH$_2$;
wherein Xaa$^1$, Xaa$^{2a}$, Xaa$^{2b}$, Xaa$^3$, Xaa$^4$, Xaa$^5$, Xaa$^6$, Xaa$^{7a}$ and Xaa$^{7b}$ may be any of the alternative definitions provided above. The MC1RTP may be cyclized by the formation of a lactam bridge, a 1,2,3-triazole, or a disulfide bridge. In some such embodiments, Xaa$^{2a}$ is Asp and Xaa$^{7a}$ is Lys, and a lactam bridge is formed between Xaa$^{2a}$ and Xaa$^{7a}$. In some such embodiments, Xaa$^{2b}$ is Lys and Xaa$^{7b}$ is Asp, and a lactam bridge is formed between Xaa$^{2b}$ and Xaa$^{7b}$. In some such embodiments, Xaa$^{2a}$ is Glu and Xaa$^{7a}$ is Orn, and a lactam bridge is formed between Xaa$^{2a}$ and Xaa$^{7a}$. In some such embodiments, Xaa$^{2b}$ is Orn and Xaa$^{7b}$ is Glu, and a lactam bridge is formed between Xaa$^{2b}$ and Xaa$^{7b}$.

In some embodiments, the MC1RTP comprises Nle-cyclo [Asp-His-(D-Phe)-Arg-Trp-Lys], wherein the MC1RTP is optionally C-terminally amidated, and wherein 1, 2, 3 or 4 of Xaa$^3$, Xaa$^5$, Xaa$^6$ and Xaa$^{7a}$ in the sequence defined by Formula I is alpha N-methylated. In some embodiments, the MC1RTP comprises, consists or consists essentially of:
Nle-cyclo[Asp-(N-Me-His)-(D-Phe)-(N-Me-Arg)-(N-Me-Trp)-(N-Me-Lys)];
Nle-cyclo[Asp-His-(D-Phe)-(N-Me-Arg)-(N-Me-Trp)-(N-Me-Lys)];
Nle-cyclo[Asp-His-(D-Phe)-(N-Me-Arg)-(N-Me-Trp)-Lys];
Nle-cyclo[Asp-His-(D-Phe)-Arg-(N-Me-Trp)-(N-Me-Lys)];
Nle-cyclo[Asp-His-(D-Phe)-(N-Me-Arg)-Trp-(N-Me-Lys)];
Nle-cyclo[Asp-His-(D-Phe)-(N-Me-Arg)-Trp-Lys];
Nle-cyclo[Asp-(N-Me-His)-(D-Phe)-(N-Me-Arg)-(N-Me-Trp)-(N-Me-Lys)]—NH$_2$;
Nle-cyclo[Asp-His-(D-Phe)-(N-Me-Arg)-(N-Me-Trp)-(N-Me-Lys)]—NH$_2$;
Nle-cyclo[Asp-His-(D-Phe)-(N-Me-Arg)-(N-Me-Trp)-Lys]-NH$_2$;
Nle-cyclo[Asp-His-(D-Phe)-Arg-(N-Me-Trp)-(N-Me-Lys)]—NH$_2$;
Nle-cyclo[Asp-His-(D-Phe)-(N-Me-Arg)-Trp-(N-Me-Lys)]—NH$_2$; or
Nle-cyclo[Asp-His-(D-Phe)-(N-Me-Arg)-Trp-Lys]-NH$_2$.
In some such embodiments, the MC1RTP is cyclized by a lactam bridge.

The linker may attach to the N-terminus of the MC1RTP. The linker may be any linker, e.g. but without limitation, ether, ester, thioether, disulfide, thioester, amide, carbamate, ureido, phosphodiester, polyethylene glycol (PEG), peptide, polypeptide, alkyl (e.g. $C_1$-$C_{10}$, $C_1$-$C_{15}$, $C_1$-$C_{20}$, $C_1$-$C_{30}$, $C_1$-$C_{50}$, $C_1$-$C_{75}$, $C_1$-$C_{100}$, $C_1$-$C_{120}$ and the like), heteroalkyl (e.g. $X_1$-$X_{10}$, $X_1$-$X_{15}$, $X_1$-$X_{20}$, $X_1$-$X_{30}$, $X_1$-$X_{50}$, $X_1$-$X_{75}$, $X_1$-$X_{100}$ and the like), aryl (e.g. $C_3$-$C_{10}$, $C_3$-$C_{15}$, $C_3$-$C_{20}$, $C_3$-$C_{30}$, $C_3$-$C_{50}$, $C_3$-$C_{75}$, $C_3$-$C_{100}$, $C_3$-$C_{120}$ and the like) or heteroaryl (e.g. $X_3$-$X_{10}$, $X_3$-$X_{15}$, $X_3$-$X_{20}$, $X_3$-$X_{30}$, $X_3$-$X_{50}$, $X_3$-$X_{75}$, $X_3$-$X_{100}$. $X_3$-$X_{120}$ and the like). The alkyl or heteroalkyl may be one or more of: branched or linear; acyclic, cyclic or multi-cyclic; saturated or unsaturated; and unsubstituted or substituted. The aryl or heteroaryl may be one or more of: cyclic or multi-cyclic; aromatic or nonaromatic; and unsubstituted or substituted. Without limitation, in substituted embodiments, the alkyl, heteroalkyl, aryl or heteroaryl may be substituted with one or more of halide, amide, oxo, hydroxyl, thiol, phosphate and sulfate. In certain embodiments, each X is independently C, N, O, P, Se or S. The halide may be —F, —Br, —I or —Cl. In certain embodiments, the halide is —Br, —I or —Cl. In some embodiments, the linker is cationic. In some embodiments, the linker has net neutral charge.

In some embodiments, the linker consists or consists essentially of a $C_1$-$C_{120}$ alkylenyl which is: linear or branched; saturated or unsaturated; and acyclic or cyclic (including multi-cyclic). In some embodiments, the linker consists or consists essentially of a $X_1$-$X_{120}$ heteroalkylenyl, which is: linear or branched; saturated or unsaturated; and acyclic or cyclic (including multi-cyclic). In some such embodiments, the linker comprises a peptide. In some such embodiments, the linker consists or consists essentially of a peptide attached to the N-terminus of the MC1RTP. For example, the peptide may be 2, 3, 4, 5, 6, 7, 8, 9, 10 or more than 10 amino acid residues long. The peptide may comprise proteinogenic and/or non-proteinogenic amino acids.

In some embodiments, the linker is a linear peptide of 3 to 6 amino acid residues, -Xaa$^8$-Xaa$^9$-(Xaa$^{10}$)$_{1-4}$-, attached to the N-terminus of the MC1RTP. In these embodiments, the radiolabeling group and the albumin-binding group are bonded to the free N-terminus of Xaa$^8$ and the side chain of Xaa$^9$, respectively, or are bonded to the side chain of Xaa$^9$ and the free N-terminus of Xaa$^8$, respectively. Xaa$^8$, Xaa$^9$ and each Xaa$^{10}$ may independently be any amino acid, including proteinogenic and/or non-proteinogenic amino acids (including D-amino acids). In some such embodiments, (Xaa$^{10}$)$_{1-4}$ is diglycine. In some embodiments, Xaa$^8$ is Gly, Glu, D-Glu, Asp, D-Asp, 2-Aad, D-2-Aad, 3-Aad, or D-3-Aad. In some embodiments, Xaa$^9$ is Lys, Orn, D-Orn, Dab, D-Dab, Dap or D-Dap, any of which can form an amide bond with a carboxylate of a radiolabeling group or an albumin binding group. In some embodiments, Xaa$^8$ is Glu or D-Glu. In some embodiments, Xaa$^9$ is Lys or D-Lys.

In some embodiments, the linker is a branched peptide of 3 to 6 amino acid residues, -Xaa$^9$(Xaa$^8$)-(Xaa$^{10}$)$_{1-4}$-, attached to the N-terminus of the MC1RTP. In these embodiments, Xaa$^9$ is Lys, D-Lys, Orn, D-Orn, Dab, D-Dab, Dap or D-Dap, the C-terminus of Xaa$^8$ forms an amide with the side chain of Xaa$^9$, and the radiolabeling group and the albumin-binding group are bonded to the free N-termini of Xaa$^8$ and Xaa$^9$, respectively, or are bonded to the free N-termini of Xaa$^9$ and Xaa$^8$, respectively. Xaa$^8$ and each Xaa$^{10}$ may independently be any amino acid, including proteinogenic and/or non-proteinogenic amino acids (including D-amino acids). In some such embodiments, (Xaa$^{10}$)$_{1-4}$ is diglycine. In some embodiments, Xaa$^8$ is Gly, Glu, D-Glu, Asp, D-Asp, 2-Aad, D-2-Aad, 3-Aad, or D-3-Aad. In some embodiments, Xaa$^8$ is Glu or D-Glu. In some embodiments, Xaa$^9$ is Lys or D-Lys.

In some embodiments, the linker comprises a linear peptide, -Xaa$^8$-Xaa$^9$-Xaa$^{10}$-, wherein the radiolabeling group and the albumin-binding group are bonded to the free N-terminus of Xaa$^8$ and the side chain of Xaa$^9$, respectively, or are bonded to the side chain of Xaa$^9$ and the free N-terminus of Xaa$^8$, respectively. In such embodiments, Xaa$^{10}$ is —N(H)R$^2$R$^3$R$^2$C(O)—, in which each R$^2$ is independently absent, methylene or ethylene, and R$^3$ is —(CH$_2$)$_n$— or

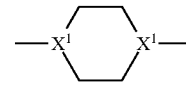

in which each X$^1$ is independently carbon or nitrogen, and n is 1, 2, 3, 4, 5, 6, 7, 8, 9, 10 or 11. In some embodiments, n is 6-8. In some embodiments, n is 7. In some embodiments, one X$^1$ is nitrogen. In other embodiments, both X$^1$ are nitrogen. In some embodiments, at least one nitrogen of X$^1$ is protonated, resulting in a cationic peptide. In some embodiments, Xaa$^{10}$ is 4-amino-1-carboxy methyl-piperidine (Pip), 4-(2-aminoethyl)-1-carboxymethyl-piperazine (Acp), or —N(H)—(CH$_2$)$_{2-15}$C(O)— (e.g. 8-aminooctanoic acid (Aoc) and the like). Xaa$^8$ and Xaa$^9$ may independently be any amino acid, including proteinogenic or non-proteinogenic amino acids (including D-amino acids). In some embodiments, Xaa$^8$ is Gly, Glu, D-Glu, Asp, D-Asp, 2-Aad, D-2-Aad, 3-Aad, or D-3-Aad. In some embodiments, Xaa$^9$ is Lys, Orn, D-Orn, Dab, D-Dab, Dap or D-Dap, any of which can form an amide bond with a carboxylate of a radiolabeling group or an albumin binding group. In some embodiments, Xaa$^8$ is Glu or D-Glu. In some embodiments, Xaa$^9$ is Lys or D-Lys.

In some embodiments, the linker comprises a branched peptide, -Xaa$^9$(Xaa$^8$)-Xaa$^{10}$-, wherein Xaa$^9$ is Lys, D-Lys, Orn, D-Orn, Dab, D-Dab, Dap or D-Dap and the C-terminus of Xaa$^8$ forms an amide with the side chain of Xaa$^9$, and wherein the radiolabeling group and the albumin-binding group are bonded to the free N-termini of Xaa$^8$ and Xaa$^9$, respectively, or are bonded to the free N-termini of Xaa$^9$ and Xaa$^8$, respectively. Xaa$^{10}$ is —N(H)R$^2$R$^3$R$^2$C(O)—, in which each R$^2$ is independently absent, methylene or ethylene, and R$^3$ is —(CH$_2$)$_n$— or

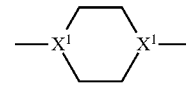

in which each X$^1$ is independently carbon or nitrogen, and n is 1, 2, 3, 4, 5, 6, 7, 8, 9, 10 or 11. In some embodiments, n is 6-8. In some embodiments, n is 7. In some embodiments, one X$^1$ is nitrogen. In other embodiments, both X$^1$ are nitrogen. In some embodiments, at least one nitrogen of X$^1$ is protonated, resulting in a cationic peptide. In some embodiments, Xaa$^{10}$ is 4-amino-1-carboxy methyl-piperidine (Pip), 4-(2-aminoethyl)-1-carboxymethyl-piperazine (Acp), or —N(H)—(CH$_2$)$_{2-15}$C(O)— (e.g. 8-aminooctanoic acid (Aoc) and the like). Xaa$^8$ may be any amino acid, including proteinogenic or non-proteinogenic amino acids (including D-amino acids). In some embodiments, Xaa$^8$ is Gly, Glu, D-Glu, Asp, D-Asp, 2-Aad, D-2-Aad, 3-Aad, or D-3-Aad. In some embodiments, Xaa$^8$ is Glu or D-Glu. In some embodiments, Xaa$^9$ is Lys or D-Lys.

The albumin-binding group may have the following structure, wherein each R$^4$ is independently H, halogen, $C_{1-5}$ alkyl, $C_{1-5}$ alkoxyl or nitro group:

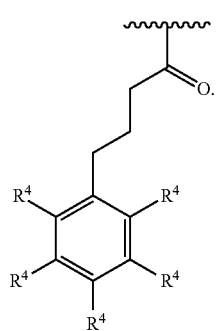

In some embodiments, three R⁴ groups are H and two R⁴ group are independently I, F, Br, Cl or methyl in meta/meta, ortho/ortho, para/meta, meta/para, para/ortho, ortho/para, meta/ortho or ortho/meta. In some embodiments, four R⁴ groups are H and one R⁴ group is I, F, Br, Cl or methyl in para, meta or ortho position. In some embodiments, the albumin-binding group is A-[4-(iodophenyl)butanoyl], A-[4-(fluorophenyl)butanoyl], A-[4-(bromophenyl)butanoyl], A-[4-(chlorophenyl) butanoyl], or A-[4-(tolyl)butanoyl], In some embodiments, the albumin-binding group is A-[4-(tolyl)butanoyl], In some embodiments, the albumin-binding group is N-[4-(p-iodophenyl)butanoyl], A-[4-(p-fluorophenyl)butanoyl], N-[4-(p-bromophenyl) butanoyl], A-[4-(p-chlorophenyl)butanoyl], or A-[4-(p-tolyl)butanoyl], In some embodiments, the albumin-binding group is A-[4-(p-tolyl)butanoyl].

In embodiments where the linker comprises the linear peptide, the albumin-binding group may be coupled to the α-amino group of Xaa⁸ and the radiolabeling group may be coupled to the side chain of Xaa⁹. In other such embodiments, the radiolabeling group may be coupled to the α-amino group of Xaa⁸ and the albumin-binding group may be coupled to the side chain of Xaa⁹.

In embodiments where the linker comprises the branched peptide, the albumin-binding group may be coupled to the α-amino group of Xaa⁸ and the radiolabeling group may be coupled to the α-amino group of Xaa⁹. In other such embodiments, the radiolabeling group may be coupled to the α-amino group of Xaa⁸ and the albumin-binding group may be coupled to the α-amino group of Xaa⁹.

The radiolabeling group may be a radioisotope chelator. Chelators may be incorporated into the compound by coupling to a peptide portion of the compound. For example, but without limitation, a bifunctional chelator, such as 1,4,7,10-tetraazacyclododecane-1,4,7,10-tetraacetic acid (DOTA) tris (tert-butyl ester) may be activated in the presence of N-hydroxysuccinimide (NHS) and N,N'-dicyclohexylcarbodiimide (DCC) for coupling to a peptide. Alternatively, a chelator may be incorporated into the compound via a copper-catalyzed click reaction under either liquid or solid phase conditions. Copper-catalyzed click reactions are well established in the art. For example, 2-azidoacetic acid is first activated by NHS and DCC and coupled to a peptide. Then, alkyne-containing DOTA (or an alternative chelator) may be clicked to the azide-containing peptide in the presence of $Cu^{2+}$ and sodium ascorbate in water and organic solvent, such as acetonitrile (ACN) and DMF and the like.

Non-limiting examples of radioisotope chelators include chelators selected from the group consisting of: DOTA; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; macropa; $H_2$dedpa, $H_4$octapa, $H_4$py4pa, $H_4$Pypa, $H_2$azapa, $H_5$decapa, and other picolinic acid derivatives; CP256; PCTA; C-NETA; C-NE3TA; HBED; SHBED; BCPA; CP256; YM103; desferrioxamine (DFO) and DFO derivatives; and $H_6$phospa. Exemplary non-limiting examples of radioisotope chelators and radioisotopes chelated by the chelators are shown in Table 1. In alternative embodiments, the radioisotope chelator in the compound is one of those listed above or in Table 1, or is any other radioisotope chelator. One skilled in the art could replace any of the chelators listed herein with another chelator.

TABLE 1

Exemplary chelators and exemplary isotopes which bind said chelators

| Chelator | Isotopes |
|---|---|
| DOTA, 1,4,7,10-tetraazacyclododecane-1,4,7,10-tetraacetic acid | Cu-64/67<br>Ga-68<br>In-111<br>Lu-177<br>Y-86/90<br>Bi-213<br>Pb-212<br>Ac-225<br>Gd-159<br>Yb-175<br>Ho-166<br>As-211<br>Sc-44/47<br>Pm-149<br>Pr-142 |

TABLE 1-continued

Exemplary chelators and exemplary isotopes which bind said chelators

| Chelator | Isotopes |
|---|---|
| 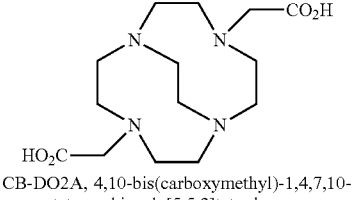<br>CB-DO2A, 4,10-bis(carboxymethyl)-1,4,7,10-tetraazabicyclo[5.5.2]tetradecane | Cu-64/67 |
| 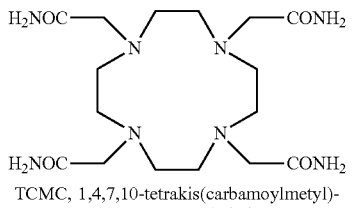<br>TCMC, 1,4,7,10-tetrakis(carbamoylmetyl)-1,4,7,10-tetraazacyclododecane | Pb-212 |
| 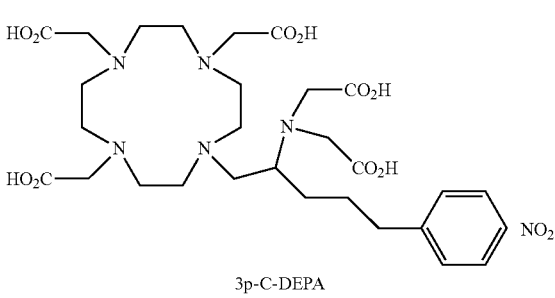<br>3p-C-DEPA | Bi-212/213 |
| 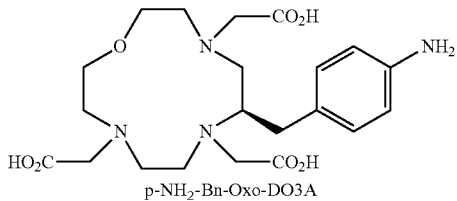<br>p-NH$_2$-Bn-Oxo-DO3A | Cu-64/67 |
| 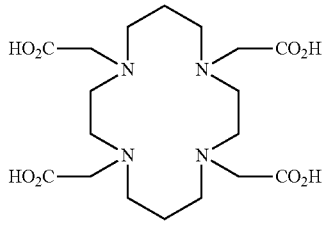 [SMILES: O=C(O)CN1CCCN(CC(=O)O)CCN(CC(=O)O)CCCN(CC(=O)O)CC1]<br>TETA, 1,4,8,11-tetraazacyclotetradecane-1,4,8,11-tetraacetic acid | Cu-64/67 |
| 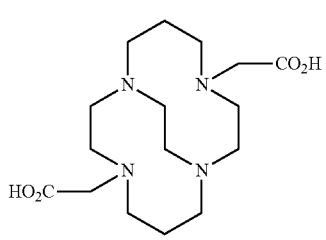 [SMILES: O=C(O)CN1CCCN2CCN(CCCN(CC(=O)O)CC2)CC1]<br>CB-TE2A, 4,11-bis-(carboxymethyl)-1,4,8,11-tetraazabicyclo[6.6.2]-hexadecane | Cu-64/67 |

TABLE 1-continued

Exemplary chelators and exemplary isotopes which bind said chelators

| Chelator | Isotopes |
|---|---|
| 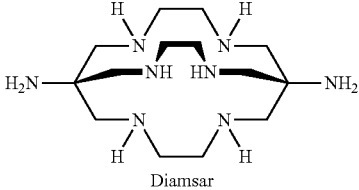<br>Diamsar | Cu-64/67 |
| 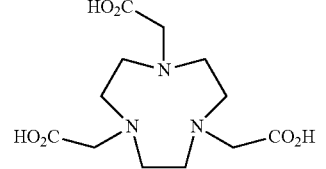 [SMILES: O=C(O)CN1CCN(CC(=O)O)CCN(CC(=O)O)CC1]<br>NOTA, 1,4,7-triazacyclononane-1,4,7-triacetic acid | Cu-64/67<br>Ga-68<br>In-111<br>Sc-44/47 |
| 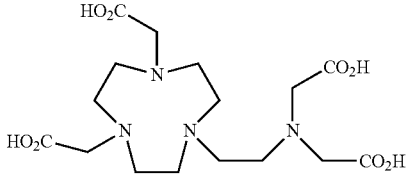 [SMILES: O=C(O)CN1CCN(CCN(CC(=O)O)CC(=O)O)CCN(CC(=O)O)CC1]<br>NETA, {4[2-(bis-carboxymethylamino)-ethyl]-<br>7-carboxymethyl-[1,4,7]triazonan-1-yl}-acetic acid | Cu-64/67<br>Ga-68<br>Lu-177<br>Y-86/90<br>Bi-213<br>Pb-212 |
| 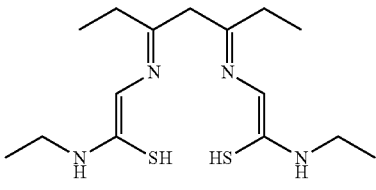 [SMILES: CCN/C(S)=C/N=C(\CC)C/C(CC)=N/C=C(\S)NCC]<br>HxTSE | Au-198/199 |
| 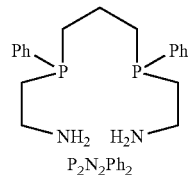<br>P$_2$N$_2$Ph$_2$ | Rh-105 |
| 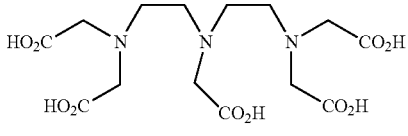 [SMILES: O=C(O)CN(CCN(CC(=O)O)CC(=O)O)CCN(CC(=O)O)CC(=O)O]<br>DTPA, diethylenetriaminepentaacetic acid | In-111<br>Sc-44/47<br>Lu-177<br>Y-86/90<br>Sn-117m<br>Pd-109 |
| 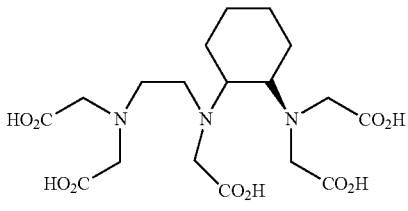<br>CHX-A00-DTPA, 2-(p-isothiocyanatobenzyl)-<br>cyclohexyldiethylenetriaminepentaacetic<br>acid | In-111<br>Lu-177<br>Y-86/90<br>Bi-212/213 |

TABLE 1-continued
Exemplary chelators and exemplary isotopes which bind said chelators
| Chelator | Isotopes |
|---|---|
| 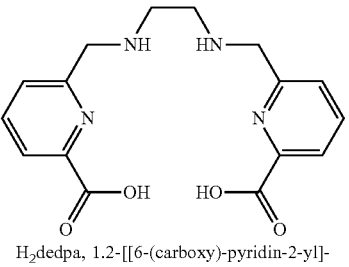 H₂dedpa, 1.2-[[6-(carboxy)-pyridin-2-yl]-methylamino]ethane | Cu-64/67 |
| 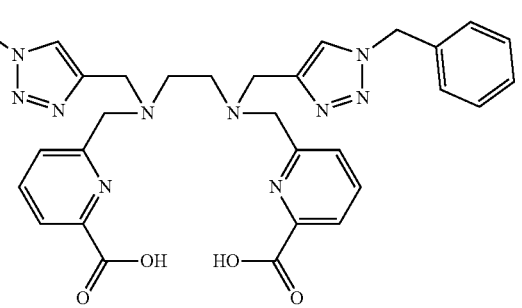 H₂azapa, N,N0-[1-benzyl-1,2,3-triazole-4-yl]methyl-N,N0-[6-(carboxy)pyridin-2-yl]-1,2-diaminoethane | Cu-64/67 |
| 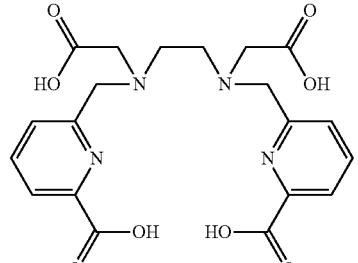 H₄cclapa | In-111<br>Lu-177<br>Y-86/90<br>Ac-225 |
| 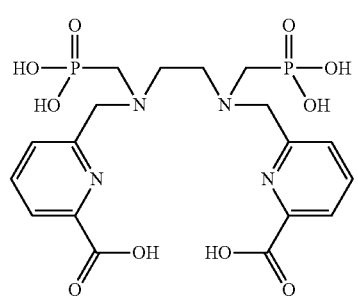 [SMILES: O=C(O)c1cccc(CN(CCN(Cc2cccc(C(=O)O)n2)CP(=O)(O)O)CP(=O)(O)O)n1] H₅phospa | Ac-225 |

TABLE 1-continued
Exemplary chelators and exemplary isotopes which bind said chelators
| Chelator | Isotopes |
|---|---|
| 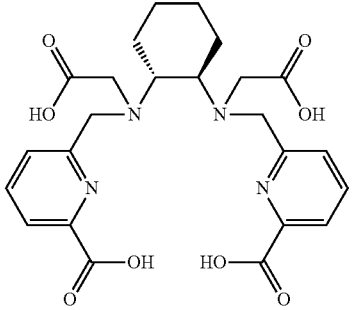 [SMILES: O=C(O)CN(Cc1cccc(C(=O)O)n1)[C@@H]1CCCC[C@H]1N(CC(=O)O)Cc1cccc(C(=O)O)n1]<br>H₄CHXoctapa | In-111<br>Ac-225 |
| 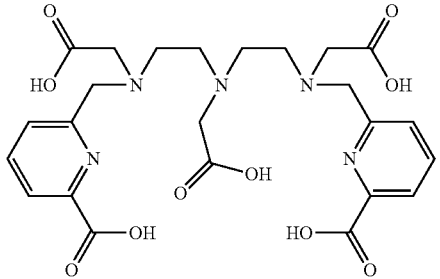 [SMILES: O=C(O)CN(CCN(CC(=O)O)Cc1cccc(C(=O)O)n1)CCN(CC(=O)O)Cc1cccc(C(=O)O)n1]<br>H₅decapa | In-111<br>Lu-177<br>Ac-225 |
| 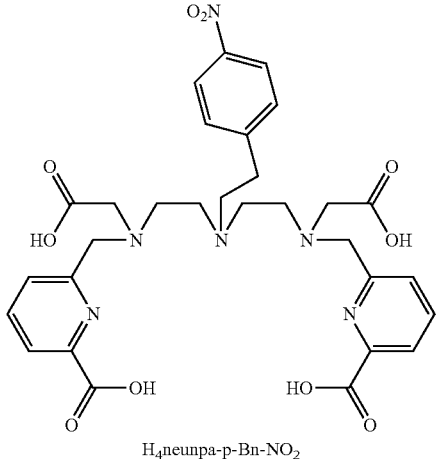<br>H₄neunpa-p-Bn-NO₂ | In-111<br>Lu-177<br>Ac-225 |
| 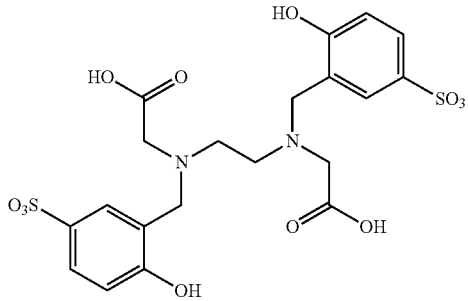<br>SHBED, N,N0-bis(2-hydroxy-5-sulfobenzyl)-<br>ethylenediamine-N,N0-deacetic acid | In-111<br>Ga-68 |

TABLE 1-continued

Exemplary chelators and exemplary isotopes which bind said chelators

| Chelator | Isotopes |
|---|---|
| 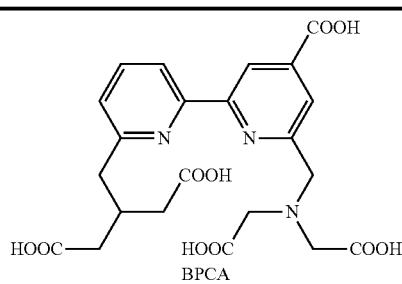 BPCA | In-111 |
| 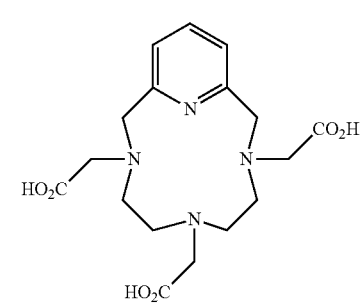 PCTA, 3,6,9,15-tetraazabycyclo[9.3.1]-pentadeca-1(15),11,13-triene-3,6,9-triacetic acid | Cu-64/67 |

In some embodiments, the radioisotope chelator is conjugated with a radioisotope. The conjugated radioisotope may be, without limitation, $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{203}$Pb, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr, $^{114m}$In, $^{111}$In, $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{203}$Pb, $^{188}$Re, $^{186}$Re, $^{149}$Pm, $^{105}$Rh, $^{198}$Au, $^{199}$Au, and the like. In some embodiments, the chelator is a chelator from Table 1 and the conjugated radioisotope is a radioisotope indicated in Table 1 as a binder of the chelator. In some embodiments, the conjugated radioisotope is a therapeutic radioisotope (e.g. a beta emitter or an alpha emitter). Non-limiting examples of therapeutic radioisotopes include. $^{64}$Cu, $^{67}$Ga, $^{111}$In, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr or $^{114m}$In. In some embodiments, the conjugated radioisotope is suitable for PET or SPECT imaging (e.g. a positron emitter or a gamma emitter). Non-limiting examples of positron or gamma emitting radioisotopes include $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{203}$Pb, $^{188}$Re, $^{186}$Re, $^{149}$Pm, $^{105}$Rh, $^{198}$Au or $^{199}$Au.

There is also provided a compound having the following structure or a salt thereof,

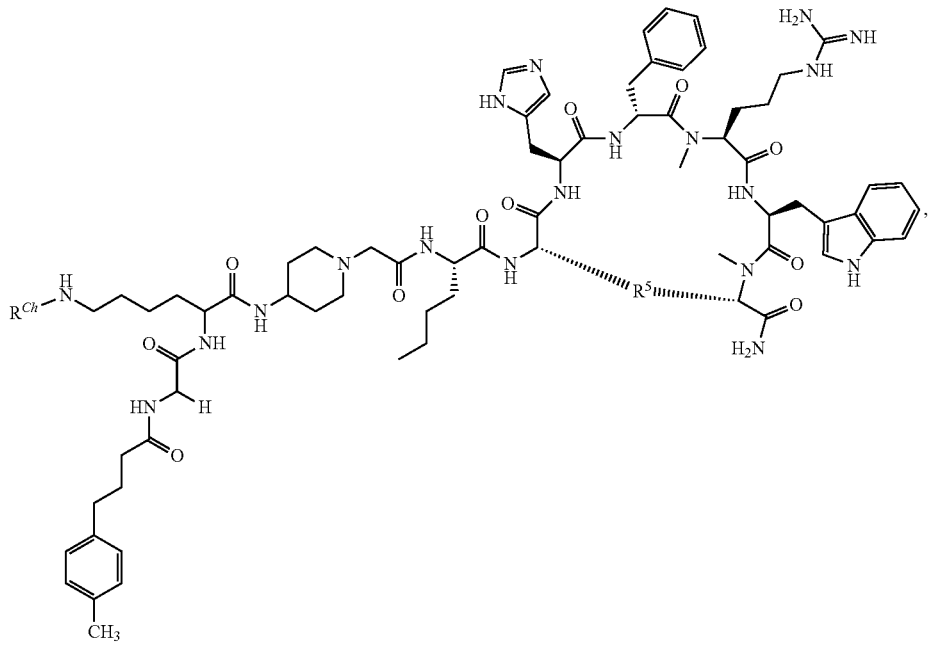

wherein $R^5$ is —(CH$_2$)$_{1-2}$C(O)N(H)(CH$_2$)$_{1-4}$— or —(CH$_2$)$_{1-4}$N(H)C(O)(CH$_2$)$_{1-2}$—; and wherein $R^{Ch}$ is a radioisotope chelator, optionally conjugated with a radioisotope. In some embodiments, the radioisotope chelator is DOTA conjugated with $^{177}$Lu, $^{111}$In, $^{213}$Bi, $^{68}$Ga, $^{67}$Ga, $^{203}$Pb, $^{212}$Pb, $^{44}$Sc, $^{90}$Y, $^{86}$Y, $^{225}$Ac, $^{64}$Cu or $^{67}$Cu. In some embodiments, the radioisotope chelator is Macropa conjugated with $^{225}$Ac. In some embodiments, the radioisotope chelator is Me-3,2-HOPO conjugated with $^{227}$Th. In some embodiments, the radioisotope chelator is H$_4$py4pa conjugated with $^{225}$Ac or $^{177}$Lu. In some embodiments, the radioisotope chelator is H$_4$pypa conjugated with $^{177}$Lu. In some embodiments, the radioisotope chelator is NODAGA conjugated with $^{68}$Ga. In some embodiments, the radioisotope chelator is DTPA conjugated with $^{111}$In. In some embodiments, the radioisotope chelator is DFO conjugated with $^{89}$Zr.

There is also provided a compound having the following structure, or a salt thereof

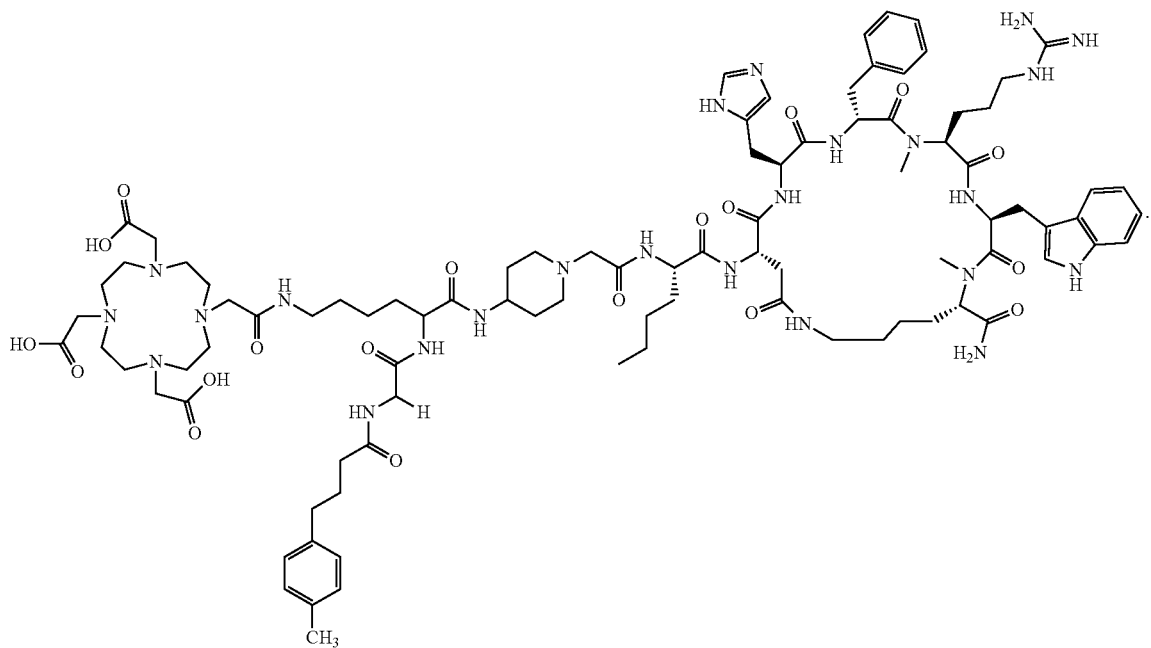 [SMILES: CCCC[C@H](NC(=O)CN1CCC(NC(=O)C(CCCCNC(=O)CN2CCN(CC(=O)O)CCN(CC(=O)O)CCN(CC(=O)O)CC2)NC(=O)CNC(=O)CCCc2ccc(C)cc2)CC1)C(=O)N[C@H]1CC(=O)NCCCC[C@@H](C(N)=O)N(C)C(=O)[C@H](Cc2c[nH]c3ccccc23)NC(=O)[C@H](CCCNC(=N)N)N(C)C(=O)[C@@H](Cc2ccccc2)NC(=O)[C@H](Cc2cnc[nH]2)NC1=O]

In some embodiments, the compound is conjugated with $^{177}$Lu, $^{in}$In, $^{213}$Bi, $^{68}$Ga, $^{67}$Ga, $^{203}$Pb, $^{212}$Pb, $^{44}$Sc, $^{90}$Y, $^{86}$Y, $^{64}$Cu, $^{67}$Cu or $^{225}$Ac. In some embodiments, the compound is conjugated with $^{225}$Ac.

There is also provided a compound having the following structure or a salt thereof, optionally conjugated with $^{225}$Ac:

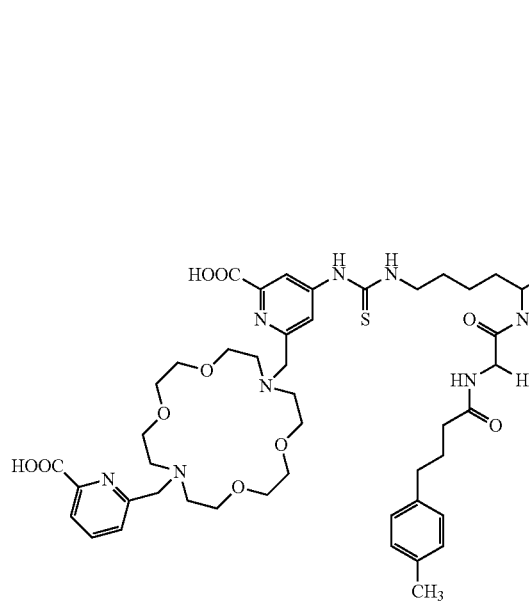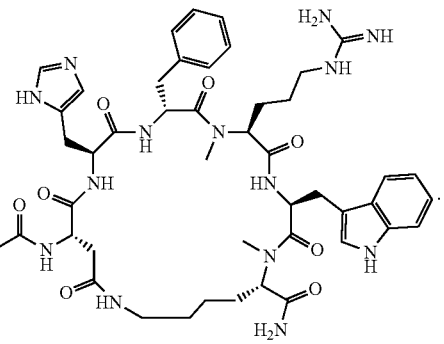

III. Uses/Methods

This section incorporates all embodiments and combinations of features of the compounds described in Section II.

There is also disclosed a pharmaceutical composition comprising a compound as defined in Section II and a pharmaceutically acceptable excipient, carrier or diluent. The compound may be any of the embodiments (or combination of features thereof) defined in Section II. The compound may be conjugated with a therapeutic radioisotope (as defined in Section II) or may be conjugated with a radioisotope that is suitable for PET or SPECT imaging (as defined in Section II).

The compounds may be useful in preparing a radioisotope-conjugated compound. There is therefore provided a method of preparing a radioisotope-conjugated compound comprising conjugating a radioisotope as defined in Section II to the radioisotope chelator of a compound as defined in Section II. The compound may be any of the embodiments (or combination of features thereof) defined in Section II. The radioisotope may be a therapeutic radioisotope (as defined in Section II) or may be a radioisotope that is suitable for PET or SPECT imaging (as defined in Section II).

When the compound comprises a radioisotope conjugated to the radioisotope chelator, the compound may be useful for treating an MC1R-related disease or condition (e.g. melanoma and the like) or for positron emission tomography (PET) or single photon emission computed tomography (SPECT) imaging of an MC1R-related disease or condition (e.g. melanoma and other diseases/conditions involving MC1R-expressing tissues. As the Examples in Section IV demonstrate, alpha N-methylation of Xaa$^3$, Xaa$^5$, Xaa$^6$ and Xaa$^{7a}$ resulted in exceptional selectivity for MC1R over other melanocortin receptors compared to a peptide lacking N-methylations (see Example 1). The N-methylations also improved peptide stability (see Example 1), but decreased MC1R binding affinity (see Example 2). Surprisingly, the combined effect of N-methylations (important for MC1R selectivity) plus an albumin-binding group was a novel and useful balance between peptide stability and MC1R binding affinity (see Example 3). This cooperative effect provides improved tumour uptake and biodistribution, resulting in improved utility for PET/SPECT imaging and therapy (see Examples 3 and 4). In other words, when the radiolabeled compounds have N-methylated peptides but no albumin-binding group, they are cleared quickly from the blood pool without a sufficient chance to bind to cancer cells even though they are stable in vivo. On the other hand, when the radiolabeled compounds have the albumin-binding group but no N-methylation, they are too rapidly degraded to metabolites to usefully bind cancer cells for imaging or therapy. By incorporating both alpha N-methylation and albumin-binding, compounds herein disclosed may achieve both target selectivity and improved metabolic stability to deliver a radioactive payload to MC1R-expressing tissues.

There is therefore provided a method of treating an MC1R-related disease, comprising administering a compound as defined in Section II to a subject, wherein a radioisotope defined in Section II is conjugated to the radioisotope chelator of the compound, and wherein the radioisotope is a therapeutic radioisotope. There is therefore also provided the use of the compound or the radioisotope-conjugated to compound in manufacture of a medicament for treatment of an MC1R-related disease or condition, wherein the radioisotope is a therapeutic radioisotope. The radioisotope-conjugated compound may be comprised in a pharmaceutical composition. The compound may be any of the embodiments (or any combination of features thereof) defined in Section II. For example, but without limitation, the compound may comprise a melanocortin 1 receptor (MC1R) targeting peptide (MC1RTP), a radiolabeling group, and a linker joining the MC1RTP to the radiolabeling group, wherein: the MC1RTP is linear or cyclized, and comprises a sequence of Formula I or Formula II; $Xaa^1$ is norleucine (Nle), D-Nle, Ala, D-Ala, Leu, D-Leu, Ile, D-Ile, Cys, D-Cys, Met, D-Met, Phe, D-Phe, Trp, D-Trp, Val, D-Val, 3-(1-naphtyl)alanine (Nal), D-Nal, 3-(2-naphtyl)alanine (2-Nal), D-2-Nal, Gly, α-aminobutryic acid, D-α-aminobutryic acid, norvaline, D-norvaline, homonorleucine, or D-homonorleucine; $Xaa^{2a}$ is Cys, D-Cys, Asp, D-Asp, Glu, D-Glu, 2-aminoadipic acid (2-Aad), D-2-Aad, 3-aminoadipic acid (3-Aad), D-3-Aad, propargylglycine (Pra), D-Pra, homopropargylglycine (Hpg), D-Hpg, beta-homopropargylglycine (Bpg) or D-Bpg; $Xaa^{2b}$ is Cys, D-Cys, Lys, D-Lys, Ornithine (Orn), D-Orn, 2,4-diaminobutyric acid (Dab), D-Dab, 2,3-diaminopropionic acid (Dap), D-Dap, Lys($N_3$), D-Lys($N_3$), Orn($N_3$), D-Orn($N_3$), Dab($N_3$), D-Dab($N_3$), Dap($N_3$), D-Dap($N_3$), 2-(5'-azidopentyl)alanine, D-2-(5'-azidopentyl)alanine, 2-(6'-azidohexyl)alanine or D-2-(6'-azidohexyl)alanine; $Xaa^3$ is His, D-His, Pro, beta-(1,2,3-triazol-4-yl)-L-alanine, beta-(1,2,3-triazol-4-yl)-D-alanine, 1,2,4-triazole-3-alanine, or 1,2,4-triazole-3-D-alanine; $Xaa^4$ is Phe, D-Phe, 2-Nal, D-2-Nal, Phe(4-F), D-Phe(4-F), Phe(4-Cl), D-Phe(4-Cl), Phe(4-Br), D-Phe(4-Br), Phe(4-I), D-Phe(4-I), Phe(4-$NH_2$), D-Phe(4-$NH_2$), Phe(4-$NO_2$), or D-Phe(4-$NO_2$); $Xaa^5$ is Arg, D-Arg, homoarginine (hArg), D-hArg, Leu, D-Leu, 2-amino-4-guanidinobutyric acid (Agb), D-Agb, 2-amino-3-guanidinopropionic acid (Agp) or D-Agp; $Xaa^6$ is Phe, D-Phe, Trp, D-Trp, Trp(5-Br), D-Trp(5-Br), Trp(5-$OCH_3$), D-Trp(5-$OCH_3$), Trp(6-F), D-Trp(6-F), Trp(5-OH), D-Trp(5-OH), Trp(CHO), or D-Trp(CHO); $Xaa^{7a}$ is Cys, D-Cys, Lys, D-Lys, Orn, D-Orn, Dab, D-Dab, Dap, D-Dap, Lys($N_3$), D-Lys($N_3$), Orn($N_3$), D-Orn($N_3$), Dab($N_3$), D-Dab($N_3$), Dap($N_3$), D-Dap($N_3$), 2-(5'-azidopentyl)alanine, D-2-(5'-azidopentyl)alanine, 2-(6'-azidohexyl)alanine or D-2-(6'-azidohexyl)alanine; $Xaa^{7b}$ is Cys, D-Cys, Asp, D-Asp, Glu, D-Glu, 2-Aad, D-2-Aad, 3-Aad, D-3-Aad, Pra, D-Pra, Hpg, D-Hpg, Bpg or D-Bpg; the MC1RTP is optionally C-terminally amidated; one or more amino acid residues of the MC1RTP is alpha N-methylated, wherein 1, 2, 3 or 4 of $Xaa^3$, $Xaa^5$, $Xaa^6$ and $Xaa^{7a}$ is alpha N-methylated and wherein 1, 2, 3 or 4 of $Xaa^3$, $Xaa^5$, $Xaa^6$ and $Xaa^{7b}$ is alpha N-methylated; the linker comprises an albumin-binding group, and the radiolabeling group is a radioisotope chelator. The MC1R-related disease or condition may be an MC1R-expressing cancer. Increased MC1R expression has been detected in various cancers, including without limitation melanoma as well as non-melanoma skin cancer. For example, but without limitation, MC1R is specifically expressed in cutaneous, amelanotic and uveal melanomas. Accordingly, without limitation, the MC1R-expressing cancer may be melanoma or non-melanoma skin cancer. The MC1R-expressing cancer may be primary and/or metastatic melanoma. The MC1R-expressing cancer may be uveal melanoma. The MC1R-expressing cancer may be melanoma. The therapeutic radioisotope may be a therapeutic alpha emitter, a therapeutic beta emitter or a therapeutic auger emitter. In some embodiments, the therapeutic radioisotope is $^{64}$Cu, $^{67}$Ga, $^{111}$In, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr or $^{114m}$In.

There is also provided a method of imaging MC1R-expressing tissues in a subject, in which the method comprises: administering to the subject a compound as defined in Section II; and imaging tissue of the subject using PET or SPECT. When the tissue is a diseased tissue (e.g. an MC1R-expressing cancer), MC1R-targeted treatment may then be selected for treating the subject. The radioisotope-conjugated compound may be comprised in a pharmaceutical composition. The compound may be any of the embodiments (or any combination of features thereof) defined in Section II. For example, but without limitation, the compound may comprise a melanocortin 1 receptor (MC1R) targeting peptide (MC1RTP), a radiolabeling group, and a linker joining the MC1RTP to the radiolabeling group, wherein: the MC1RTP is linear or cyclized, and comprises a sequence of Formula I or Formula II; $Xaa^1$ is norleucine (Nle), D-Nle, Ala, D-Ala, Leu, D-Leu, Ile, D-Ile, Cys, D-Cys, Met, D-Met, Phe, D-Phe, Trp, D-Trp, Val, D-Val, 3-(1-naphtyl)alanine (Nal), D-Nal, 3-(2-naphtyl)alanine (2-Nal), D-2-Nal, Gly, α-aminobutryic acid, D-α-aminobutryic acid, norvaline, D-norvaline, homonorleucine, or D-homonorleucine; $Xaa^{2a}$ is Cys, D-Cys, Asp, D-Asp, Glu, D-Glu, 2-aminoadipic acid (2-Aad), D-2-Aad, 3-aminoadipic acid (3-Aad), D-3-Aad, propargylglycine (Pra), D-Pra, homopropargylglycine (Hpg), D-Hpg, beta-homopropargylglycine (Bpg) or D-Bpg; $Xaa^{2b}$ is Cys, D-Cys, Lys, D-Lys, Ornithine (Orn), D-Orn, 2,4-diaminobutyric acid (Dab), D-Dab, 2,3-diaminopropionic acid (Dap), D-Dap, Lys(Ns), D-Lys(Ns), Orn(Ns), D-Orn(Ns), Dab(Ns), D-Dab(Ns), Dap($N_3$), D-Dap($N_3$), 2-(5'-azidopentyl)alanine, D-2-(5'-azidopentyl)alanine, 2-(6'-azidohexyl)alanine or D-2-(6'-azidohexyl)alanine; $Xaa^3$ is His, D-His, Pro, beta-(1,2,3-triazol-4-yl)-L-alanine, beta-(1,2,3-triazol-4-yl)-D-alanine, 1,2,4-triazole-3-alanine, or 1,2,4-triazole-3-D-alanine; $Xaa^4$ is Phe, D-Phe, 2-Nal, D-2-Nal, Phe(4-F), D-Phe(4-F), Phe(4-Cl), D-Phe(4-Cl), Phe(4-Br), D-Phe(4-Br), Phe(4-I), D-Phe(4-I), Phe(4-$NH_2$), D-Phe(4-$NH_2$), Phe(4-$NO_2$), or D-Phe(4-$NO_2$); $Xaa^5$ is Arg, D-Arg, homoarginine (hArg), D-hArg, Leu, D-Leu, 2-amino-4-guanidinobutyric acid (Agb), D-Agb, 2-amino-3-guanidinopropionic acid (Agp) or D-Agp; $Xaa^6$ is Phe, D-Phe, Trp, D-Trp, Trp(5-Br), D-Trp(5-Br), Trp(5-$OCH_3$), D-Trp(5-$OCH_3$), Trp(6-F), D-Trp(6-F), Trp(5-OH), D-Trp(5-OH), Trp(CHO), or D-Trp(CHO); $Xaa^{7a}$ is Cys, D-Cys, Lys, D-Lys, Orn, D-Orn, Dab, D-Dab, Dap, D-Dap, Lys($N_3$), D-Lys($N_3$), Orn($N_3$), D-Orn($N_3$), Dab($N_3$), D-Dab($N_3$), Dap($N_3$), D-Dap($N_3$), 2-(5'-azidopentyl)alanine, D-2-(5'-azidopentyl)alanine, 2-(6'-azidohexyl)alanine or D-2-(6'-azidohexyl)alanine; $Xaa^{7b}$ is Cys, D-Cys, Asp, D-Asp, Glu, D-Glu, 2-Aad, D-2-Aad, 3-Aad, D-3-Aad, Pra, D-Pra, Hpg, D-Hpg, Bpg or D-Bpg; the MC1RTP is optionally C-terminally amidated; one or more amino acid residues of the MC1RTP is alpha N-methylated, wherein 1, 2, 3 or 4 of $Xaa^3$, $Xaa^5$, $Xaa^6$ and $Xaa^{7a}$ is alpha N-methylated and wherein 1, 2, 3 or 4 of $Xaa^3$, $Xaa^5$, $Xaa^6$ and $Xaa^{7b}$ is alpha N-methylated; the linker comprises an albumin-binding group, and the radiolabeling group is a radioisotope chelator. In certain embodiments, the radioisotope-conjugated compound is useful for melanoma detection and staging. The radioisotope may be a positron emitter or a gamma emitter. In some embodiments, the radioisotope is $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{203}$Pb, $^{188}$Re, $^{186}$Re, $^{149}$Pm, $^{105}$Rh, $^{198}$Au or $^{199}$Au. Without limitation, the MC1R-expressing cancer may be melanoma or non-melanoma skin cancer. The MC1R-expressing cancer may be primary and/or metastatic melanoma. The MC1R-expressing cancer may be uveal melanoma. The MC1R-expressing cancer may be melanoma.

Without limitation, the compound or pharmaceutical composition may be administered to the subject intravenously, or as a subcutaneous or intradermal injection surrounding the site of the initial tumour (e.g. to detect lymphatic spread).

IV. Examples

The present invention is further illustrated in the following examples.

Example 1: CCZ01099

The structure of CCZ01099 (DOTA-Pip-Nle-cyclo[Asp-(N-Me-His)-D-Phe-(N-Me)-Arg-(N-Me-Trp)-(N-Me-Lys)]—$NH_2$ is shown below:

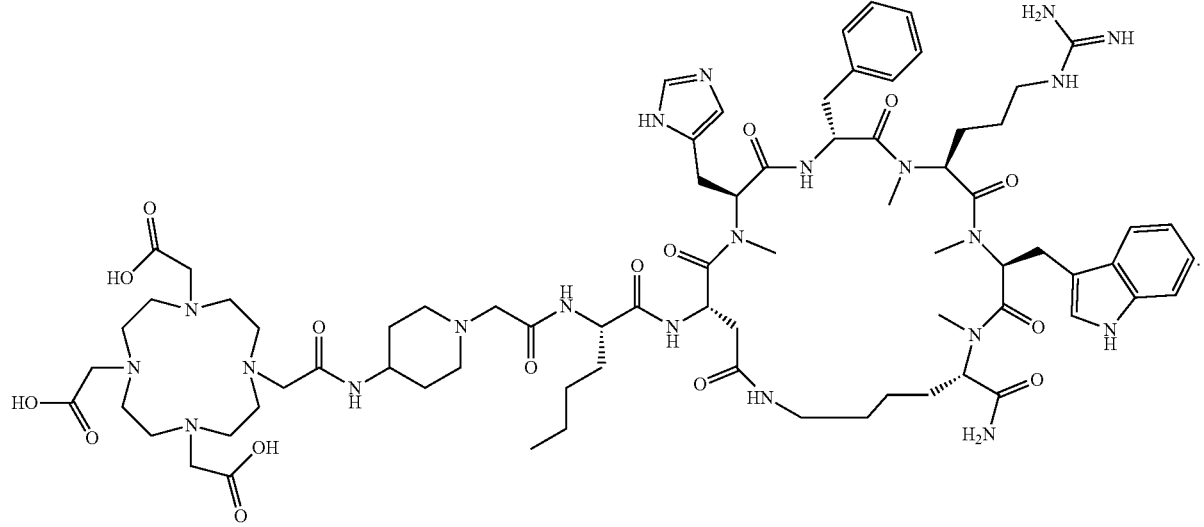 [SMILES: CCCC[C@H](NC(=O)CN1CCC(NC(=O)CN2CCN(CC(=O)O)CCN(CC(=O)O)CCN(CC(=O)O)CC2)CC1)C(=O)N[C@H]1CC(=O)NCCCC[C@@H](C(N)=O)N(C)C(=O)[C@H](Cc2c[nH]c3ccccc23)N(C)C(=O)[C@H](CCCNC(=N)N)N(C)C(=O)[C@@H](Cc2ccccc2)NC(=O)[C@H](Cc2cnc[nH]2)N(C)C1=O]

Synthesis of CCZ01099

CCZ01099 was synthesized via Fmoc chemistry. Fmoc-Rink-Amide-MBHA resin was swelled in dichloromethane (DCM), and the Fmoc protecting group was removed by treating the resin with 20% piperidine in dimethylformamide (DMF). Fmoc-protected amino acid Fmoc-Lys(Mtt)-OH (3 equivalents) was coupled to the resin in presence of HATU (3 equivalents), HOAt (3 equivalents) and DIEA (6 equivalents) followed by Fmoc removal. V-methylation was performed under Mitsunobu conditions, the free primary amine group is first protected using a solution of 4-nitrobenzene-sulfonyl chloride (Ns-Cl) and 2,4,6-trimethylpyridine (collidine) in 1-methyl-2-pyrrolidone (NMP). V-methylation was achieved in presence of triphenylphosphine, diisopropyl azodicarboxylate (DIAD) and methanol. Subsequently, N-deprotection was performed using mercaptoethanol and 1,8-diazabicyclo[5.4.0]undec-7-ene (DBU) in NMP. Subsequently, Fmoc-protected amino acids, Fmoc-N-Me-Trp(Boc)-OH, Fmoc-N-Me-Arg(Pbf)-OH, Fmoc-D-Phe-OH, Fmoc-N-Me-His(Trt)-OH, Fmoc-Asp(O-2-PhiPr)-OH, and Fmoc-Nle-OH were coupled to the resin sequentially as described above. Before deprotection of the Fmoc group on the Fmoc-Nle-OH, the Mtt group on the Lys and the O-2-PhiPr group on the Asp were selectively removed by 2.5% trifluoroacetic acid (TFA). The Lys and the Asp were then cyclized in presence of HATU (1 equivalent), HOAt (1 equivalent) and DIEA (2 equivalents). The Fmoc protecting group was removed, Fmoc-Pip-OH and the DOTA chelator was coupled as described above.

The peptide was simultaneously deprotected and cleaved from the resin by incubating with 90/5/2.5/2.5 TFA/Phenol/H2O/triisopropylsilane for 3 h at room temperature. The solution containing the peptide was filtered and precipitated in diethyl ether, and purified on a semi-preparative column using 21% acetonitrile containing 0.1% TFA at a flow rate of 4.5 mL/min using high-performance liquid chromatography (HPLC, Agilent). The HPLC eluate was collected and lyophilized, and the purity of the peptide was >99%. Mass analysis for CCZ01099 was performed on a 4000 QTRAP mass spectrometer (AB/Sciex), mass calculated 1563.87, found 1564.89 (M+1H). For gallium complexation, CCZ01099 and $GaCl_3$ (5 equivalents) in sodium acetate buffer (0.1 M, pH 4.2) was incubated at 80° C. for 15 min. The mixture was purified by HPLC using the same condition as described above.

In Vitro Selectivity

Figure 1B:
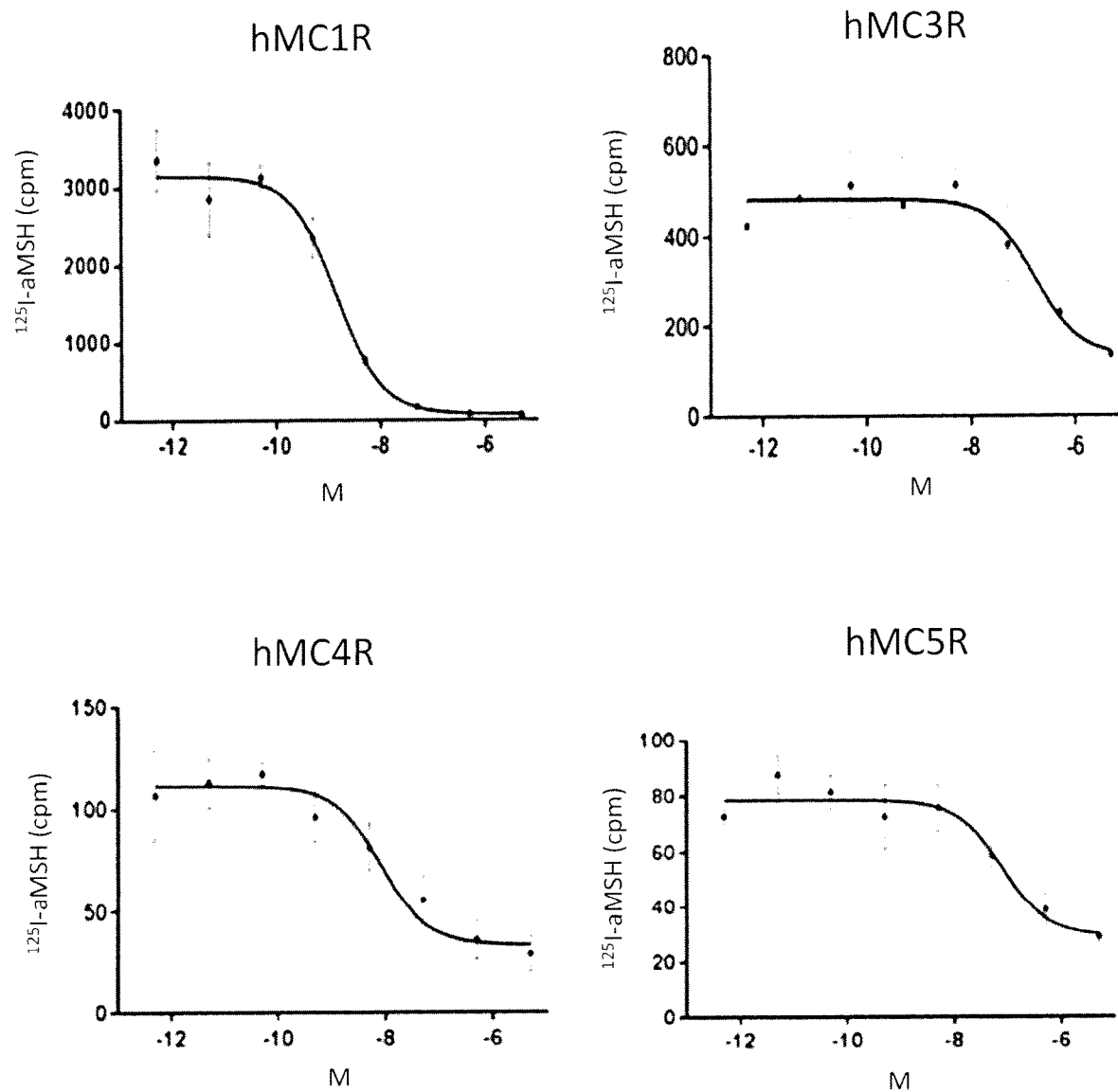
FIG. 1B shows representative competitive binding curves for compound $^{nat}$Ga-CCZ01048 in binding to hMC1R, hMC3R, hMC4R and hMC5R.

In vitro competitive binding assays were performed using human MC1R, MC3R, MC4R and MC5R membranes (Perkin Elmer) according to manufacturer's recommended procedures. The membranes were diluted with assay buffer (1:150 dilution, 25 mM HEPES pH 7.0, 1.5 mM $CaCl_2$, 1 mM $MgSO_4$, 100 mM NaCl, 0.2% BSA, 1 mM 1,10-phenanthroline, 1 complete protease inhibitor tablet (EDTA free)/100 mL), incubated with $^{nat}$Ga-CCZ01099 and $^{125}$I-[Nle$^4$, D-Phe$^7$]-αMSH ($^{125}$I-NDP-αMSH, Perkin Elmer) at 37° C. with moderate agitation for 1 h. The binding of $^{125}$I-NDP-αMSH was competed by the $^{nat}$Ga-CCZ01099 at increasing concentrations from 0.5 pM to 50 µM. After the incubation, the reaction mixture was aspirated, and membranes were washed with ice-cold wash buffer (25 mM HEPES pH 7.0, 1.5 mM $CaCl_2$, 1 mM $MgSO_4$, 100 mM NaCl) via GC/F filter (pre-soaked in 0.5% PEI). The radioactivity was measured using a Wallac WIZARD2 gamma counter (Perkin Elmer). As a control, the same experiment was repeated with $^{nat}$Ga-CCZ01048, a previously developed αMSH analogue having the sequence DOTA-Pip-Nle-cyclo[Asp-His-D-Phe-Arg-Trp-Lys]-$NH_2$ and lacking both N-methylation and an albumin-binding group (see Zhang et al., 2017 Theranostics 7(4):805-813). The inhibition constants (Ki) of $^{nat}$Ga-CCZ01099 and $^{nat}$Ga-CCZ01048 to hMC1R, hMC3R, hMC4R and hMC5R are summarized in Table 2. Representative competitive binding curves are shown in FIG. 1. With A-methylation, $^{nat}$Ga-CCZ01099 is highly selective to MC1R in comparison to the relatively low selectivity of $^{nat}$Ga-CCZ01048 to melanocortin family of receptors.

TABLE 2

Inhibition constants ($K_i$) of $^{nat}$Ga-CCZ01099 and $^{nat}$Ga-CCZ01048 to hMC1R, hMC3R, hMC4R and hMC5R (n ≥ 3).

|  | hMC1R (nM) | hMC3R (nM) | hMC4R (nM) | hMC5R (nM) |
| --- | --- | --- | --- | --- |
| $^{nat}$Ga-CCZ01099 | 6.62 ± 6.31 | NB | NB | NB |
| $^{nat}$Ga-CCZ01048 | 0.69 ± 0.62 | 83.9 ± 24.8 | 6.05 ± 2.23 | 45.5 ± 38.9 |

NB, no specific binding observed.

Radiolabeling $^{68}$Ga was obtained from a 15/12/A $^{68}$Ga generator (iThemba Labs), by eluting with 2.5 mL of 0.6 M HCl and mixed with 2 mL 12 M HCl. The mixture was passed through a DGA resin column, which was subsequently washed by 3 mL 5 M HCl. After the column was air-dried, $^{68}$Ga was eluted off with 0.5 mL deionized water. The purified $^{68}$Ga solution was mixed with 0.7 mL of HEPES buffer (2 M, pH 5.4) and the DOTA conjugated CCZ01099 or CCZ01048. Radiolabeling reaction was carried out under microwave heating for 1 min. The reaction mixture was purified by HPLC using a semi-preparative C18 column eluted with 21% acetonitrile containing 0.1% TFA at a flow rate of 4.5 mL/min. Radiochemical purity of >95% was achieved for the labeled peptides as determined by radio HPLC using an analytical C18 column.

In Vivo Stability

Figure 2:
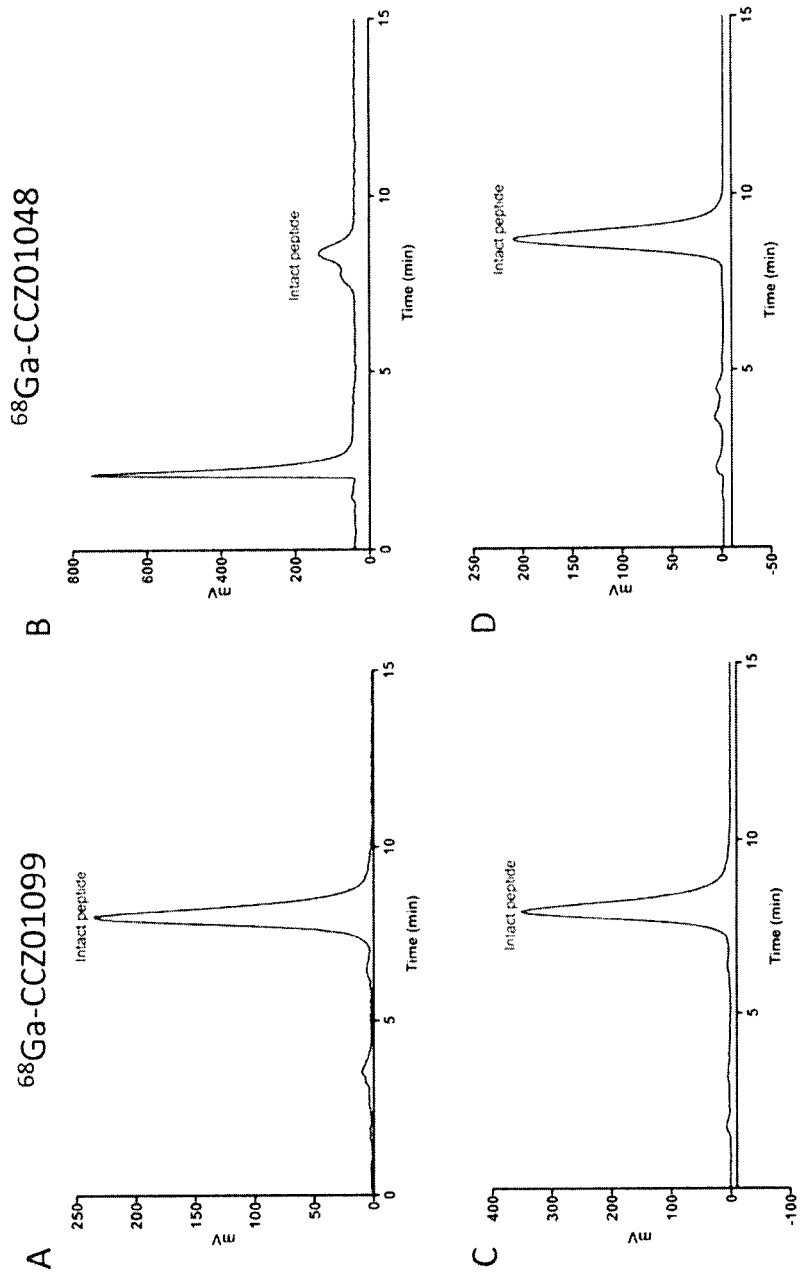
FIG. 2 shows representative radio-HPLC chromatograms of in vivo urine stability of compounds [$^{68}$Ga]Ga-CCZ01099 (A) and [$^{68}$Ga]Ga-CCZ01048 (B) at 1 h post-injection (p.i.), and quality control for compounds [$^{68}$Ga]Ga-CCZ01099 (C) and [$^{68}$Ga]Ga-CCZ01048 (D).

All animal experiments were conducted in according to the guidelines established by Canadian Council on Animal Care and approved by Animal Ethics Committee of the University of British Columbia. Mice were housed under pathogen-free conditions and kept on twelve hours light and twelve hours dark cycle in the Animal Research Centre, BC Cancer Research Centre, Vancouver, Canada. C57BL/6J mice were anesthetized by inhalation with 2% isoflurane in 2.0 L/min of oxygen, and approximately 4-6 MBq of [$^{68}$Ga] Ga-CCZ01099 or [$^{68}$Ga]Ga-CCZ01048 was injected intravenously. The mice were allowed to recover and roam freely in their cages. At 1 h post-injection (p.i.), the mice were euthanized by $CO_2$ inhalation and their urine was collected and analyzed on HPLC for metabolite using the conditions described above. The radio-HPLC traces are shown in FIG. 2. In vivo urine stability of [$^{68}$Ga]Ga-CCZ01099 and [$^{68}$Ga] Ga-CCZ01048 were 34.0±10.4% and ≥98.0% (n≥3), respectively. This demonstrated that with N-methylation greatly improved the in vivo stability of CCZ01099 compared to CCZ01048 lacking N-methylation.

Cell Culture and Tumour Implantation

The B16-F10 melanoma cell line (*Mus musculus*) used in the tumor model was obtained commercially from ATTC (CRL-6475). Cells were cultured in Dulbecco's Modified Eagle's Medium (DMEM, StemCell Technologies) supplemented by 10% FBS, 100 U/mL penicillin and 100 μg/mL streptomycin at 37° C. in a humidified incubator containing 5% $CO_2$. Cells grown to roughly 90% confluence were washed with sterile phosphate-buffered saline (lx PBS, pH 7.4), followed by trypsinization. For tumour implantation, C57BL/6J mice were anesthetized by inhalation with 2% isoflurane in 2.0 L/min of oxygen, $2×10^6$ B16-F10 cells were inoculated subcutaneously on right dorsal flank. Mice were imaged or used in biodistribution studies once the tumour reached 6-8 mm in diameter.

PET/CT Imaging

Figure 3:
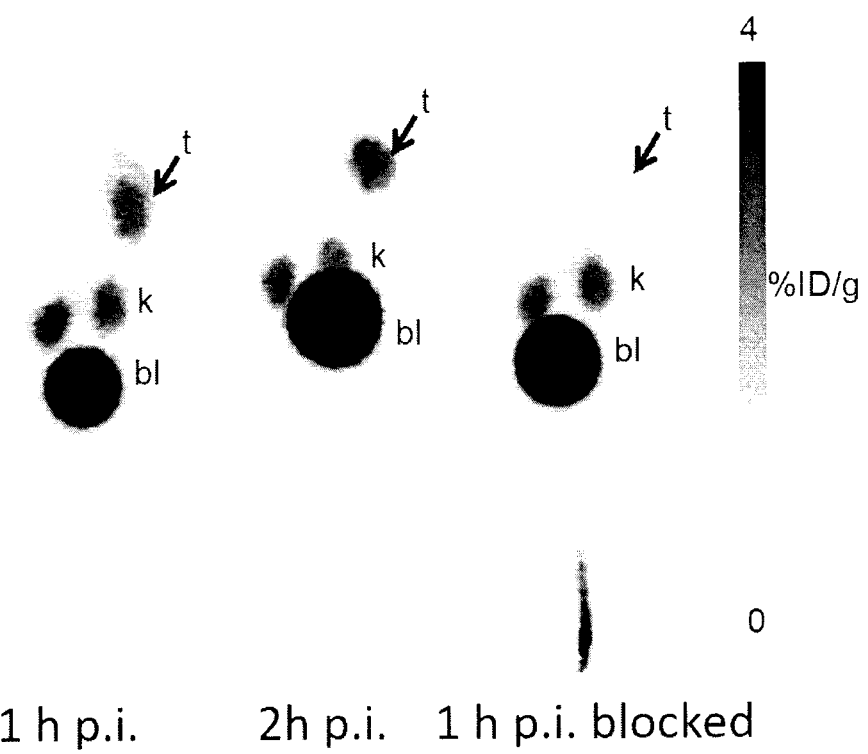
FIG. 3 shows reconstructed $^{68}$Ga-labeled CCZ01099 static PET images of C57BL/6J mice bearing B16-F10 tumours at 1 and 2 h post-injection (p.i.), as well as 1 h p.i. blocked with co-injection of 0.5 mg of MC1R-specific inhibitor BMS 470539 (Scale bar unit is percent injected dose per gram of tissue, % ID/g). t, tumour; k, kidney; bl, bladder.

PET imaging experiments were conducted using a preclinical micro PET/CT scanner (Siemens inveon). For static PET scan, each tumour bearing mouse was injected with 4-6 MBq of $^{68}$Ga-labeled CCZ01099 via tail vein under anesthesia. After the injection, mice were allowed to recover and roam freely in their cages. At 1 or 2 h p.i., the mice were sedated again with 2% isoflurane inhalation and positioned in the scanner, and kept warm by a heating pad. A 10 min baseline CT scan using 60 kV X-rays at 500 μA was obtained for localization and attenuation correction after segmentation for reconstructing the PET images. A single 12 min static PET scan was acquired following the CT scan. The mice were euthanized using $CO_2$ inhalation after imaging. FIG. 3 shows static PET images for $^{68}$Ga-labeled CCZ01099 at 1 h and 2 h p.i., as well as co-injection of 0.5 mg of MC1R-specific inhibitor BMS 470539 at 1 h p.i. Tumours were clearly visualized on the PET images with low normal tissue uptake (except for kidneys and bladder for tracer clearance) and minimal off-target radioactivity accumulation. In contrast, for the non-selective [$^{68}$Ga]Ga-CCZ01048, thyroid uptake was clearly observed on PET images (see Zhang et al., 2017 Theranostics 7(4):805-813)). In addition, tumour uptake was abolished with the co-injection of MC1R-specific inhibitor BMS 470539, confirming the tumour uptake was MC1R-mediated.

Biodistribution

Similar to PET/CT imaging, tumour-bearing mice were injected with 1-2 MBq of $^{68}$Ga-labeled CCZ01099 via tail vein under anesthesia with or without co-injection of 0.5 mg of MC1R-specific inhibitor BMS 470539. At 1 or 2 h p.i., the mice were anesthetized again, and euthanized by $CO_2$ inhalation. Blood was promptly withdrawn, and the organs of interest were harvested, rinsed with 1xPBS (pH 7.4), and blotted dry. Each organ was then weighed and the radioactivity of the collected tissue was measured using a Wallac WIZARD2 gamma counter (Perkin Elmer), normalized to the injected dose using a standard curve and expressed as the percentage of the injected dose per gram of tissue (% ID/g). Table 3 summarizes the biodistribution data of $^{68}$Ga-labeled CCZ01099 at 1 and 2 h p.i., as well as 1 h p.i. with co-injection of 0.5 mg of MC1R-specific inhibitor BMS 470539. Minimal background tissue radioactivity accumulation was observed, except for kidney, which is expected as the radiolabeled peptides were cleared through the renal pathway. Good tumour to background contrast was achieved at 1 h p.i., with tumour-to-muscle at 37.9±12.5 and tumour-to-blood at 9.19±3.19, and further improved to 125±29.6 and 27.7±5.34 at 2 h p.i., respectively. Tumour uptake was significantly reduced by 89% with the MC1R inhibitor, confirming the tumour uptake was MC1R-mediated.

TABLE 3

Biodistribution of $^{68}$Ga-labeled CCZ01099 in C57BL/6J mice bearing B16F10 mouse melanoma at 1 and 2 h p.i., blocking was performed by co-injection of 0.5 mg of MC1R-specific inhibitor BMS 470539 (Multiple t tests were performed, multiple comparisons were corrected using the Holm-Sidak method, ***p < 0.001, n ≥ 5). Values are in percentage of injected dose per gram of tissue (% ID/g, mean ± standard deviation).

| Tissue | 1 h p.i. unblocked | 2 h p.i. unblocked | 1 h p.i. blocked |
|---|---|---|---|
| B16F10 tumour | 6.12 ± 1.43 | 5.22 ± 1.30 | 0.60 ± 0.15*** |
| Blood | 0.70 ± 0.15 | 0.19 ± 0.01 | 0.27 ± 0.04 |
| Fat | 0.09 ± 0.04 | 0.02 ± 0.01 | 0.04 ± 0.02 |
| Seminal glands | 0.11 ± 0.05 | 0.04 ± 0.01 | 0.07 ± 0.03 |
| Testes | 0.21 ± 0.06 | 0.07 ± 0.01 | 0.10 ± 0.02 |
| Intestine | 0.37 ± 0.11 | 0.53 ± 0.38 | 0.17 ± 0.05 |
| Spleen | 0.35 ± 0.07 | 0.19 ± 0.03 | 0.52 ± 0.28 |
| Pancreas | 0.17 ± 0.04 | 0.07 ± 0.01 | 0.08 ± 0.01 |
| Stomach | 0.26 ± 0.15 | 0.20 ± 0.16 | 0.19 ± 0.12 |
| Liver | 0.54 ± 0.07 | 0.44 ± 0.08 | 0.38 ± 0.11 |
| Adrenal glands | 0.71 ± 0.67 | 0.33 ± 0.19 | 0.45 ± 0.29 |
| Kidneys | 5.98 ± 1.24 | 4.42 ± 0.55 | 2.62 ± 0.91*** |
| Heart | 0.26 ± 0.07 | 0.08 ± 0.01 | 0.13 ± 0.02 |
| Lungs | 0.74 ± 0.14 | 0.31 ± 0.05 | 0.34 ± 0.13 |
| Thyroid | 0.31 ± 0.08 | 0.16 ± 0.03 | 0.13 ± 0.05 |
| Bone | 0.32 ± 0.16 | 0.10 ± 0.03 | 0.17 ± 0.10 |
| Muscle | 0.17 ± 0.05 | 0.04 ± 0.00 | 0.08 ± 0.03 |
| Brain | 0.05 ± 0.04 | 0.01 ± 0.00 | 0.03 ± 0.02 |
| Tumour/muscle | 37.9 ± 12.5 | 125 ± 29.6 | 7.98 ± 1.35 |
| Tumour/blood | 9.19 ± 3.19 | 27.7 ± 5.34 | 2.24 ± 0.40 |
| Tumour/kidney | 1.05 ± 0.28 | 1.21 ± 0.44 | 0.26 ± 0.12 |

Example 2: CCZ01103, CCZ01104, CCZ01105, CCZ01106 and CCZ01114

Synthesis of CCZ01103, CCZ01104, CCZ01105, CCZ01106 and CCZ01114

Peptide synthesis was performed as described in Example 1. Five N-methylated αMSH analogues were synthesized. As shown below, CCZ01103 has 3 N-methylations, CCZ01104, CCZ01105 and CCZ01106 each have 2 N-methylations, and CCZ01114 has a single V-methyl at ion.

CCZ01103

DOTA-Pip-Nle-cyclo[Asp-His-D-Phe-(N-Me-Arg)-(N-Me-Trp)-(N-Me-Lys)]—NH$_2$

CCZ01104

DOTA-Pip-Nle-cyclo[Asp-His-D-Phe-(N-Me-Arg)-(N-Me-Trp)-Lys]-NH$_2$

CCZ01105

DOTA-Pip-Nle-cyclo[Asp-His-D-Phe-Arg-(N-Me-Trp)-(N-Me-Lys)]—NH$_2$

CCZ01106

DOTA-Pip-Nle-cyclo[Asp-His-D-Phe-(N-Me-Arg)-Trp-(N-Me-Lys)]—NH$_2$

CCZ01114

DOTA-Pip-Nle-cyclo[Asp-His-D-Phe-(N-Me-Arg)-Trp-Lys]-NH$_2$

In Vitro Competition Binding Assays

Figure 4:
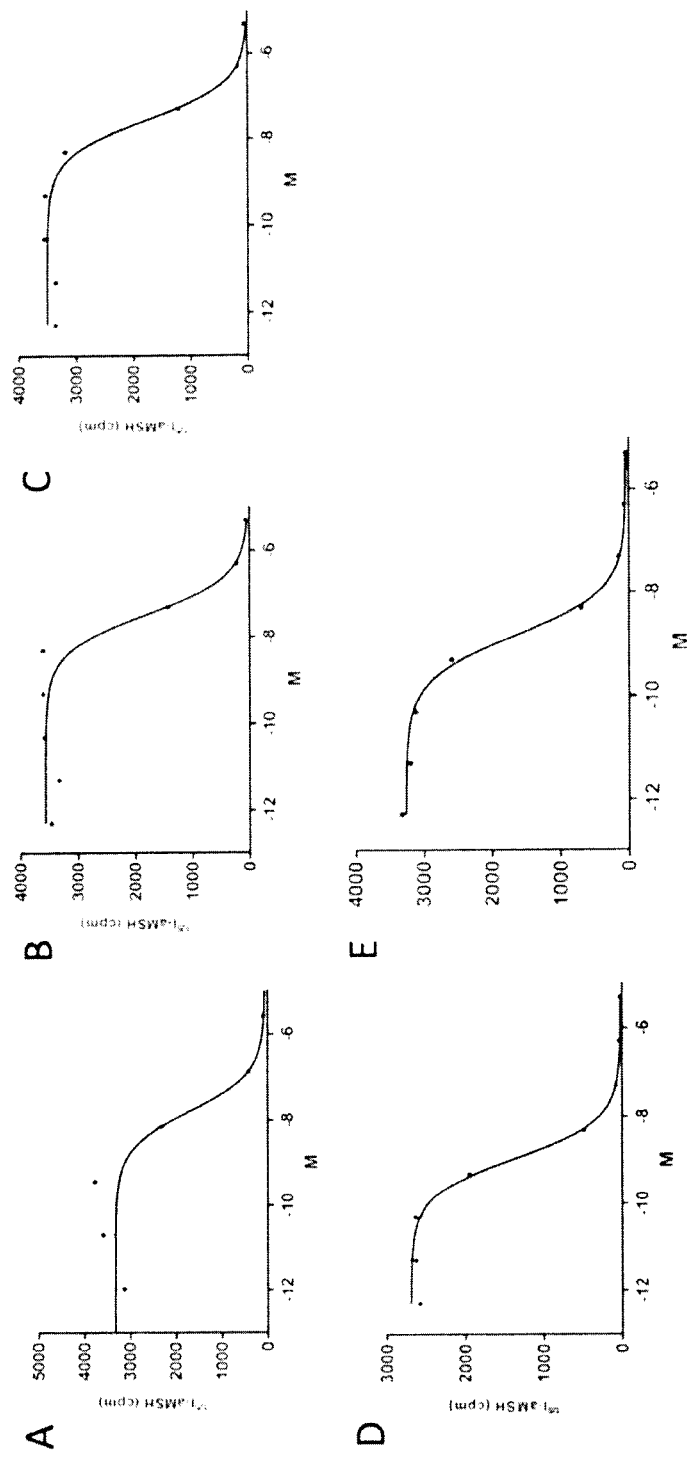
FIG. 4 shows representative competitive binding curves for compounds $^{nat}$Ga-CCZ01103 (A), $^{nat}$Ga-CCZ01104 (B), $^{nat}$Ga-CCZ01105 (C), $^{nat}$Ga-CCZ01106 and $^{nat}$Ga-CCZ01114 (E) on B16-F10 cells.

In vitro competitive binding assays were performed using B16-F10 cells and the cell culture method described in Example 1. 500,000 cells/well were seeded onto a 24 well poly-D-lysine coated plate (Corning) overnight. Growth media was removed, and reaction buffer containing 4.8 mg/mL HEPES, 1,000 g/mL penicillin/streptavidin and 2 mg/mL BSA was added, and allowed to incubate with cells at 37° C. for at least an hour. Peptide of interest and $^{125}$I-[Nle$^4$, D-Phe$^7$]-alpha-MSH (Perkin Elmer) were added to each well. The binding of $^{125}$I-[Nle$^4$, D-Phe$^7$]-alpha-MSH was competed by non-radioactive gallium coupled CCZ01103, CCZ01104, CCZ01105, CCZ01106 or CCZ01114 at increasing concentrations from 0.5 pmol/mL to 5 mol/L. The reaction mixture was incubated at 25° C. with moderate shaking for 1 h. After the incubation, the reaction mixture was removed, and cells were washed with ice-cold PBS twice. 0.25% Trypsin solution was used to harvest the cells and radioactivity was measured using a Wallac WIZARD2 gamma counter (Perkin Elmer). The inhibition constants (Ki) are summarized in Table 4. The representative binding curves are shown in FIG. 4. CCZ01106 and CCZ01114 showed the highest binding affinity.

TABLE 4

Inhibition constants (K$_i$) of $^{nat}$Ga-CCZ01103, $^{nat}$Ga-CCZ01104, $^{nat}$Ga-CCZ01105, $^{nat}$Ga-CCZ01106 and $^{nat}$Ga-CCZ01114 (n ≥ 3) on B16F10 cells.

|  | Ki (nM) |
|---|---|
| $^{nat}$Ga-CCZ01103 | 16.0 ± 1.5 |
| $^{nat}$Ga-CCZ01104 | 35.9 ± 3.2 |
| $^{nat}$Ga-CCZ01105 | 31.0 ± 3.8 |
| $^{nat}$Ga-CCZ01106 | 1.5 ± 0.1 |
| $^{nat}$Ga-CCZ01114 | 1.5 ± 0.1 |

In Vivo Stability

The in vivo stability tests in mouse urine were performed as described in Example 1. The in vivo stability of $^{68}$Ga-labeled CCZ01103, CCZ01104, CCZ01105, CCZ01106 or CCZ01114 is summarized in Table 5. From the data in Example 1, the four TV-methylated αMSH analogue was highly stable compared to non-TV-methylated CCZ01048. With systematic reduction in the number of N-methylations for the αMSH analogues, a decrease in in vivo stability was observed. Among the five αMSH analogues tested here, CCZ01106 showed the best balance, having both high binding affinity (1.5±0.1 nM) and high in vivo stability (82.5±1.8%).

TABLE 5

In vivo stability of [$^{68}$Ga]Ga-CCZ01103, [$^{68}$Ga]Ga-CCZ01104,
[$^{68}$Ga]Ga-CCZ01105, [$^{68}$Ga]Ga-CCZ01106 and [$^{68}$Ga]Ga-CCZ01114
in mouse urine at 1 h p.i. (n = 3). N-methylated amino acids are underlined.

| | Peptide sequence | Intact tracer (%) |
|---|---|---|
| [$^{68}$Ga]Ga-CCZ01103 | DOTA-Pip-Nle-c[D-H-f-R-W-K]-NH$_2$ | 92.6 ± 1.6 |
| [$^{68}$Ga]Ga-CCZ01104 | DOTA-Pip-Nle-c[D-H-f-R-W-K]-NH$_2$ | 92.5 ± 2.1 |
| [$^{68}$Ga]Ga-CCZ01105 | DOTA-Pip-Nle-c[D-H-f-R-W-K]-NH$_2$ | 65.8 ± 2.9 |
| [$^{68}$Ga]Ga-CCZ01106 | DOTA-Pip-Nle-c[D-H-f-R-W-K]-NH$_2$ | 82.5 ± 1.8 |
| [$^{68}$Ga]Ga-CCZ01114 | DOTA-Pip-Nle-c[D-H-f-R-W-K]-NH$_2$ | 41.4 ± 3.9 |

Example 3: CCZ01082. CCZ01088 and CCZ01118

Synthesis of CCZ01082. CCZ01088 and CCZ01118

Three αMSH analogues, CCZ01082, CCZ01088 and CCZ01118, were synthesized, and correspond to CCZ01048, CCZ01099 and CCZ01106, respectively, modified to have a [4-(p-iodophenyl)butanoyl]-Glu albumin binder group. The chemical structure of CCZ01118 ([4-(p-iodophenyl)butanoyl]-Glu-Lys(DOTA)-Pip-Nle-cyclo[Asp-His-D-Phe-N-Me-Arg-Trp-N-Me-Lys]-NH$_2$) is shown below:

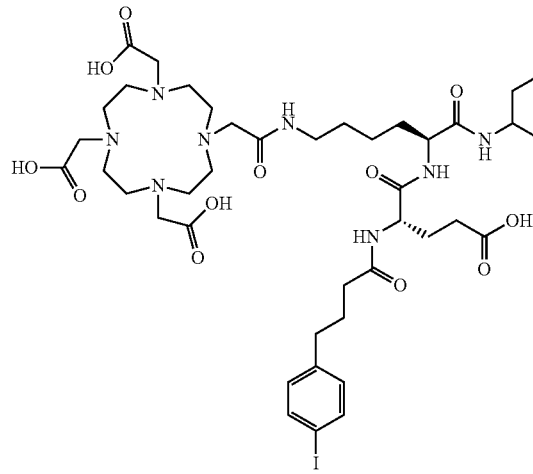
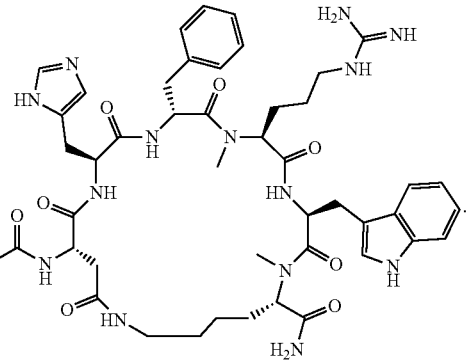

To synthesize these analogues with the albumin binder group, after coupling the Fmoc-Pip-OH to the peptide sequence as described above, Fmoc is deprotected, followed by sequential coupling of Fmoc-Lys(ivDde)-OH, Fmoc-Glu(tBu)-OH, and 4-(p-iodophenyl)butyric acid in presence of HATU, HOAt and DIEA. Subsequently, ivDde is removed by treatment with 2% hydrazine in DMF, followed by conjugation of the DOTA chelator.

Cell Culture and Tumour Implantation

The B16-F10 mouse melanoma cells were cultured and inoculated in mice as described in Example 1.

SPECT/CT Imaging and Biodistribution Studies

Figure 5:
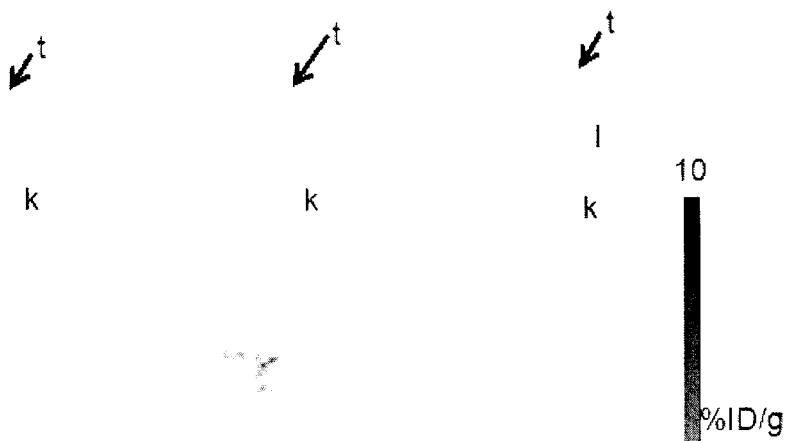
FIG. 5 shows reconstructed SPECT images of $^{177}$Lu-labeled αMSH analogues in C57BL/6J mice bearing B16-F10 tumours at 24 h p.i. Peptides in the lower panel are the [4-(p-iodophenyl)butanoyl]-Glu albumin binder conjugated counterparts to the ones in the upper panel. (Scale bar unit is % ID/g). t, tumour; k, kidney; l, liver.
Figure 5:
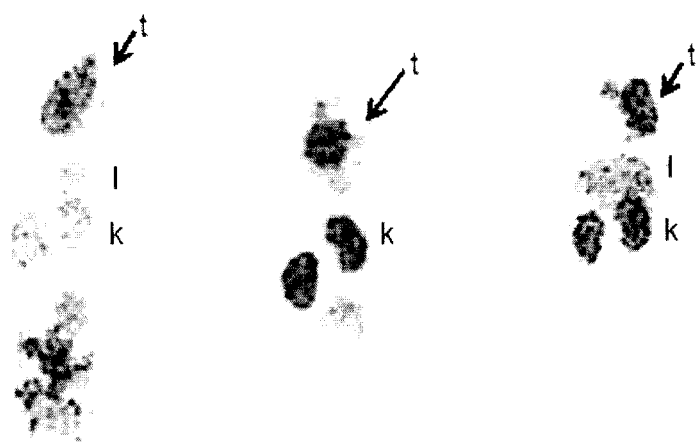

SPECT/CT imaging experiments were conducted using a preclinical U-SPECT-II/CT scanner (MILabs). For SPECT scans, each tumour-bearing mouse was injected with approximately 37 MBq of $^{177}$Lu-labeled αMSH analogues via tail vein under anesthesia. After the injection, mice were allowed to recover and roam freely in their cages. At 1, 4, 24, and 120 h p.i., the mice were sedated again with 2% isoflurane inhalation and positioned in the scanner, and kept warm by a heating pad. A 3 min CT scan was conducted to acquire anatomical information, followed by a 60 min static emission scan in list mode with an extra ultrahigh-sensitivity multipinhole mouse collimator. The images were reconstructed using the ordered subset expectation maximization algorithm (4 iterations, 32 subsets) and a 1 mm post-processing Gaussian filter. The radioactivity in the SPECT scans were decay corrected to the injection time in the PMOD software, and converted to DICOM for quantitation and visualization in the Inveon Research Workplace software (Siemens). SPECT images of all six αMSH analogues radiolabeled with $^{177}$Lu in mice bearing B16F10 mouse melanoma at 24 h p.i. are showing in FIG. 5. With the albumin binder (lower panel), much higher tumour uptake was observed for the αMSH analogues. With [$^{177}$Lu]Lu-CCZ01118, the mouse melanoma was clearly visualized with SPECT imaging at 24 h p.i. The sustained tumour uptake is particularly beneficial for radioligand therapy.

For biodistribution studies, approximately 1-2 MBq of $^{177}$Lu-labeled αMSH analogues via tail vein under anesthesia. At 1, 4, 24, and 120 h p.i., the mice were euthanized by CO$_2$ inhalation. Organs/tissues were harvested and the radioactivity was measured as described in Example 1. The biodistribution data for all six αMSH analogues are summarized in Tables 6-11. The tumour uptake values for all six αMSH analogues are summarized in Table 12. Based on the results for CCZ01106 in Example 2, the albumin binder containing analogue, CCZ01118 showed the most improvement in tumour uptake retention.

TABLE 6

Biodistribution of $^{177}$Lu-labeled CCZ01048 in C57BL/6J mice bearing B16F10 mouse melanoma at 1, 4, 24 and 120 h p.i. (n = 5). Values are in % ID/g (mean ± standard deviation).

| Tissue | 1 h p.i. | 4 h p.i. | 24 h p.i. | 120 h p.i. |
|---|---|---|---|---|
| B16F10 tumour | 16.3 ± 3.75 | 16.7 ± 3.86 | 4.39 ± 1.36 | 0.41 ± 0.21 |
| Blood | 0.50 ± 0.02 | 0.09 ± 0.02 | 0.01 ± 0.00 | 0.00 ± 0.00 |
| Urine | 110 ± 81.9 | 13.8 ± 10.2 | 1.99 ± 1.39 | 0.22 ± 0.05 |
| Fat | 0.05 ± 0.01 | 0.02 ± 0.01 | 0.02 ± 0.01 | 0.01 ± 0.00 |
| Seminal glands | 0.16 ± 0.03 | 0.08 ± 0.03 | 0.06 ± 0.03 | 0.01 ± 0.01 |
| Testes | 0.27 ± 0.04 | 0.16 ± 0.02 | 0.11 ± 0.02 | 0.04 ± 0.01 |
| Intestine | 0.33 ± 0.06 | 0.49 ± 0.46 | 0.27 ± 0.23 | 0.04 ± 0.03 |
| Spleen | 0.29 ± 0.02 | 0.22 ± 0.06 | 0.20 ± 0.03 | 0.07 ± 0.02 |
| Pancreas | 0.12 ± 0.01 | 0.05 ± 0.01 | 0.04 ± 0.01 | 0.02 ± 0.00 |
| Stomach | 0.59 ± 0.16 | 0.56 ± 0.08 | 0.70 ± 0.23 | 0.08 ± 0.05 |
| Liver | 0.54 ± 0.08 | 0.48 ± 0.10 | 0.34 ± 0.05 | 0.16 ± 0.04 |
| Adrenal glands | 0.38 ± 0.38 | 0.08 ± 0.05 | 0.12 ± 0.08 | 0.07 ± 0.04 |
| Kidneys | 5.36 ± 0.32 | 4.89 ± 1.06 | 1.78 ± 0.32 | 0.36 ± 0.09 |
| Heart | 0.18 ± 0.02 | 0.05 ± 0.02 | 0.03 ± 0.00 | 0.01 ± 0.00 |
| Lungs | 0.73 ± 0.40 | 0.20 ± 0.04 | 0.12 ± 0.12 | 0.02 ± 0.01 |
| Thyroid | 2.57 ± 0.62 | 2.16 ± 0.40 | 1.24 ± 0.32 | 0.15 ± 0.10 |
| Bone | 0.19 ± 0.01 | 0.11 ± 0.03 | 0.10 ± 0.03 | 0.04 ± 0.02 |
| Muscle | 0.13 ± 0.02 | 0.03 ± 0.01 | 0.02 ± 0.01 | 0.01 ± 0.00 |
| Brain | 0.02 ± 0.00 | 0.01 ± 0.00 | 0.01 ± 0.00 | 0.01 ± 0.00 |
| Tumour/muscle | 126 ± 34.1 | 561 ± 208 | 239 ± 108 | 80.9 ± 28.1 |
| Tumour/blood | 32.4 ± 7.58 | 206 ± 73.7 | 530 ± 45.1 | 233 ± 57.8 |
| Tumour/kidney | 3.04 ± 0.63 | 3.65 ± 1.48 | 2.25 ± 0.15 | 1.14 ± 0.65 |

TABLE 7

Biodistribution of $^{177}$Lu-labeled CCZ01082 in C57BL/6J mice bearing B16F10 mouse melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| B16F10 tumour | 13.3 ± 3.34 | 20.8 ± 5.37 | 7.59 ± 1.70 | 0.79 ± 0.39 |
| Blood | 8.32 ± 2.74 | 2.82 ± 1.17 | 0.33 ± 0.57 | 0.03 ± 0.04 |
| Urine | 87.9 ± 48.2 | 113 ± 29.4 | 6.11 ± 1.66 | 1.21 ± 0.21 |
| Fat | 0.61 ± 0.23 | 0.39 ± 0.12 | 0.10 ± 0.13 | 0.05 ± 0.05 |
| Seminal glands | 0.48 ± 0.13 | 0.32 ± 0.15 | 0.10 ± 0.04 | 0.04 ± 0.02 |
| Testes | 1.30 ± 0.40 | 0.75 ± 0.26 | 0.32 ± 0.17 | 0.20 ± 0.11 |
| Intestine | 1.34 ± 0.28 | 2.91 ± 4.94 | 0.43 ± 0.32 | 0.08 ± 0.07 |
| Spleen | 2.10 ± 1.03 | 1.46 ± 0.67 | 1.05 ± 0.45 | 0.65 ± 0.34 |
| Pancreas | 1.14 ± 0.32 | 0.52 ± 0.27 | 0.17 ± 0.19 | 0.09 ± 0.05 |
| Stomach | 0.89 ± 0.50 | 1.65 ± 2.22 | 1.17 ± 0.77 | 0.19 ± 0.21 |
| Liver | 3.45 ± 0.31 | 3.83 ± 0.28 | 2.41 ± 0.34 | 0.90 ± 0.12 |
| Adrenal glands | 2.62 ± 1.48 | 1.31 ± 0.56 | 0.41 ± 0.35 | 0.33 ± 0.23 |
| Kidneys | 11.7 ± 5.52 | 11.6 ± 5.03 | 8.63 ± 6.40 | 1.98 ± 0.72 |
| Heart | 2.03 ± 0.68 | 0.80 ± 0.32 | 0.18 ± 0.17 | 0.09 ± 0.04 |
| Lungs | 5.11 ± 2.81 | 2.46 ± 0.54 | 0.42 ± 0.34 | 0.54 ± 0.87 |
| Thyroid | 3.41 ± 0.51 | 3.86 ± 0.39 | 4.03 ± 1.33 | 0.86 ± 0.31 |
| Bone | 0.84 ± 0.19 | 0.51 ± 0.11 | 0.31 ± 0.08 | 0.17 ± 0.07 |
| Muscle | 0.79 ± 0.22 | 0.39 ± 0.10 | 0.06 ± 0.05 | 0.03 ± 0.02 |
| Brain | 0.13 ± 0.03 | 0.06 ± 0.02 | 0.01 ± 0.02 | 0.01 ± 0.01 |
| Tumour/muscle | 18.7 ± 8.13 | 57.7 ± 22.4 | 167 ± 88.7 | 38.9 ± 24.0 |
| Tumour/blood | 1.82 ± 0.82 | 8.59 ± 4.19 | 87.6 ± 47.8 | 52.9 ± 41.3 |
| Tumour/kidney | 1.41 ± 0.71 | 2.05 ± 0.86 | 1.14 ± 0.50 | 0.42 ± 0.18 |

TABLE 8

Biodistribution of $^{177}$Lu-labeled CCZ01099 in C57BL/6J mice bearing B16F10 mouse melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| B16F10 tumour | 4.49 ± 1.89 | 4.42 ± 0.64 | 2.04 ± 0.46 | 0.49 ± 0.30 |
| Blood | 0.48 ± 0.22 | 0.05 ± 0.01 | 0.01 ± 0.00 | 0.00 ± 0.00 |
| Urine | 227 ± 115 | 49.1 ± 39.7 | 0.46 ± 0.31 | 0.09 ± 0.06 |
| Fat | 0.06 ± 0.02 | 0.01 ± 0.00 | 0.01 ± 0.00 | 0.01 ± 0.00 |
| Seminal glands | 0.06 ± 0.02 | 0.02 ± 0.00 | 0.01 ± 0.00 | 0.00 ± 0.00 |
| Testes | 0.13 ± 0.02 | 0.03 ± 0.00 | 0.03 ± 0.00 | 0.02 ± 0.01 |
| Intestine | 0.25 ± 0.03 | 0.12 ± 0.06 | 0.23 ± 0.28 | 0.12 ± 0.16 |
| Spleen | 0.24 ± 0.08 | 0.13 ± 0.04 | 0.12 ± 0.02 | 0.07 ± 0.01 |
| Pancreas | 0.13 ± 0.05 | 0.03 ± 0.01 | 0.03 ± 0.00 | 0.02 ± 0.00 |
| Stomach | 0.13 ± 0.02 | 0.59 ± 1.14 | 0.53 ± 0.48 | 0.12 ± 0.16 |
| Liver | 0.41 ± 0.11 | 0.34 ± 0.10 | 0.32 ± 0.13 | 0.19 ± 0.02 |
| Adrenal glands | 0.39 ± 0.13 | 0.19 ± 0.06 | 0.10 ± 0.04 | 0.03 ± 0.03 |
| Kidneys | 4.15 ± 0.99 | 4.32 ± 2.06 | 1.61 ± 0.29 | 0.50 ± 0.02 |
| Heart | 0.17 ± 0.06 | 0.04 ± 0.01 | 0.03 ± 0.00 | 0.02 ± 0.00 |
| Lungs | 0.54 ± 0.20 | 0.17 ± 0.06 | 0.07 ± 0.02 | 0.04 ± 0.01 |
| Thyroid | 0.22 ± 0.09 | 0.07 ± 0.01 | 0.06 ± 0.01 | 0.05 ± 0.01 |
| Bone | 0.13 ± 0.03 | 0.06 ± 0.02 | 0.04 ± 0.01 | 0.02 ± 0.01 |
| Muscle | 0.10 ± 0.04 | 0.02 ± 0.00 | 0.01 ± 0.00 | 0.01 ± 0.00 |
| Brain | 0.02 ± 0.00 | 0.01 ± 0.00 | 0.00 ± 0.00 | 0.00 ± 0.00 |
| Tumour/muscle | 45.0 ± 14.0 | 227 ± 72.9 | 197 ± 64.7 | 63.0 ± 33.6 |
| Tumour/blood | 9.65 ± 2.82 | 91.1 ± 50.2 | 171.7 ± 84.5 | 331 ± 206 |
| Tumour/kidney | 1.08 ± 0.33 | 1.16 ± 0.35 | 1.27 ± 0.21 | 0.96 ± 0.55 |

TABLE 9

Biodistribution of $^{177}$Lu-labeled CCZ01088 in C57BL/6J mice bearing B16F10 mouse melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| B16F10 tumour | 10.6 ± 2.95 | 10.9 ± 2.22 | 5.50 ± 2.36 | 0.88 ± 0.58 |
| Blood | 7.41 ± 1.64 | 1.44 ± 0.39 | 0.09 ± 0.02 | 0.01 ± 0.00 |
| Urine | 322 ± 306 | 106 ± 97.1 | 3.17 ± 1.25 | 0.51 ± 0.21 |
| Fat | 0.65 ± 0.37 | 0.16 ± 0.07 | 0.06 ± 0.04 | 0.03 ± 0.01 |
| Seminal glands | 0.52 ± 0.15 | 0.14 ± 0.04 | 0.08 ± 0.07 | 0.04 ± 0.03 |
| Testes | 1.11 ± 0.13 | 0.33 ± 0.08 | 0.17 ± 0.01 | 0.11 ± 0.01 |
| Intestine | 1.39 ± 0.37 | 0.37 ± 0.11 | 0.18 ± 0.03 | 0.43 ± 0.55 |
| Spleen | 1.99 ± 0.38 | 0.83 ± 0.10 | 1.00 ± 0.35 | 0.30 ± 0.12 |
| Pancreas | 1.23 ± 0.18 | 0.31 ± 0.10 | 0.10 ± 0.01 | 0.06 ± 0.01 |
| Stomach | 1.20 ± 0.45 | 0.26 ± 0.14 | 0.31 ± 0.17 | 1.83 ± 2.70 |
| Liver | 2.72 ± 0.27 | 1.98 ± 0.41 | 4.70 ± 3.76 | 0.55 ± 0.18 |
| Adrenal glands | 3.69 ± 2.09 | 0.88 ± 0.41 | 0.62 ± 0.34 | 0.34 ± 0.23 |
| Kidneys | 13.2 ± 3.61 | 13.53 ± 3.47 | 8.10 ± 2.24 | 1.85 ± 0.57 |
| Heart | 1.84 ± 0.31 | 0.40 ± 0.10 | 0.13 ± 0.02 | 0.07 ± 0.02 |
| Lungs | 5.51 ± 1.75 | 2.34 ± 1.21 | 1.19 ± 0.81 | 0.10 ± 0.05 |
| Thyroid | 1.68 ± 0.26 | 0.51 ± 0.13 | 0.24 ± 0.04 | 0.15 ± 0.03 |
| Bone | 0.98 ± 0.12 | 0.30 ± 0.08 | 0.23 ± 0.04 | 0.13 ± 0.09 |
| Muscle | 0.76 ± 0.14 | 0.17 ± 0.04 | 0.06 ± 0.02 | 0.03 ± 0.01 |
| Brain | 0.13 ± 0.02 | 0.04 ± 0.02 | 0.02 ± 0.01 | 0.01 ± 0.01 |
| Tumour/muscle | 13.8 ± 2.48 | 65.4 ± 13.7 | 104 ± 53.0 | 35.6 ± 22.4 |
| Tumour/blood | 1.42 ± 0.20 | 7.97 ± 2.18 | 60.6 ± 23.8 | 84.4 ± 47.2 |
| Tumour/kidney | 0.80 ± 0.09 | 0.85 ± 0.24 | 0.68 ± 0.22 | 0.45 ± 0.21 |

TABLE 10

Biodistribution of $^{177}$Lu-labeled CCZ01106 in C57BL/6J mice bearing B16F10 mouse melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| B16F10 tumour | 8.25 ± 1.94 | 7.81 ± 2.16 | 3.45 ± 0.30 | 0.49 ± 0.36 |
| Blood | 0.49 ± 0.22 | 0.02 ± 0.00 | 0.01 ± 0.00 | 0.00 ± 0.00 |
| Urine | 222 ± 81.1 | 19.3 ± 4.21 | 0.94 ± 0.48 | 0.15 ± 0.07 |
| Fat | 0.05 ± 0.02 | 0.01 ± 0.01 | 0.01 ± 0.00 | 0.00 ± 0.00 |
| Seminal glands | 0.22 ± 0.35 | 0.02 ± 0.00 | 0.01 ± 0.00 | 0.01 ± 0.01 |
| Testes | 0.17 ± 0.06 | 0.04 ± 0.00 | 0.03 ± 0.00 | 0.02 ± 0.00 |
| Intestine | 0.45 ± 0.20 | 0.11 ± 0.06 | 0.13 ± 0.04 | 0.06 ± 0.07 |
| Spleen | 0.38 ± 0.11 | 0.24 ± 0.03 | 0.20 ± 0.04 | 0.11 ± 0.01 |
| Pancreas | 0.15 ± 0.05 | 0.03 ± 0.00 | 0.03 ± 0.01 | 0.01 ± 0.00 |
| Stomach | 0.36 ± 0.22 | 0.11 ± 0.02 | 0.42 ± 0.18 | 0.10 ± 0.08 |
| Liver | 0.88 ± 0.16 | 0.81 ± 0.08 | 0.58 ± 0.14 | 0.34 ± 0.03 |
| Adrenal glands | 0.54 ± 0.28 | 0.13 ± 0.06 | 0.23 ± 0.18 | 0.02 ± 0.02 |
| Kidneys | 4.79 ± 0.92 | 3.31 ± 0.66 | 1.24 ± 0.46 | 0.36 ± 0.05 |
| Heart | 0.19 ± 0.07 | 0.03 ± 0.00 | 0.02 ± 0.00 | 0.01 ± 0.00 |
| Lungs | 0.60 ± 0.19 | 0.14 ± 0.04 | 0.06 ± 0.02 | 0.01 ± 0.01 |
| Thyroid | 0.43 ± 0.11 | 0.27 ± 0.06 | 0.17 ± 0.01 | 0.05 ± 0.02 |
| Bone | 0.18 ± 0.04 | 0.07 ± 0.02 | 0.06 ± 0.01 | 0.04 ± 0.01 |
| Muscle | 0.12 ± 0.05 | 0.02 ± 0.01 | 0.01 ± 0.01 | 0.00 ± 0.00 |
| Brain | 0.02 ± 0.00 | 0.01 ± 0.00 | 0.01 ± 0.00 | 0.00 ± 0.00 |
| Tumour/muscle | 75.0 ± 29.8 | 452 ± 158 | 320 ± 91.8 | 117 ± 92.2 |
| Tumour/blood | 19.2 ± 8.25 | 414 ± 59.0 | 652 ± 101 | 466 ± 382 |
| Tumour/kidney | 1.75 ± 0.47 | 2.46 ± 0.87 | 3.08 ± 1.05 | 1.44 ± 1.14 |

TABLE 11

Biodistribution of $^{177}$Lu-labeled CCZ01118 in C57BL/6J mice bearing B16F10 mouse melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| B16F10 tumour | 24.4 ± 1.76 | 29.7 ± 5.23 | 18.4 ± 1.35 | 2.63 ± 0.21 |
| Blood | 6.87 ± 0.88 | 1.41 ± 0.60 | 0.05 ± 0.02 | 0.01 ± 0.00 |
| Urine | 158 ± 83.1 | 124 ± 8.40 | 4.39 ± 2.89 | 1.11 ± 0.72 |
| Fat | 0.43 ± 0.08 | 0.12 ± 0.03 | 0.03 ± 0.01 | 0.02 ± 0.01 |
| Seminal glands | 0.50 ± 0.11 | 0.15 ± 0.06 | 0.04 ± 0.01 | 0.02 ± 0.01 |
| Testes | 1.07 ± 0.11 | 0.40 ± 0.14 | 0.16 ± 0.02 | 0.10 ± 0.01 |
| Intestine | 1.20 ± 0.20 | 1.53 ± 2.04 | 0.21 ± 0.05 | 0.10 ± 0.04 |
| Spleen | 2.06 ± 0.21 | 1.02 ± 0.27 | 0.64 ± 0.09 | 0.35 ± 0.15 |
| Pancreas | 1.13 ± 0.24 | 0.31 ± 0.08 | 0.08 ± 0.02 | 0.05 ± 0.01 |
| Stomach | 0.74 ± 0.18 | 2.33 ± 4.11 | 0.42 ± 0.13 | 0.20 ± 0.09 |
| Liver | 3.65 ± 0.25 | 3.58 ± 0.85 | 2.59 ± 0.31 | 1.25 ± 0.51 |
| Adrenal glands | 2.90 ± 1.51 | 0.54 ± 0.48 | 0.20 ± 0.09 | 0.18 ± 0.06 |
| Kidneys | 12.0 ± 0.83 | 12.7 ± 3.58 | 6.32 ± 0.43 | 1.43 ± 0.31 |
| Heart | 1.93 ± 0.16 | 0.45 ± 0.19 | 0.08 ± 0.01 | 0.05 ± 0.00 |
| Lungs | 6.71 ± 3.02 | 2.34 ± 0.63 | 0.33 ± 0.08 | 0.14 ± 0.08 |
| Thyroid | 2.47 ± 0.26 | 1.66 ± 0.42 | 1.59 ± 0.15 | 1.03 ± 0.24 |
| Bone | 0.96 ± 0.18 | 0.29 ± 0.11 | 0.13 ± 0.03 | 0.12 ± 0.06 |
| Muscle | 0.75 ± 0.09 | 0.18 ± 0.09 | 0.03 ± 0.01 | 0.02 ± 0.04 |
| Brain | 0.13 ± 0.01 | 0.03 ± 0.02 | 0.01 ± 0.00 | 0.01 ± 0.00 |
| Tumour/muscle | 32.9 ± 2.98 | 194 ± 82.7 | 556 ± 108 | 173 ± 19.0 |
| Tumour/blood | 3.58 ± 0.31 | 24.3 ± 9.37 | 397 ± 123 | 339 ± 149 |
| Tumour/kidney | 2.04 ± 0.15 | 2.47 ± 0.80 | 2.91 ± 0.20 | 1.89 ± 0.37 |

TABLE 12

Summary of tumour uptake values of $^{177}$Lu-labeled αMSH analogues in C57BL/6J mice bearing B16F10 mouse melanoma at 1, 4, 24 and 120 h p.i. (n ≥ 5). Values are in % ID/g (mean ± standard deviation). Inhibition constants ($K_i$) of $^{nat}$Lu-conjugated peptides (n ≥ 3) on B16F10 cells.

| Peptide | $K_i$ (nM) | 1 h p.i. | 4 h p.i. | 24 h p.i. | 120 h p.i. |
|---|---|---|---|---|---|
| [$^{177}$Lu]Lu-CCZ01048 | 0.21 ± 0.03 | 16.3 ± 3.75 | 16.7 ± 3.86 | 4.39 ± 1.36 | 0.41 ± 0.21 |
| [$^{177}$Lu]Lu-CCZ01082 | 0.41 ± 0.02 | 13.3 ± 3.34 | 20.8 ± 5.37 | 7.59 ± 1.70 | 0.79 ± 0.39 |
| [$^{177}$Lu]Lu-CCZ01099 | 19.0 ± 1.50 | 4.49 ± 1.89 | 4.42 ± 0.64 | 2.04 ± 0.46 | 0.49 ± 0.30 |
| [$^{177}$Lu]Lu-CCZ01088 | 26.9 ± 6.20 | 10.6 ± 2.95 | 10.9 ± 2.22 | 5.50 ± 2.36 | 0.88 ± 0.58 |

TABLE 12-continued

Summary of tumour uptake values of $^{177}$Lu-labeled αMSH analogues in C57BL/6J mice bearing B16F10 mouse melanoma at 1, 4, 24 and 120 h p.i. (n ≥ 5). Values are in % ID/g (mean ± standard deviation). Inhibition constants ($K_i$) of $^{nat}$Lu-conjugated peptides (n ≥ 3) on B16F10 cells.

| Peptide | $K_i$ (nM) | 1 h p.i. | 4 h p.i. | 24 h p.i. | 120 h p.i. |
|---|---|---|---|---|---|
| [$^{177}$Lu]Lu-CCZ01106 | 2.15 ± 0.10 | 8.25 ± 1.94 | 7.81 ± 2.16 | 3.45 ± 0.30 | 0.49 ± 0.36 |
| [$^{177}$Lu]Lu-CCZ01118 | 1.42 ± 0.12 | 24.4 ± 1.76 | 29.7 ± 5.23 | 18.4 ± 1.35 | 2.63 ± 0.21 |

Example 4: CCZ01148 and CCZ01158 IDC-69 T1

Synthesis of CCZ01148 and CCZ01158

Two αMSH analogues, CCZ01148 and CCZ01158, were synthesized, with [4-(p-iodophenyl)butanoyl]-Gly and [4-(p-tolylphenyl)butanoyl]-Gly albumin binder groups, respectively. Peptide synthesis was performed as described in Example 3. The chemical structure of CCZ01158 ([4-(p-tolylphenyl)butanoyl]-Gly-Lys(DOTA)-Pip-Nle-cyclo[Asp-His-D-Phe-N-Me-Arg-Trp-N-Me-Lys]-NH$_2$) is shown below:

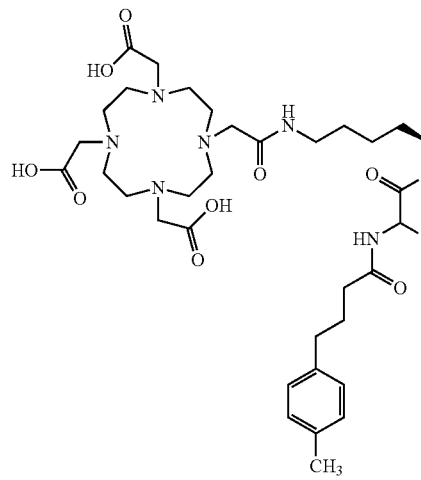
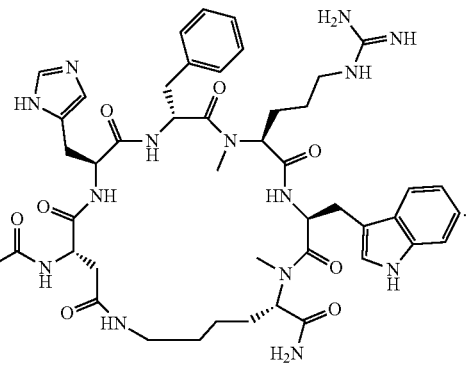

Cell Culture and Tumour Implantation

The SK-MEL-1 human melanoma cell line (HTB-67) was obtained commercially from ATCC. SK-MEL-1 cells were cultured in Eagle's Minimum Essential Medium (StemCell Technologies) under the same conditions as described in Example 1. Immunodeficient NOD.Cg-Rag1tm1Mom Il2rgtm1Wjl/SzJ (NRG) male mice were obtained from an in-house breeding colony at the BC Cancer Research Centre. For tumor implantation, male NRG mice were anesthetized by inhalation with 2% isoflurane, and 5 million SK-MEL-1 cells were inoculated subcutaneously on the right dorsal flank. Mice were used for imaging or biodistribution studies when the tumors reached 6-8 mm in diameter in 16-20 days.

SPECT/CT Imaging and Biodistribution Studies

Figure 6:
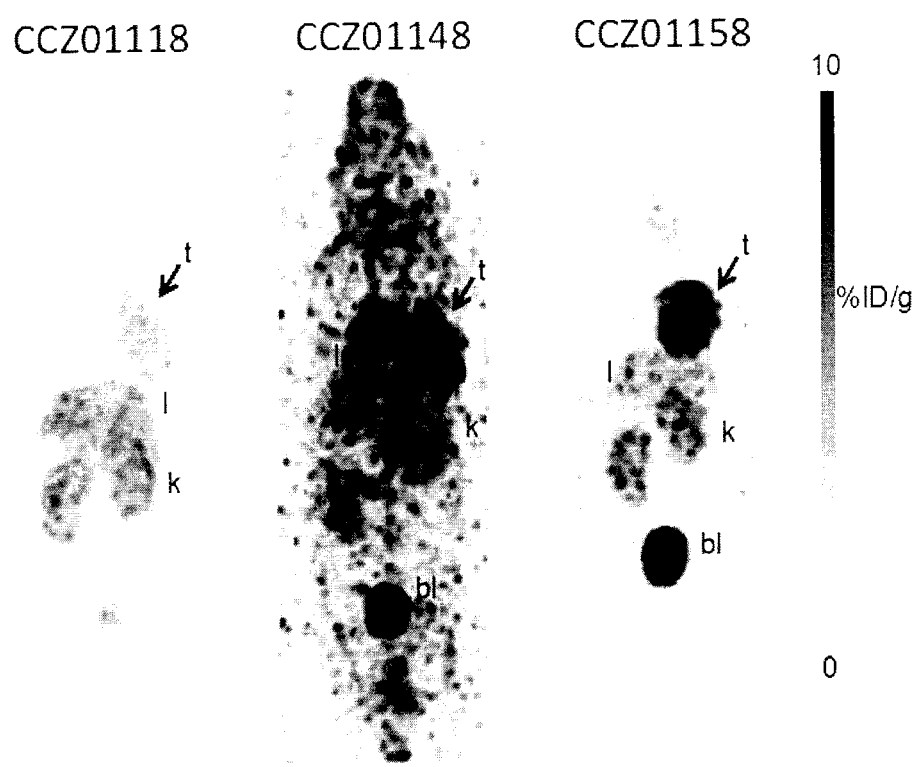
FIG. 6 shows reconstructed SPECT images of $^{177}$Lu-labeled αMSH analogues in NRG mice bearing SK-MEL-1 human melanoma at 24 h p.i. (Scale bar unit is % ID/g). t, tumour; k, kidney; l, liver.

SPECT/CT imaging experiments were conducted using the same conditions as described in Example 3. Due to the lower MC1R density on human melanoma cells compared to the mouse B16F10 cells, lower tumour uptake was observed in the SPECT images with [$^{177}$Lu]Lu-CCZ01118 at 24 h p.i. (FIG. 6). To increase the tumour uptake, two albumin binder groups, [4-(p-iodophenyl)butanoyl]-Gly (CCZ01148) and [4-(p-tolylphenyl)butanoyl]-Gly (CCZ01158), were tested and showed improved the tumour retention at 24 h p.i. Lower blood uptake was observed for CCZ01158.

Biodistribution studies were performed as described in Example 3. The biodistribution data for $^{177}$Lu-labeled CCZ01118, CCZ01148 and CCZ01158 are summarized in Tables 13, 14 and 15, respectively. [$^{177}$Lu]Lu-CCZ01158 was determined to be superior due to high and sustained tumour uptake, as well as superior tumour to background contrast compared to the other two analogues.

TABLE 13

Biodistribution of $^{177}$Lu-labeled CCZ01118 in NRG mice bearing SK-MEL-1 human melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| SK-MEL-1 tumour | 10.5 ± 3.29 | 14.0 ± 2.36 | 10.1 ± 2.13 | 4.8 ± 0.26 |
| Blood | 9.63 ± 0.78 | 2.46 ± 0.64 | 0.07 ± 0.03 | 0.02 ± 0.00 |
| Urine | 376 ± 154 | 154 ± 39.2 | 5.39 ± 1.23 | 1.12 ± 0.38 |
| Fat | 1.18 ± 0.08 | 0.45 ± 0.26 | 0.10 ± 0.05 | 0.08 ± 0.02 |
| Seminal glands | 0.59 ± 0.08 | 1.53 ± 2.82 | 0.06 ± 0.01 | 0.03 ± 0.01 |
| Testes | 1.58 ± 0.32 | 0.84 ± 0.20 | 0.22 ± 0.04 | 0.16 ± 0.04 |
| Intestine | 1.42 ± 0.22 | 0.79 ± 0.50 | 0.19 ± 0.03 | 0.08 ± 0.01 |
| Spleen | 3.06 ± 0.53 | 1.45 ± 0.33 | 1.20 ± 0.56 | 0.98 ± 0.29 |
| Pancreas | 1.40 ± 0.24 | 0.49 ± 0.08 | 0.10 ± 0.02 | 0.05 ± 0.00 |
| Stomach | 0.56 ± 0.10 | 0.44 ± 0.25 | 0.36 ± 0.20 | 0.13 ± 0.05 |
| Liver | 6.91 ± 1.09 | 5.77 ± 1.62 | 4.36 ± 1.11 | 2.42 ± 0.33 |
| Adrenal glands | 2.99 ± 2.15 | 1.21 ± 0.59 | 0.27 ± 0.13 | 0.30 ± 0.16 |
| Kidneys | 13.4 ± 2.53 | 12.76 ± 2.29 | 6.48 ± 1.25 | 1.69 ± 0.13 |
| Heart | 2.50 ± 0.30 | 0.84 ± 0.23 | 0.14 ± 0.04 | 0.08 ± 0.02 |
| Lungs | 6.59 ± 1.06 | 2.50 ± 0.67 | 0.86 ± 0.87 | 0.15 ± 0.12 |
| Thyroid | 4.03 ± 0.45 | 3.11 ± 0.46 | 2.49 ± 0.64 | 1.83 ± 0.21 |
| Bone | 1.10 ± 0.50 | 0.35 ± 0.08 | 0.15 ± 0.02 | 0.26 ± 0.39 |
| Muscle | 0.98 ± 0.12 | 0.36 ± 0.11 | 0.05 ± 0.01 | 0.02 ± 0.01 |
| Brain | 0.17 ± 0.02 | 0.06 ± 0.01 | 0.01 ± 0.00 | 0.01 ± 0.00 |
| Tumour/muscle | 10.6 ± 2.98 | 41.5 ± 9.8 | 201 ± 10.4 | 269 ± 79.1 |
| Tumour/blood | 1.08 ± 0.30 | 5.84 ± 0.96 | 165 ± 50.1 | 246 ± 28.6 |
| Tumour/kidney | 0.77 ± 0.12 | 1.10 ± 0.08 | 1.55 ± 0.10 | 2.85 ± 0.22 |

TABLE 14

Biodistribution of $^{177}$Lu-labeled CCZ01148 in NRG mice bearing SK-MEL-1 human melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| SK-MEL-1 tumour | 6.62 ± 1.37 | 9.46 ± 1.59 | 30.5 ± 2.72 | 26.5 ± 4.52 |
| Blood | 32.0 ± 5.85 | 22.7 ± 1.50 | 14.7 ± 0.98 | 1.93 ± 0.40 |
| Urine | 51.0 ± 21.8 | 11.2 ± 6.54 | 20.4 ± 7.69 | 6.46 ± 1.57 |
| Fat | 2.40 ± 0.39 | 2.69 ± 0.38 | 2.10 ± 0.53 | 1.13 ± 0.55 |
| Seminal glands | 1.81 ± 0.60 | 1.66 ± 0.51 | 1.22 ± 0.11 | 0.44 ± 0.12 |
| Testes | 4.23 ± 0.94 | 5.09 ± 0.82 | 4.89 ± 0.87 | 3.03 ± 0.37 |
| Intestine | 3.10 ± 1.00 | 2.26 ± 0.56 | 1.89 ± 0.29 | 0.54 ± 0.10 |
| Spleen | 5.65 ± 1.09 | 4.21 ± 1.31 | 6.19 ± 1.00 | 6.86 ± 2.08 |
| Pancreas | 3.09 ± 0.53 | 2.55 ± 0.15 | 2.27 ± 0.34 | 0.70 ± 0.13 |
| Stomach | 1.03 ± 0.45 | 1.02 ± 0.53 | 1.44 ± 0.28 | 0.47 ± 0.12 |
| Liver | 7.36 ± 1.58 | 7.11 ± 1.50 | 8.35 ± 1.86 | 4.38 ± 1.08 |
| Adrenal glands | 6.47 ± 2.97 | 5.69 ± 2.19 | 5.66 ± 1.07 | 4.04 ± 1.06 |
| Kidneys | 12.5 ± 3.49 | 9.78 ± 1.28 | 9.72 ± 1.38 | 4.08 ± 0.78 |
| Heart | 7.94 ± 1.58 | 5.71 ± 0.51 | 4.57 ± 0.51 | 1.40 ± 0.25 |
| Lungs | 17.6 ± 5.68 | 11.8 ± 2.51 | 9.06 ± 1.04 | 2.35 ± 0.54 |
| Thyroid | 7.45 ± 1.35 | 6.83 ± 0.84 | 11.6 ± 1.26 | 12.4 ± 2.26 |
| Bone | 1.98 ± 0.80 | 1.38 ± 0.29 | 1.21 ± 0.20 | 0.49 ± 0.17 |
| Muscle | 2.13 ± 0.40 | 1.96 ± 0.30 | 1.50 ± 0.19 | 0.31 ± 0.07 |
| Brain | 0.49 ± 0.06 | 0.39 ± 0.05 | 0.32 ± 0.03 | 0.13 ± 0.02 |
| Tumour/muscle | 3.11 ± 0.29 | 4.85 ± 0.53 | 20.5 ± 2.51 | 91.3 ± 35.8 |
| Tumour/blood | 0.21 ± 0.02 | 0.42 ± 0.04 | 2.08 ± 0.26 | 14 3 ± 4 40 |
| Tumour/kidney | 0.54 ± 0.07 | 0.96 ± 0.04 | 3.19 ± 0.46 | 6.57 ± 0.71 |

TABLE 15

Biodistribution of $^{177}$Lu-labeled CCZ01158 in NRG mice bearing SK-MEL-1 human melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| SK-MEL-1 tumour | 13.3 ± 2.94 | 24.3 ± 5.04 | 29.7 ± 4.29 | 19.3 ± 7.95 |
| Blood | 19.1 ± 3.57 | 10.8 ± 0.87 | 0.54 ± 0.24 | 0.04 ± 0.01 |
| Urine | 214 ± 57.6 | 258 ± 66.2 | 21.8 ± 4.60 | 3.56 ± 1.16 |
| Fat | 2.24 ± 0.49 | 1.85 ± 0.53 | 0.30 ± 0.07 | 0.20 ± 0.08 |
| Seminal glands | 1.80 ± 0.79 | 0.79 ± 0.13 | 0.15 ± 0.07 | 0.11 ± 0.06 |
| Testes | 2.99 ± 0.56 | 2.80 ± 0.12 | 0.92 ± 0.26 | 0.56 ± 0.25 |
| Intestine | 2.07 ± 0.42 | 1.32 ± 0.20 | 0.51 ± 0.52 | 0.28 ± 0.11 |

TABLE 15-continued

Biodistribution of $^{177}$Lu-labeled CCZ01158 in NRG mice bearing SK-MEL-1 human melanoma at 1, 4, 24 and 120 h p.i. (n ≥ 5). Values are in % ID/g (mean ± standard deviation).

| Tissue | 1 h p.i. | 4 h p.i. | 24 h p.i. | 120 h p.i. |
|---|---|---|---|---|
| Spleen | 3.90 ± 1.66 | 2.50 ± 0.50 | 1.89 ± 0.85 | 4.60 ± 3.88 |
| Pancreas | 1.87 ± 0.30 | 1.22 ± 0.08 | 0.27 ± 0.13 | 0.16 ± 0.07 |
| Stomach | 0.85 ± 0.29 | 0.66 ± 0.12 | 1.07 ± 1.42 | 1.24 ± 0.65 |
| Liver | 7.24 ± 2.38 | 6.37 ± 1.33 | 4.45 ± 2.60 | 3.85 ± 1.63 |
| Adrenal glands | 5.10 ± 1.69 | 3.54 ± 1.01 | 1.68 ± 0.93 | 1.36 ± 1.56 |
| Kidneys | 11.3 ± 2.81 | 11.28 ± 1.38 | 8.29 ± 1.94 | 3.26 ± 1.60 |
| Heart | 4.70 ± 0.70 | 2.84 ± 0.40 | 0.50 ± 0.20 | 0.30 ± 0.13 |
| Lungs | 11.2 ± 2.91 | 6.81 ± 1.45 | 1.55 ± 1.22 | 2.15 ± 2.57 |
| Thyroid | 5.57 ± 0.79 | 5.74 ± 0.74 | 5.04 ± 1.22 | 5.40 ± 2.58 |
| Bone | 1.36 ± 0.32 | 0.80 ± 0.24 | 0.24 ± 0.15 | 0.23 ± 0.09 |
| Muscle | 1.67 ± 0.35 | 1.03 ± 0.06 | 0.13 ± 0.04 | 0.05 ± 0.02 |
| Brain | 0.33 ± 0.10 | 0.20 ± 0.01 | 0.04 ± 0.02 | 0.03 ± 0.02 |
| Tumour/muscle | 7.99 ± 1.03 | 23.6 ± 4.32 | 245 ± 48.0 | 394 ± 42.9 |
| Tumour/blood | 0.69 ± 0.08 | 2.24 ± 0.36 | 62.8 ± 26.4 | 436 ± 64.7 |
| Tumour/kidney | 1.18 ± 0.11 | 2.14 ± 0.26 | 3.68 ± 0.60 | 6.17 ± 1.09 |

Radioligand Therapy with $^{177}$Lu-labeled CCZ01158

Figure 7:
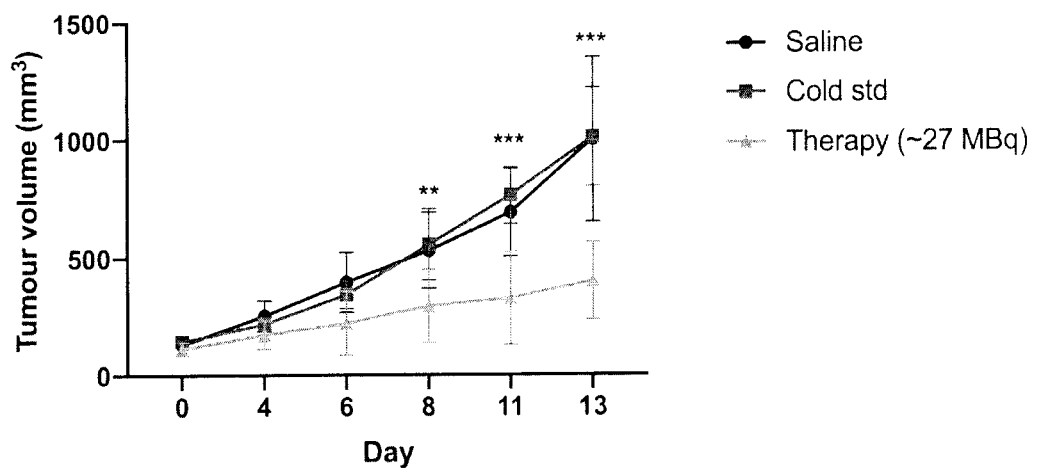
FIG. 7 shows an SK-MEL-1 human melanoma growth curve in three groups of mice injected with saline (control group, n=5), $^{nat}$Lu-CCZ01158 (cold std, n=4), and [$^{177}$Lu]Lu-CCZ01158 (26.7±3.6 MBq, n=4). Multiple t tests were performed, multiple comparisons were corrected using the Holm-Sidak method ( p<0.01, * p<0.001).
Figure 8:
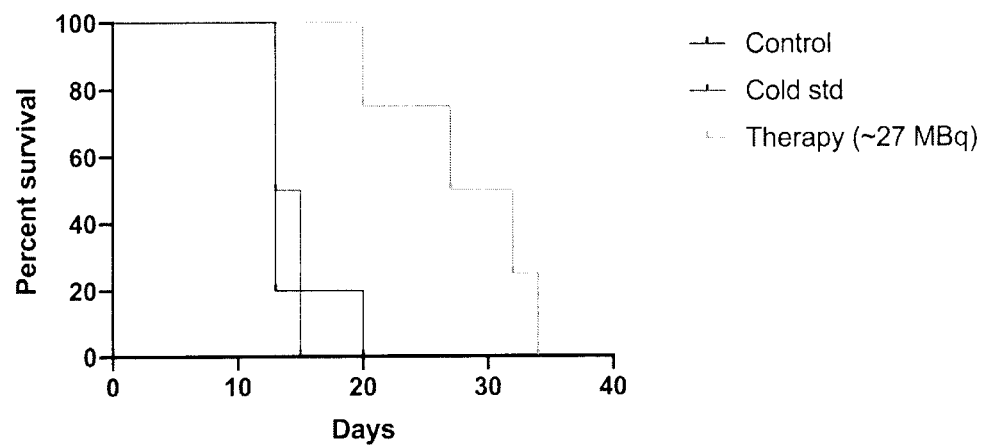
FIG. 8 shows a graph of overall survival for SK-MEL-1 tumour-bearing NRG mice injected with saline (control group, n=5), $^{nat}$Lu-CCZ01158 (cold std, n=4), and [$^{177}$Lu]Lu-CCZ01158 (26.7±3.6 MBq, n=4). The median survival of the three groups was 13, 14 and 29 days.

For radioligand therapy, SK-MEL-1 human melanoma-bearing mice were injected with saline (control group, n=5), non-radioactive lutetium coupled CCZ01158 (cold std, n=4), and [$^{177}$Lu]Lu-CCZ01158 (26.7±3.6 MBq/mouse, n=4). Tumour size and body weight were measured every 2-4 days from the date of injection. Endpoint was defined as >15% weight loss, ulceration of tumours, or tumour volume >1000 mm³ (Volume=width×width×length/2, measured with calliper). With [$^{177}$Lu]Lu-CCZ01158 radiotherapy, the growth of the SK-MEL-1 human melanoma was significantly delayed, with no significant difference between the saline and non-radioactive lutetium coupled CCZ01158 groups (FIG. 7). This confirms the effectiveness of the $^{177}$Lu radiotherapy with CCZ01158 as the melanoma targeting molecule. With the [$^{177}$Lu]Lu-CCZ01158 radiotherapy, mice had a median survival of 29 days, a significant improvement over the 13 and 14 days for the saline and cold std groups (FIG. 8). All mice were euthanized when the tumours reached over 1000 mm³, except for one mouse due to weight loss in the saline group, and one mouse due to tumour ulceration in the cold std group. No obvious adverse effects were observed in the [$^{177}$Lu]Lu-CCZ01158 radiotherapy group.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A compound comprising a melanocortin 1 receptor (MC1R) targeting peptide (MC1RTP), a radiolabeling group, and a linker joining the MC1RTP to the radiolabeling group, wherein:

the MCR1TP is cyclized and comprises a sequence of Formula I:

Xaa$^1$-Xaa$^{2a}$-Xaa$^3$-Xaa$^4$-Xaa$^5$-Xaa$^6$-Xaa$^{7a}$     (I)

Xaa$^1$ is selected from the group consisting of norleucine (Nle), D-Nle, Ala, D-Ala, Leu, D-Leu, Ile, D-Ile, Cys, D-Cys, Met, D-Met, Phe, D-Phe, Trp, D-Trp, Val, D-Val, 3-(l-naphthyl)alanine (Nal), D-Nal, 3-(2-naphthyl)alanine (2-Nal), D-2-Nal, Gly, α-aminobutyric acid, norvaline, D-norvaline, homonorleucine, and D-homonorleucine;

Xaa$^{2a}$ is selected from the group consisting of Cys, D-Cys, Asp, D-Asp, Glu, D-Glu, 2-aminoadipic acid (2-Aad), D-2-Aad, 3-aminoadipic acid (3-Aad), D-3-Aad, propargylglycine (Pra), D-Pra, homopropargylglycine (Hpg), D-Hpg, beta-homopropargylglycine (Bpg), and D-Bpg;

Xaa$^3$ is His;

Xaa$^4$ is D-Phe;

Xaa$^5$ is Arg;

Xaa$^6$ is Trp;

Xaa$^{7a}$ is selected from the group consisting of Cys, D-Cys, Lys, D-Lys, Orn, D-Orn, Dab, D-Dab, Dap, D-Dap, Lys(N$_3$), D-Lys(N$_3$), Orn(N$_3$), D-Orn(N$_3$), Dab(N$_3$), D-Dab(N$_3$), Dap(N$_3$), D-Dap(N$_3$), 2-(5'-azidopentyl)alanine, D-2-(5'-azidopentyl)alanine, 2-(6'-azidohexyl)alanine, and D-2-(6'-azidohexyl)alanine;

one or more amino acid residues of the MC1RTP is alpha N-methylated, wherein one or more of Xaa$^3$, Xaa$^5$, Xaa$^6$, and Xaa$^{7a}$ is alpha N-methylated; and the MCR1TP is optionally C-terminally amidated.

2. The compound of claim 1, wherein the MC1RTP is cyclized by a lactam bridge connecting Xaa$^{2a}$ to Xaa$^{7a}$.

3. The compound of claim 2, wherein the lactam bridge connects the side chain of Asp and Lys.

4. The compound of claim 2, wherein Xaa$^1$ is norleucine (Nle), Xaa$^{2a}$ is Asp, Xaa$^3$ is His, Xaa$^4$ is D-Phe, Xaa$^5$ is Arg, Xaa$^6$ is Trp, and Xaa$^{7a}$ is Lys.

5. The compound of claim 4, wherein only Xaa$^5$ and Xaa$^{7a}$ are alpha N-methylated.

6. The compound of claim 5, wherein the linker is:

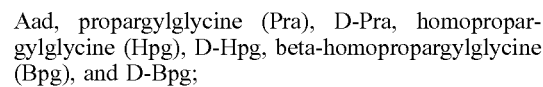

or

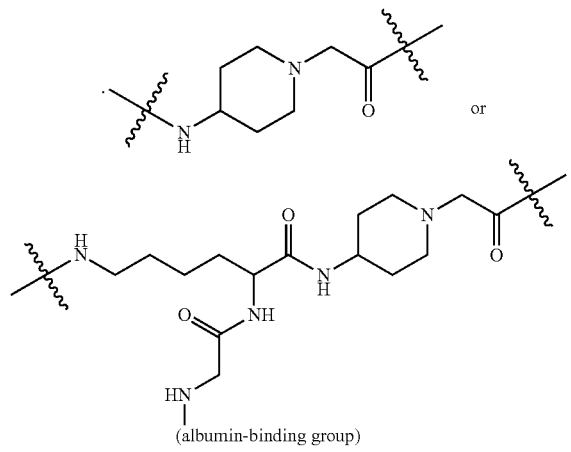

(albumin-binding group)

7. The compound of claim 6, wherein the linker is:

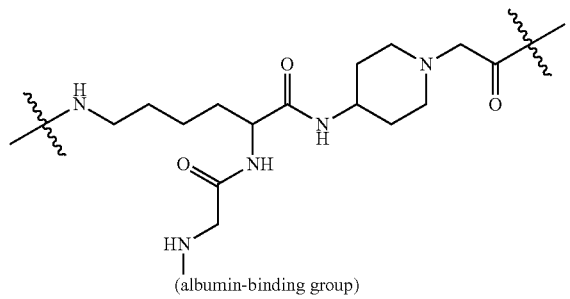

and the albumin-binding group has the following structure:

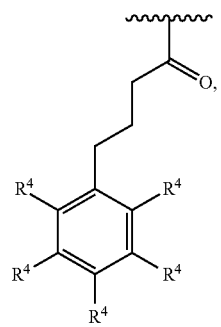

wherein each R⁴ is independently H, halogen, $C_{1-5}$ alkyl, $C_{1-5}$ alkoxy, or nitro.

8. The compound of claim 7, wherein the albumin-binding group is N-[4-(p-tolyl)butanoyl].

9. The compound of claim 8, wherein the radiolabeling group comprises a chelator conjugated to a radiometal, and the chelator is selected from the group consisting of DOTA; DOTAGA; NOTA; NODAGA; NODASA; CBDO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; macropa; $H_2$dedpa, $H_4$octapa, $H_4$py$_4$pa, $H_4$Pypa, $H_2$azapa, $H_5$decapa, and other picolinic acid derivatives; CP256; PCTA; C-NETA; C-NE3TA; HBED; SHBED; BCPA; YM103; desferrioxamine (DFO) and DFO derivatives; and $H_6$phospa.

10. The compound of claim 9, wherein the chelator is macropa or DOTA.

11. The compound of claim 10, wherein when the chelator is macropa, the compound is conjugated with a radioisotope selected from the group consisting of $^{225}$Ac and $^{227}$Th, and when the chelator is DOTA, the compound is conjugated with a radioisotope selected from the group consisting of $^{177}$Lu, $^{114m}$In, $^{111}$In, $^{212}$Bi, $^{213}$Bi, $^{68}$Ga, $^{67}$Ga, $^{203}$Pb, $^{212}$Pb, $^{47}$Sc, $^{44}$Sc, $^{90}$Y, $^{86}$Y, $^{61}$CU, $^{64}$CU, $^{67}$CU, $^{117m}$Sn, $^{175}$Yb, $^{90}$Nb, and $^{225}$Ac.

12. The compound of claim 6, wherein the radiolabeling group comprises a chelator conjugated to a radioisotope, and the chelator is selected from the group consisting of DOTA; DOTAGA; NOTA; NODAGA; NODASA; CBDO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; macropa; $H_2$dedpa, $H_4$octapa, $H_4$py$_4$pa, $H_4$Pypa, $H_2$azapa, $H_5$decapa, and other picolinic acid derivatives; CP256; PCTA; C-NETA; C-NE3TA; HBED; SHBED; BCPA; YM103; desferrioxamine (DFO) and DFO derivatives; and $H_6$phospa.

13. The compound of claim 12, wherein the chelator is macropa or DOTA.

14. The compound of claim 13, wherein when the chelator is macropa, the compound is conjugated with a radioisotope selected from the group consisting of $^{225}$Ac and $^{227}$Th, and when the chelator is DOTA, the compound is conjugated with a radioisotope selected from the group consisting of $^{177}$Lu, $^{114m}$In, $^{111}$In, $^{212}$Bi, $^{213}$Bi, $^{68}$Ga, $^{67}$Ga, $^{203}$Pb, $^{212}$Pb, $^{47}$Sc, $^{44}$Sc, $^{90}$Y, $^{86}$Y, $^{61}$CU, $^{64}$CU, $^{67}$CU, $^{117m}$Sn, $^{175}$Yb, $^{90}$Nb, and $^{225}$Ac.

15. A method of PET or SPECT imaging of cutaneous or ocular melanoma, comprising administering a compound of claim 5, wherein the compound is conjugated with a radioisotope selected from the group consisting of $^{177}$Lu, $^{111}$In, $^{68}$Ga, $^{67}$Ga, $^{203}$Pb, $^{44}$Sc, $^{86}$Y, $^{61}$Cu, $^{64}$Cu, $^{117m}$Sn, and $^{90}$Nb and imaging the cutaneous or ocular melanoma.

16. The method of claim 15, wherein the linker is:

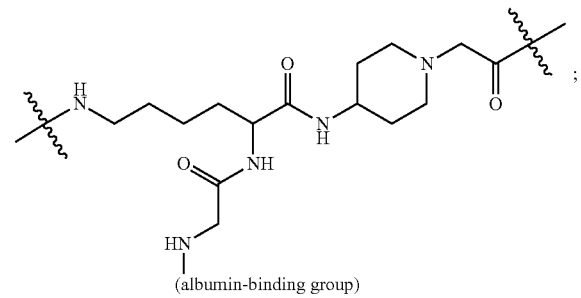

and
the albumin-binding group is N-[4-(p-tolyl)butanoyl].

17. The compound of claim 1, wherein only Xaa⁵ and Xaa⁷ᵃ are alpha N-methylated.

18. The compound of claim 17, wherein the linker is:

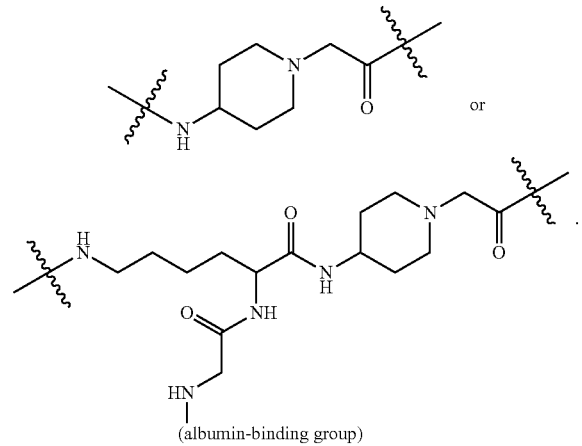

19. The compound of claim 1, wherein the linker comprises an albumin binding group.

20. The compound of claim 19, wherein the albumin-binding group has the following structure:

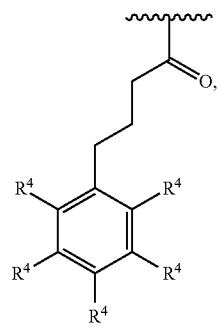

wherein each $R^4$ is independently H, halogen, $C_{1-5}$ alkyl, $C_{1-5}$ alkoxy, or nitro.

21. The compound of claim 1, wherein the radiolabeling group comprises a chelator conjugated to a radioisotope.

22. The compound of claim 21, wherein the chelator is selected from the group consisting of DOTA; DOTAGA; NOTA; NODAGA; NODASA; CBDO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; macropa; $H_2$dedpa, $H_4$octapa, $H_4$py$_4$pa, $H_4$Pypa, $H_2$azapa, $H_5$decapa, and other picolinic acid derivatives; CP256; PCTA; C-NETA; C-NE3TA; HBED; SHBED; BCPA; YM103; desferrioxamine (DFO) and DFO derivatives; and $H_6$phospa.

23. The compound of claim 22, wherein the chelator is macropa or DOTA.

24. The compound of claim 23, wherein when the chelator is macropa, the compound is conjugated with a radioisotope selected from the group consisting of $^{225}$Ac and $^{227}$Th, and when the chelator is DOTA, the compound is conjugated with a radioisotope selected from the group consisting of $^{177}$Lu, $^{114m}$In, $^{111}$In, $^{212}$Bi, $^{213}$Bi, $^{68}$Ga, $^{67}$Ga, $^{203}$Pb, $^{212}$Pb, $^{47}$Sc, $^{44}$Sc, $^{90}$Y, $^{86}$Y, $^{61}$CU, $^{64}$CU, $^{67}$CU, $^{117m}$Sn, $^{175}$Yb, $^{90}$Nb, and $^{225}$Ac.

25. The compound of claim 1, wherein the linker is:

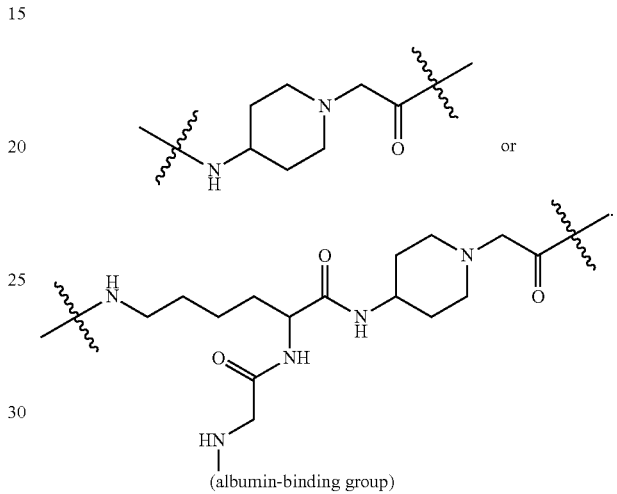

(albumin-binding group)

26. A compound of claim 1, having the following structure and optionally conjugated with a radioisotope selected from the group consisting of $^{177}$Lu, $^{114m}$In, $^{111}$In, $^{212}$Bi, $^{213}$Bi, $^{203}$Pb, $^{212}$Pb, $^{61}$Cu, $^{64}$Cu, $^{67}$Cu, $^{117m}$Sn, $^{47}$Sc, $^{90}$Y, and $^{225}$Ac:

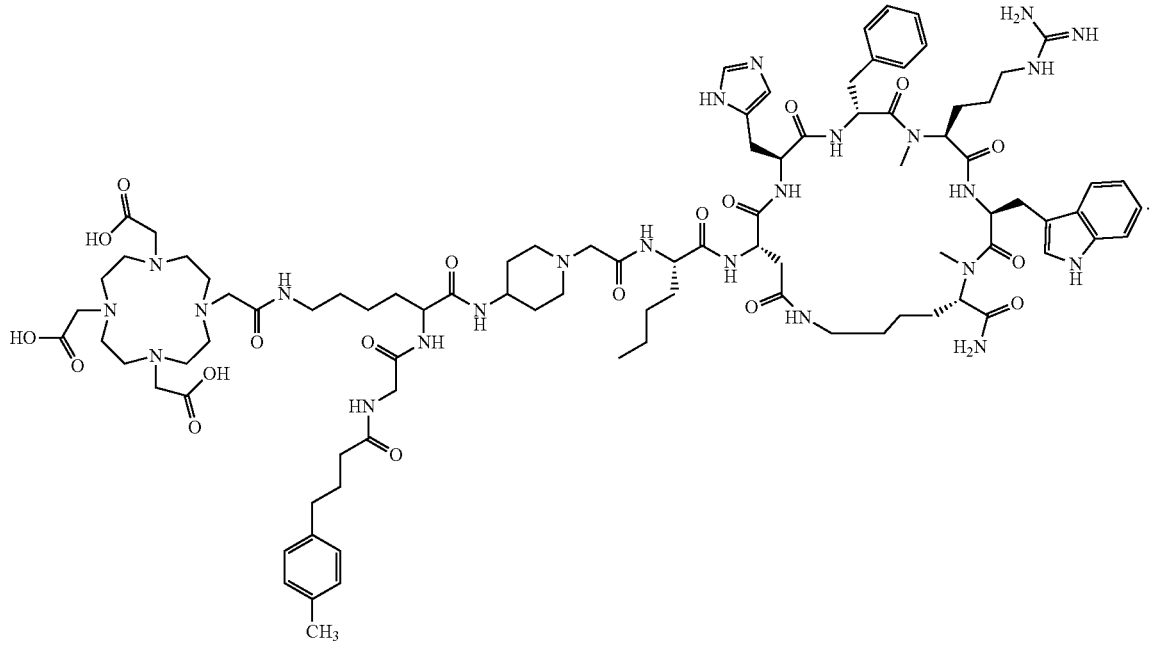 [SMILES: CCCC[C@H](NC(=O)CN1CCC(NC(=O)C(CCCCNC(=O)CN2CCN(CC(=O)O)CCN(CC(=O)O)CCN(CC(=O)O)CC2)NC(=O)CNC(=O)CCCc2ccc(C)cc2)CC1)C(=O)N[C@H]1CC(=O)NCCCC[C@@H](C(N)=O)N(C)C(=O)[C@H](Cc2c[nH]c3ccccc23)NC(=O)[C@H](CCCNC(=N)N)N(C)C(=O)[C@@H](Cc2ccccc2)NC(=O)[C@H](Cc2cnc[nH]2)NC1=O]

27. A method of treating metastatic cutaneous melanoma or metastatic uveal melanoma, comprising administering a compound of claim 26, wherein the compound is conjugated with a radioisotope selected from the group consisting of $^{177}$Lu, $^{114m}$In, $^{111}$In, $^{212}$Bi, $^{213}$Bi, $^{203}$Pb, $^{212}$Pb, $^{61}$Cu, $^{64}$Cu, $^{67}$Cu, $^{117m}$Sn, $^{47}$Sc, $^{90}$Y, and $^{225}$Ac.

28. A compound of claim 1, having the following structure and optionally conjugated with a radioisotope selected from the group consisting of $^{225}$Ac and $^{227}$Th:

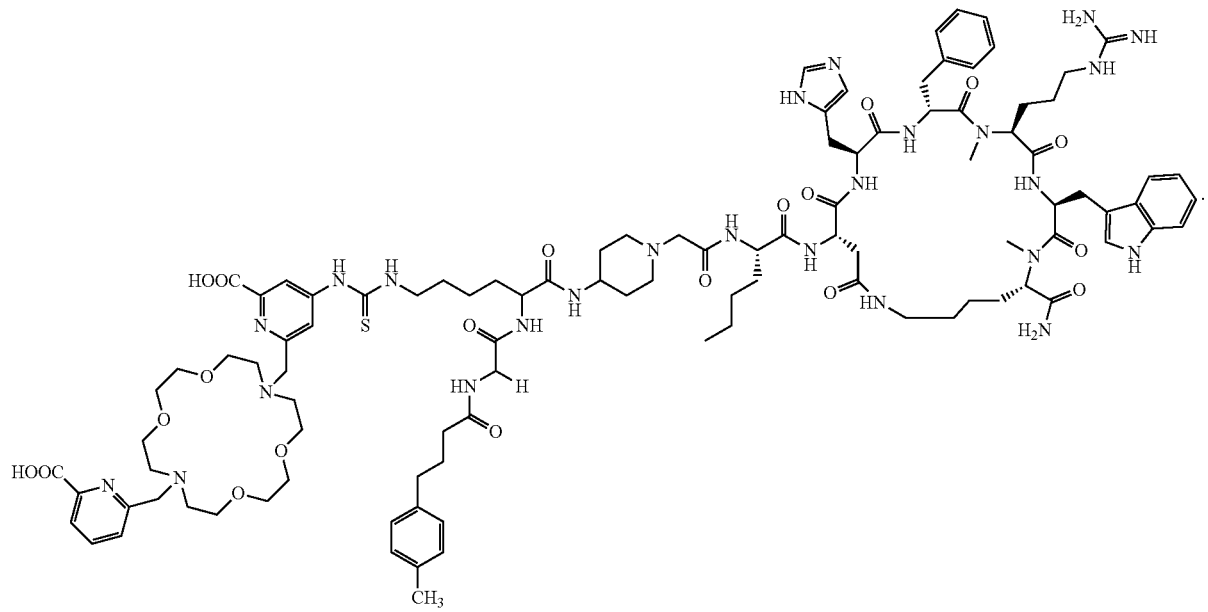 [SMILES: CCCC[C@H](NC(=O)CN1CCC(NC(=O)C(CCCCNC(=S)Nc2cc(CN3CCOCCOCCN(Cc4cccc(C(=O)O)n4)CCOCCOCC3)nc(C(=O)O)c2)NC(=O)CNC(=O)CCCc2ccc(C)cc2)CC1)C(=O)N[C@H]1CC(=O)NCCCC[C@@H](C(N)=O)N(C)C(=O)[C@H](Cc2c[nH]c3ccccc23)NC(=O)[C@H](CCCNC(=N)N)N(C)C(=O)[C@@H](Cc2ccccc2)NC(=O)[C@H](Cc2cnc[nH]2)NC1=O]

29. A method of treating metastatic cutaneous melanoma or metastatic uveal melanoma, comprising administering a compound of claim 28, wherein the compound is conjugated with a radioisotope selected from the group consisting of $^{227}$Th and $^{225}$Ac.

30. A method of PET or SPECT imaging of cutaneous or ocular melanoma, comprising administering a compound of claim 1, wherein the compound is conjugated with a radioisotope selected from the group consisting of $^{177}$Lu, $^{111}$In, $^{68}$Ga, $^{67}$Ga, $^{203}$Pb, $^{44}$Sc, $^{86}$Y, $^{61}$Cu, $^{64}$Cu, $^{117m}$Sn, and $^{90}$Nb and imaging the cutaneous or ocular melanoma.

31. A method of treating metastatic cutaneous melanoma or metastatic uveal melanoma, comprising administering a compound of claim 1, wherein the compound is conjugated with a radioisotope selected from the group consisting of $^{177}$Lu, $^{114m}$In, $^{111}$In, $^{212}$Bi, $^{213}$Bi, $^{203}$Pb, $^{212}$Pb, $^{61}$Cu, $^{64}$Cu, $^{67}$Cu, $^{117m}$Sn, $^{47}$Sc, $^{90}$Y, and $^{225}$Ac.

32. The method of claim 31, wherein:
the MC1RTP is cyclized by a lactam bridge connecting Xaa$^{2a}$ to Xaa$^{7a}$;
Xaa$^1$ is norleucine (Nle), Xaa$^{2a}$ is Asp, Xaa$^3$ is His, Xaa$^4$ is D-Phe, Xaa$^5$ is Arg, Xaa$^6$ is Trp, and Xaa$^{7a}$ is Lys; and
only Xaa$^5$ and Xaa$^{7a}$ are alpha N-methylated.

33. The method of claim 32, wherein the linker is:

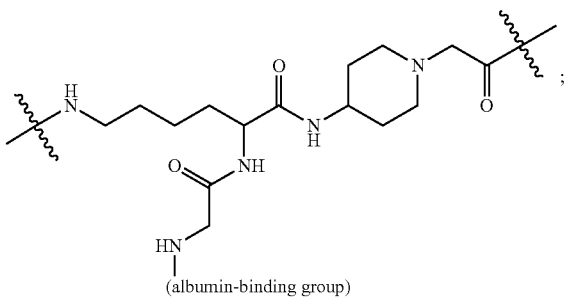

and
the albumin-binding group is N-[4-(p-tolyl)butanoyl].

* * * * *

UNITED STATES PATENT AND TRADEMARK OFFICE
CERTIFICATE OF CORRECTION

PATENT NO. : 11,395,857 B2
APPLICATION NO. : 17/494367
DATED : July 26, 2022
INVENTOR(S) : Bénard et al.

It is certified that error appears in the above-identified patent and that said Letters Patent is hereby corrected as shown below:

In the Claims

At Claim 1, Column 57, Line 57, please replace "Xaa$^{73}$" with --Xaa$^{7a}$--

At Claim 1, Column 57, Line 59, please replace "lie," with --Ile,--

At Claim 1, Column 57, Line 61, please replace "3-(l-naphthyl)alanine (Nal)," with --3-(1-naphthyl)alanine (Nal),--

At Claim 9, Column 59, Line 48, please replace "H$_2$decapa" with --H$_5$decapa--

At Claim 11, Column 59, Line 60, please replace "$^{61}$CU, $^{64}$CU, $^{67}$CU," with --$^{61}$Cu, $^{64}$Cu, $^{67}$Cu,--

At Claim 14, Column 6, Line 19, please replace "$^{61}$CU, $^{64}$CU, $^{67}$CU," with --$^{61}$Cu, $^{64}$Cu, $^{67}$Cu,--

At Claim 15, Column 6, Line 25, please replace "$^{90}$Nb" with --$^{90}$Nb;--

At Claim 24, Column 62, Line 11, please replace "$^{61}$CU, $^{64}$CU, $^{67}$CU," with --$^{61}$Cu, $^{64}$Cu, $^{67}$Cu,--

At Claim 30, Column 63, Line 46, please replace "$^{90}$Nb" with --$^{90}$Nb;--

Signed and Sealed this
Sixth Day of December, 2022

Katherine Kelly Vidal
*Director of the United States Patent and Trademark Office*

Page 1 of 1